(12) United States Patent
Goronzy et al.

(10) Patent No.: US 8,685,938 B2
(45) Date of Patent: Apr. 1, 2014

(54) METHODS TO ENHANCE T-CELL MEDIATED IMMUNE RESPONSE

(75) Inventors: Jorg J Goronzy, Palo Alto, CA (US); Cornelia Weyand, Palo Alto, CA (US); Mingcan Yu, Palo Alto, CA (US)

(73) Assignees: The Board of Trustees of the Leland Stanford Junior University, Palo Alto, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/082,790

(22) Filed: Apr. 8, 2011

(65) Prior Publication Data

US 2011/0281932 A1     Nov. 17, 2011

Related U.S. Application Data

(60) Provisional application No. 61/322,297, filed on Apr. 9, 2010, provisional application No. 61/358,398, filed on Jun. 24, 2010.

(51) Int. Cl.
*A61K 48/00*     (2006.01)

(52) U.S. Cl.
USPC .............................................. 514/44; 536/24.5

(58) Field of Classification Search
None
See application file for complete search history.

(56) References Cited

U.S. PATENT DOCUMENTS

| 6,566,133 | B1 * | 5/2003 | Cowsert | 435/375 |
| 6,841,369 | B1 * | 1/2005 | Luche et al. | 435/196 |
| 2003/0232441 | A1 * | 12/2003 | Monia et al. | 435/375 |

OTHER PUBLICATIONS

Dickinson et al. (J. Cell Science 2006, vol. 119: 4607-4615).*

* cited by examiner

*Primary Examiner* — Kimberly Chong
(74) *Attorney, Agent, or Firm* — Andrea Blecken

(57) ABSTRACT

The present invention provides methods for restoring or enhancing T cell mediated immune response in individuals of middle and advanced age.

13 Claims, 34 Drawing Sheets

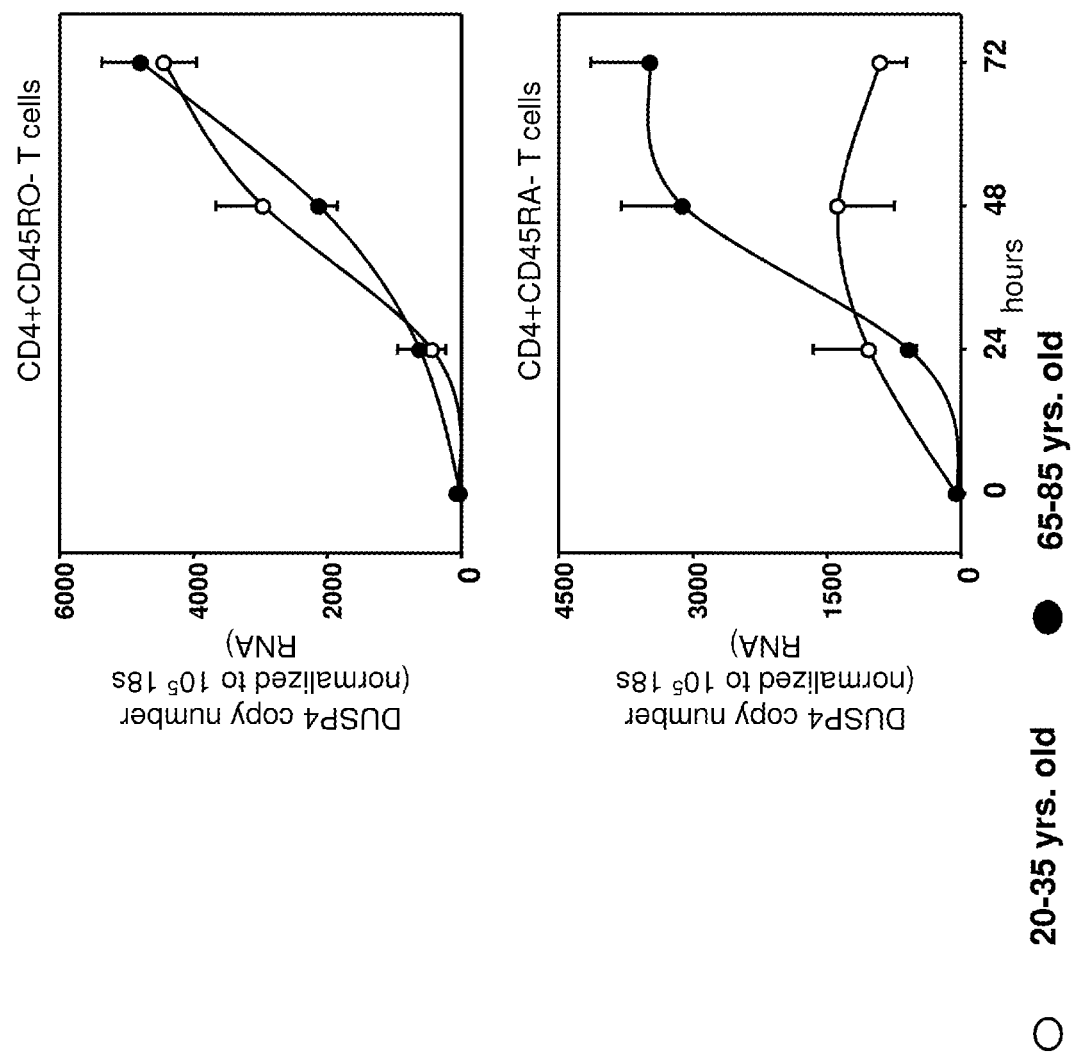

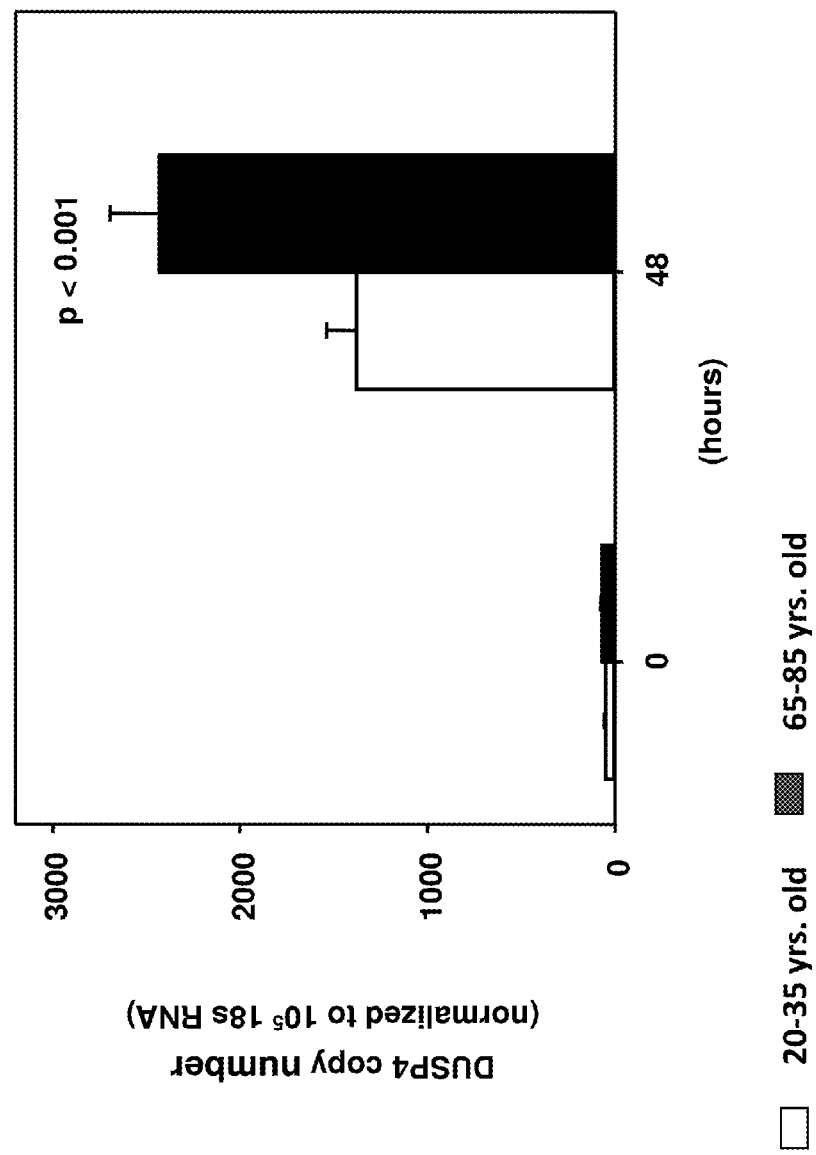

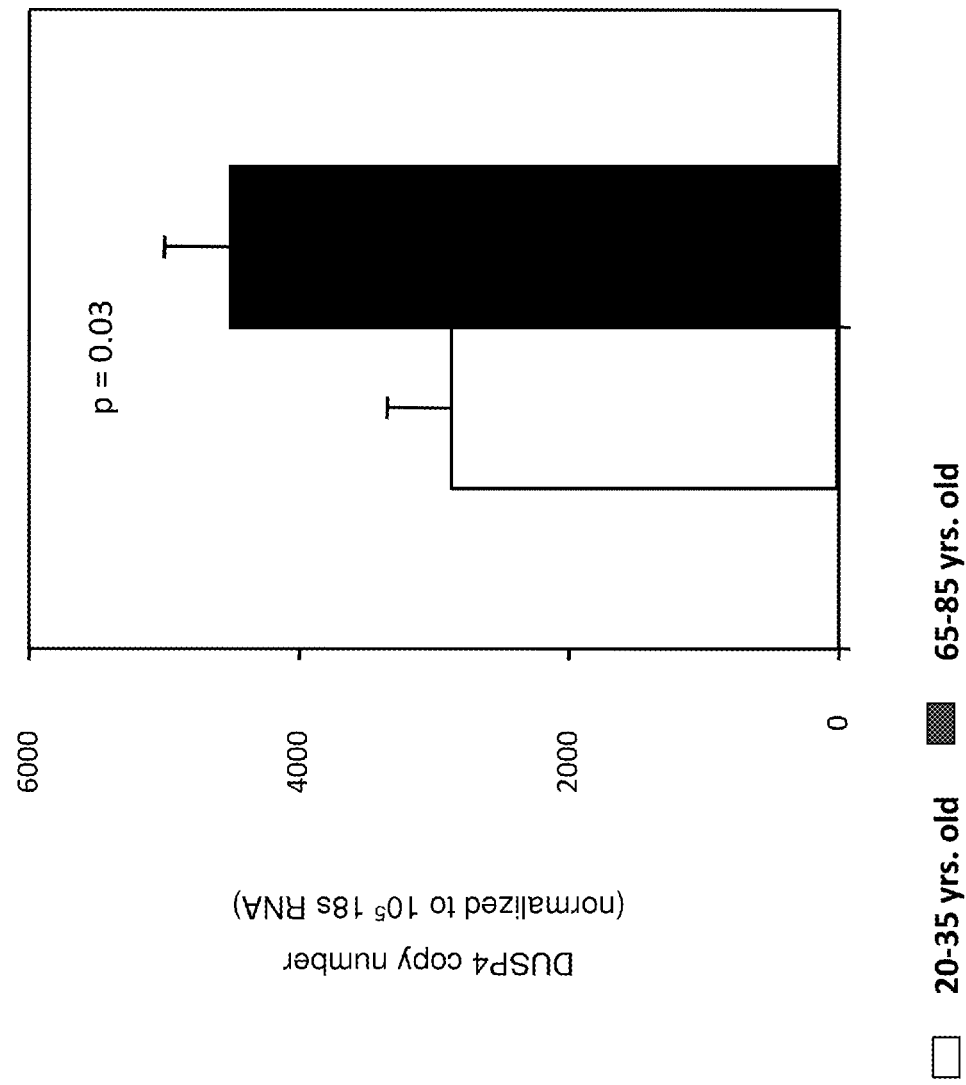

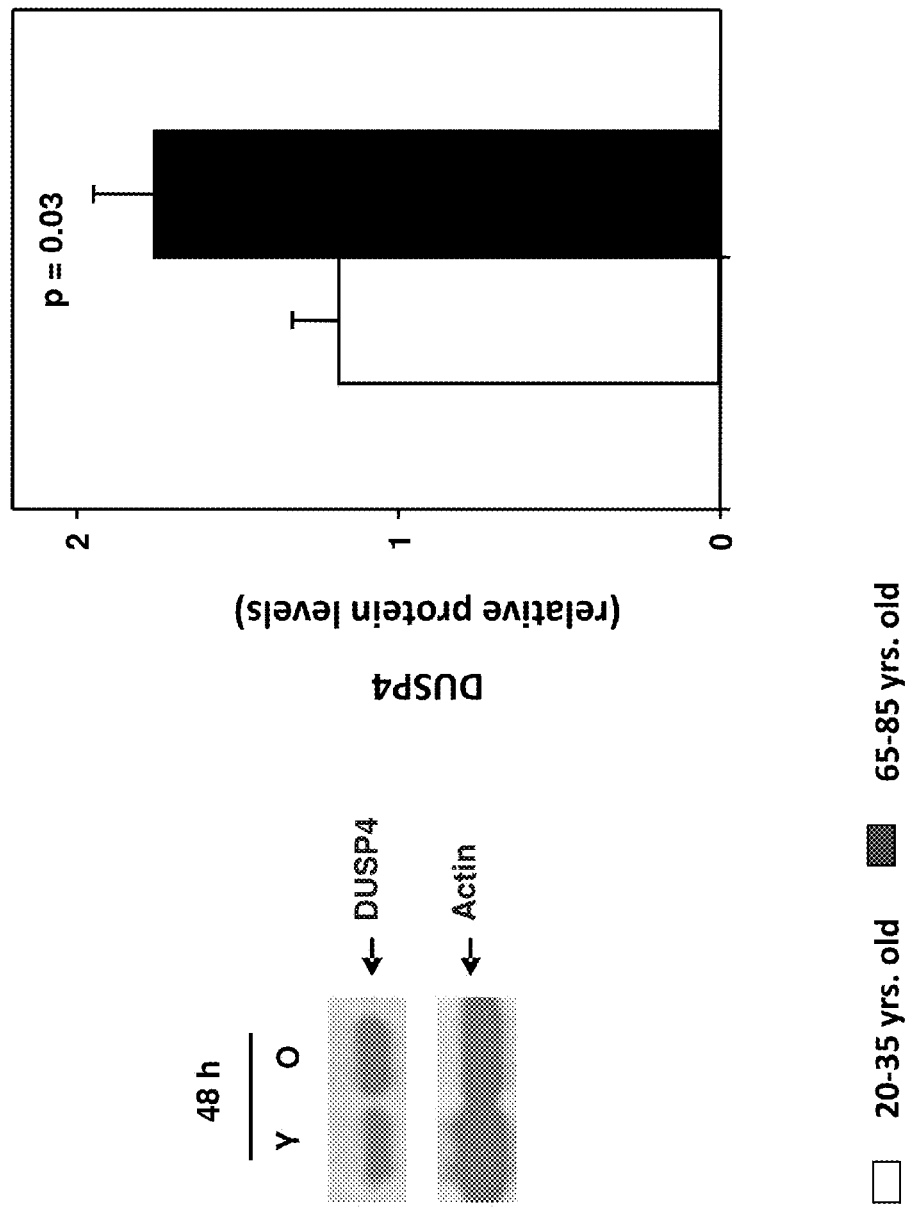

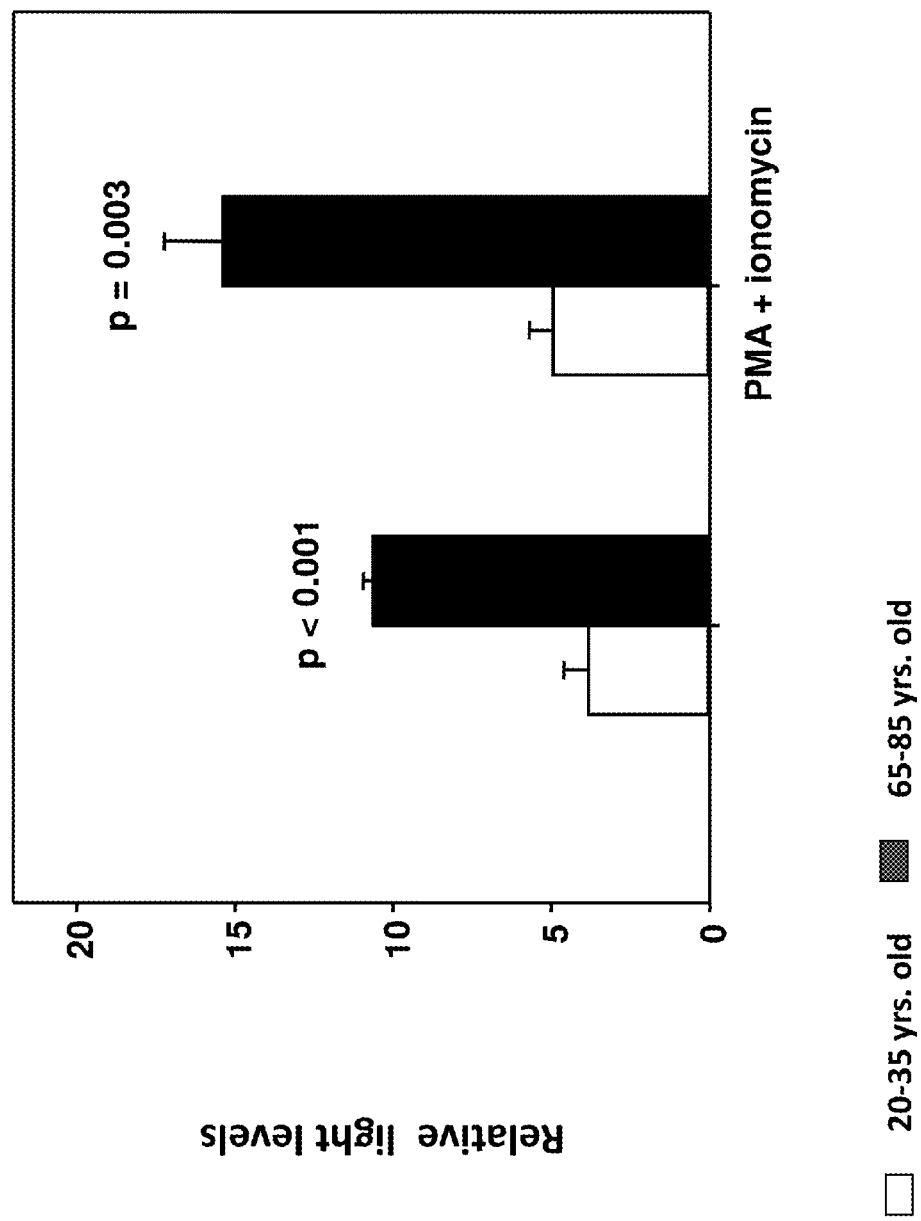

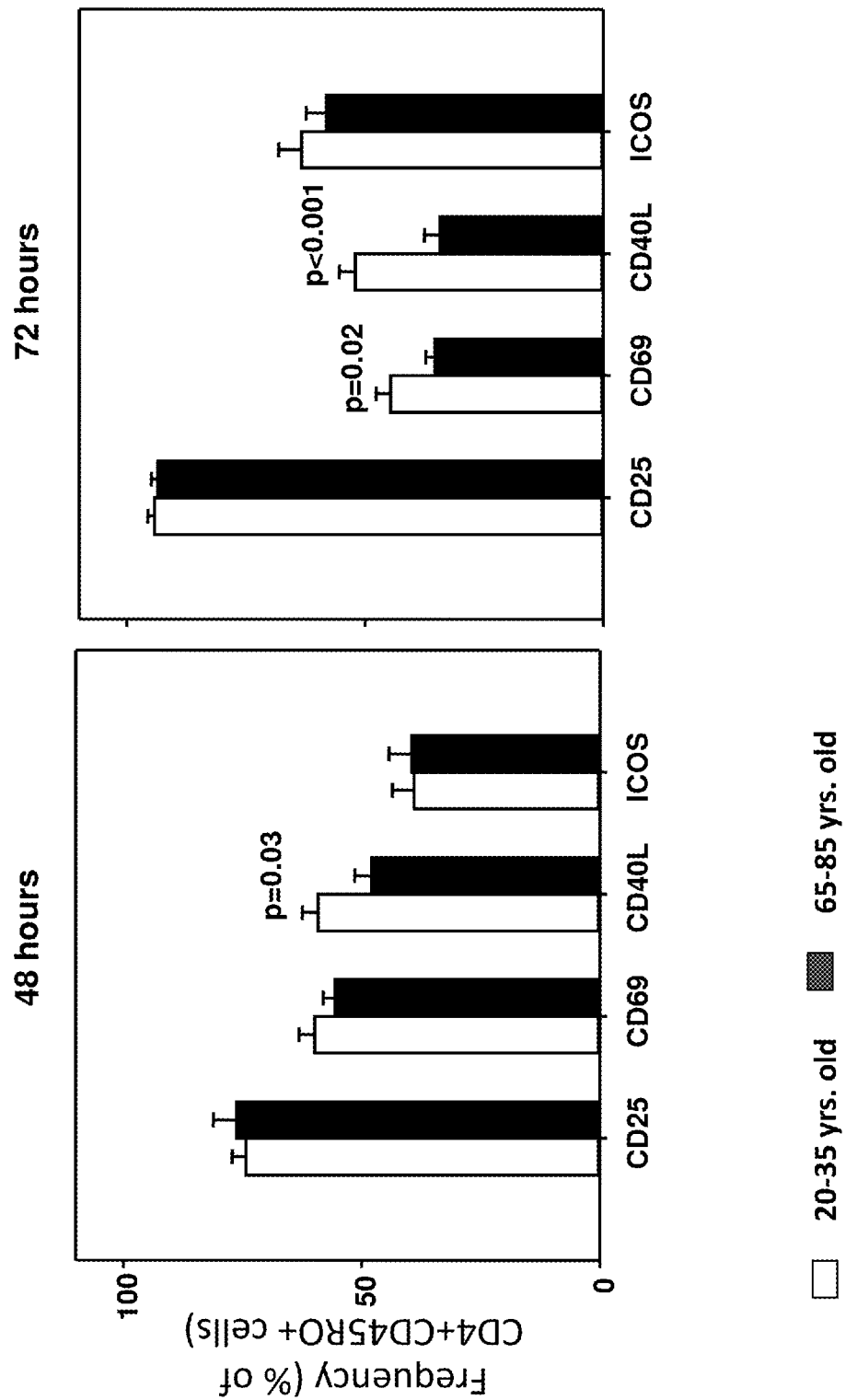

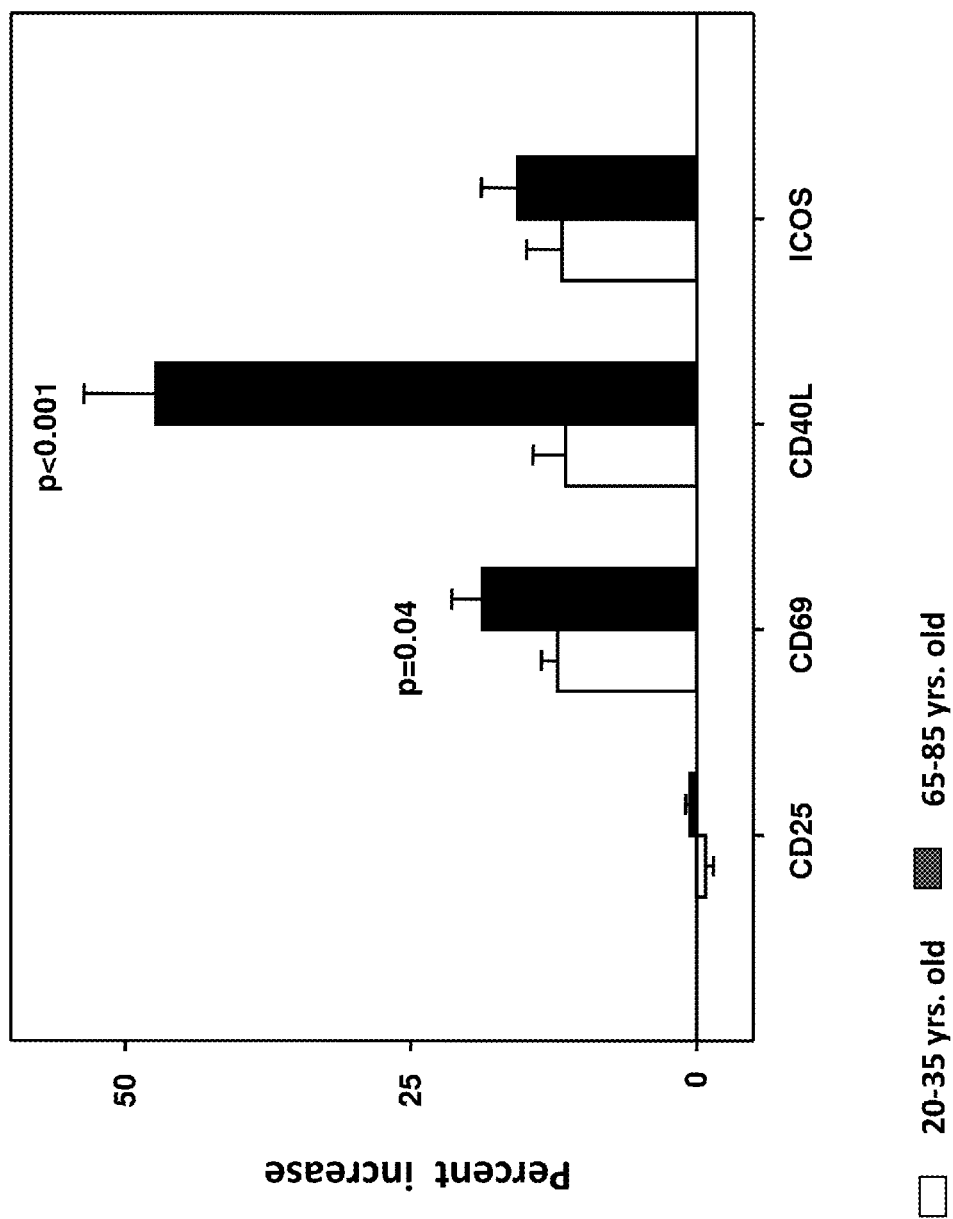

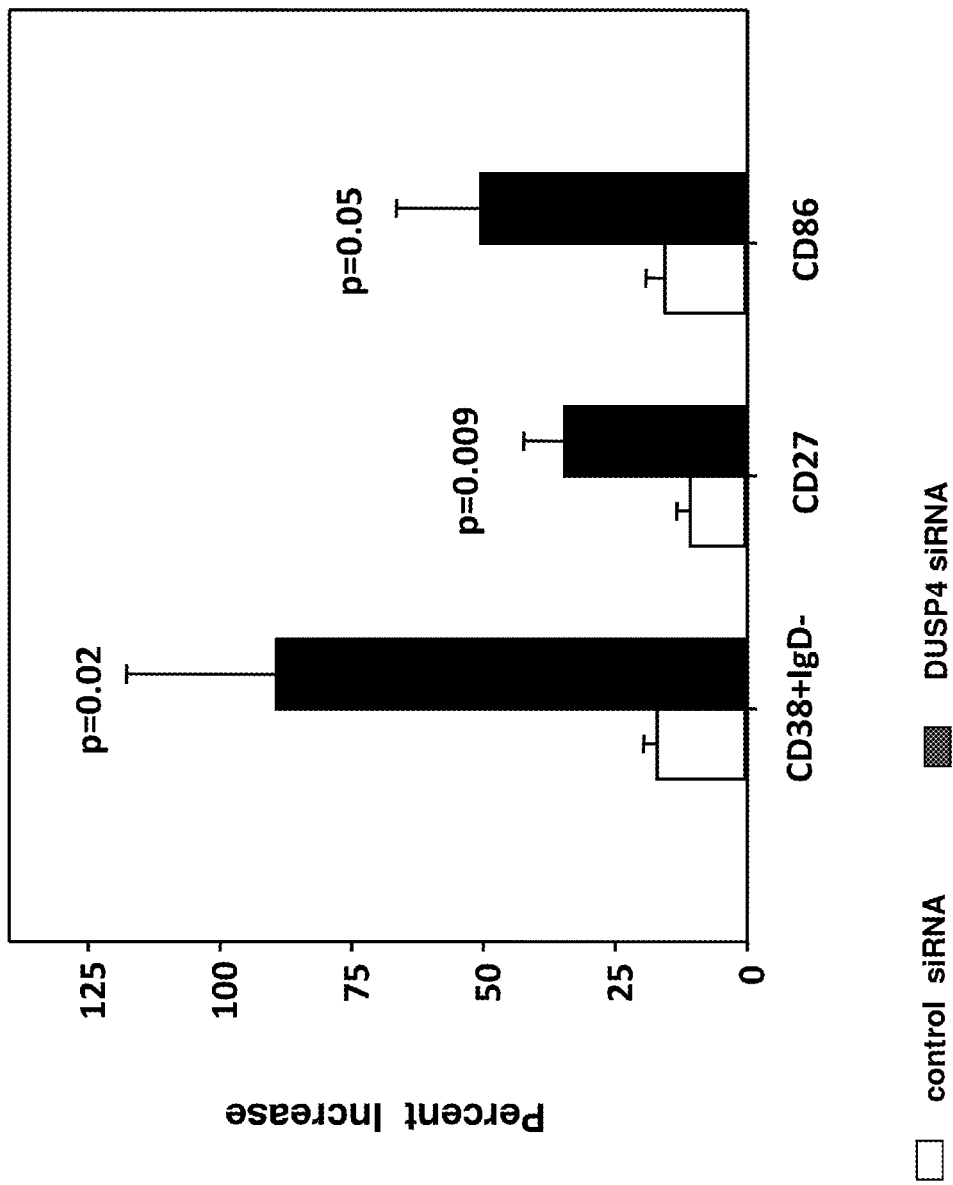

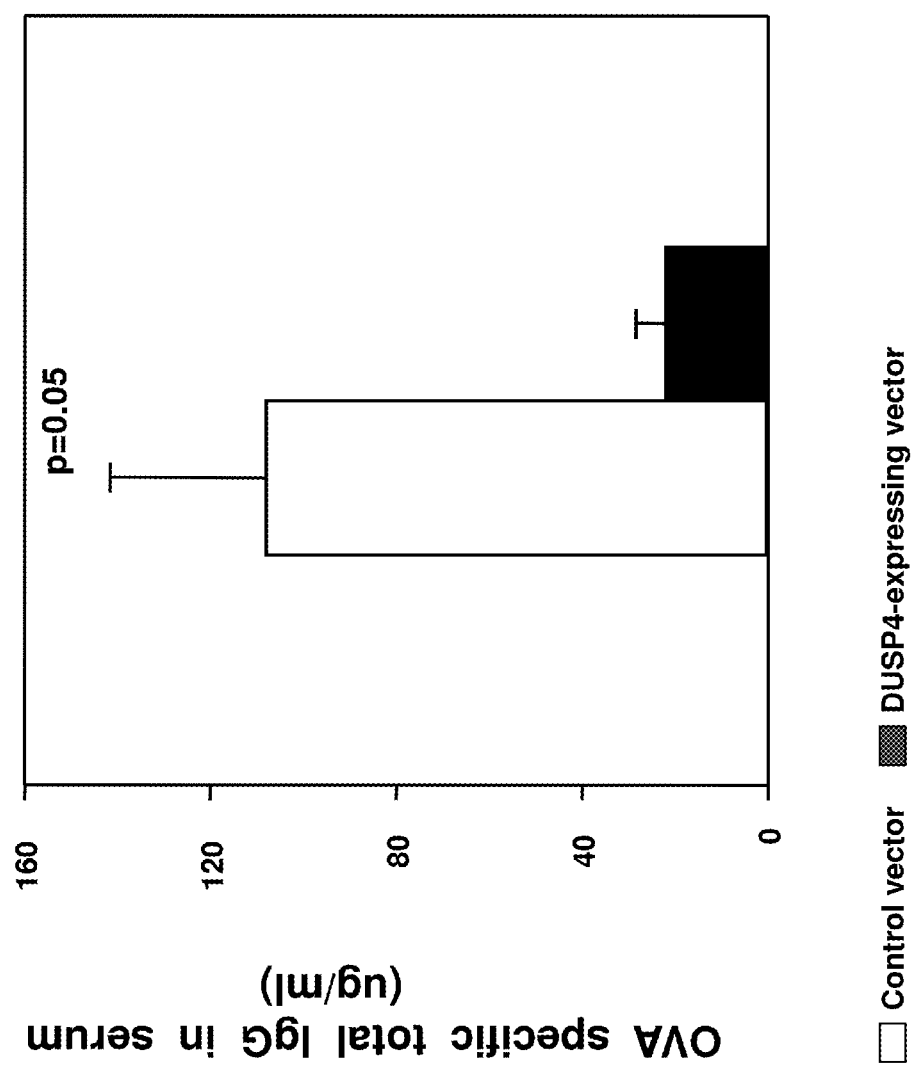

METHODS TO ENHANCE T-CELL MEDIATED IMMUNE RESPONSE

RELATED APPLICATION

This application claims priority and other benefits from U.S. Provisional Patent Application Ser. No. 61/322,297, filed Apr. 9, 2010, entitled "Methods to enhance T-cell-mediated immune response" and Ser. No. 61/358,398, filed Jun. 24, 2010, entitled "Methods to enhance immune response". The entire content of both applications is specifically incorporated herein by reference.

STATEMENT OF GOVERNMENTAL SUPPORT

This invention was made with government support under U19-AI57266 and AG R01 015043 awarded by the National Institutes of Health. The government has certain rights in this invention.

INCORPORATION OF SEQUENCE LISTING

A computer readable form of the sequence listing, "Seq_Listing_ASB026UTL_ST25.txt", 4 kilo bytes, created on Jul. 3, 2011, submitted via EFS-WEB, is herein incorporated by reference.

TECHNICAL FIELD OF THE INVENTION

The present invention relates to methods for restoring or enhancing T cell-mediated immune response in an individual.

BACKGROUND

The primary role of the immune system is to protect against antigens derived from invading pathogens while recognizing and maintaining a tolerance to self-antigens. The recognition of self-antigens and maintenance of self-tolerance is facilitated by an intricate network involving effector T cells, helper T cells and (immuno)regulatory T cells.

Active immunization and activation of T cell-mediated immune response can be achieved through the administration of antigenic material or vaccines. Vaccines seek to prevent or ameliorate the harmful effects of many pathogens, and regular vaccination has become an integral part of preventive medicine. The principle of vaccination and immunization for disease prevention depends greatly on the immunological memory that is carried by memory B and T cells and that confers the ability to mount a rapid and strong immune responses to subsequent encounters with pathogens.

The ability of the immune system to respond to active vaccination with the buildup of a protective immunological memory progressively declines, however, with increasing age, rendering the elderly particularly vulnerable to infections, autoimmune diseases and neoplastic diseases. Although the elderly are considered at risk of complications of influenza and annual influenza vaccinations are strongly recommended by the World Health Organization for this population group, currently only 20% of elderly respond to such vaccinations with a sufficiently strong, protective immune response, while the remaining 80% remain vulnerable to infections with influenza virus. Age is a confounding factor in vaccine responses not only in the elderly, but already in the middle-aged adult. The decline is only partially explained by a loss of naïve and central memory CD4 T cells due to thymic involution. The present invention addresses this issue.

SUMMARY

Embodiments of the present invention provide methods for restoring or enhancing the immune response in individuals of middle or advanced age by modulating an inhibiting force that negatively impacts T cell activation and differentiation into effective T helper cells. Further embodiments of the present invention provide methods for restoring or enhancing the immune response in individuals of middle or advanced age by modulating inhibiting forces that negatively impact T cell activation and/or differentiation into effective T helper cells.

In particular embodiments, a modulator of the activity or expression of at least one dual specificity phosphatase is administered to an individual of middle or advanced age before active immunization, at the time of active immunization and/or after active immunization in order to restore or enhance said individual's immune response following active immunization. In a particular embodiment, the activity or expression of the dual specificity phosphatase 4 (DUSP4) is modulated. In another embodiment, the activity or expression of the dual specificity phosphatase 6 (DUSP6) is modulated. In yet another embodiment, the activity or expression of DUSP4 and DUSP6 is modulated. In further embodiments, the activity or expression of DUSP1, DUSP4, DUSP5 and DUSP6 is modulated.

The above summary is not intended to include all features and aspects of the present invention nor does it imply that the invention must include all features and aspects discussed in this summary.

INCORPORATION BY REFERENCE

All publications mentioned in this specification are herein incorporated by reference to the same extent as if each individual publication was specifically and individually indicated to be incorporated by reference.

DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

FIG. 1A compares the cell cycle entry of CD4 naïve T cells in 20-35 years old volunteers (n=35) and 70-85 years old volunteers (n=17), in accordance with embodiments of the present invention and as further detailed in Example 1. T cell function was probed by stimulating purified naïve CD4 T cells with the superantigen TSST presented by myeloid dendritic cells from young adult volunteers. A significantly lower number of naïve CD4 T cells responded to stimulation in the elderly individuals, whereby the difference was more pronounced for Vβ2-negative naïve CD4 T cells ($p<0.0001$) that recognize TSST with low affinity than for high affinity Vβ2-positive cells ($p=0.0016$).

FIG. 1B compares the expression of the early activation markers, CD25 and CD69, in 20-35 years old volunteers (n=6) and 70-85 years old volunteers (n=6) age groups, in accordance with embodiments of the present invention and as further detailed in Example 1. Expression of these activation markers in elderly naïve CD4-positive T cells were reduced starting as early as 6 hours after the initiation of the culture.

Figure 3A:
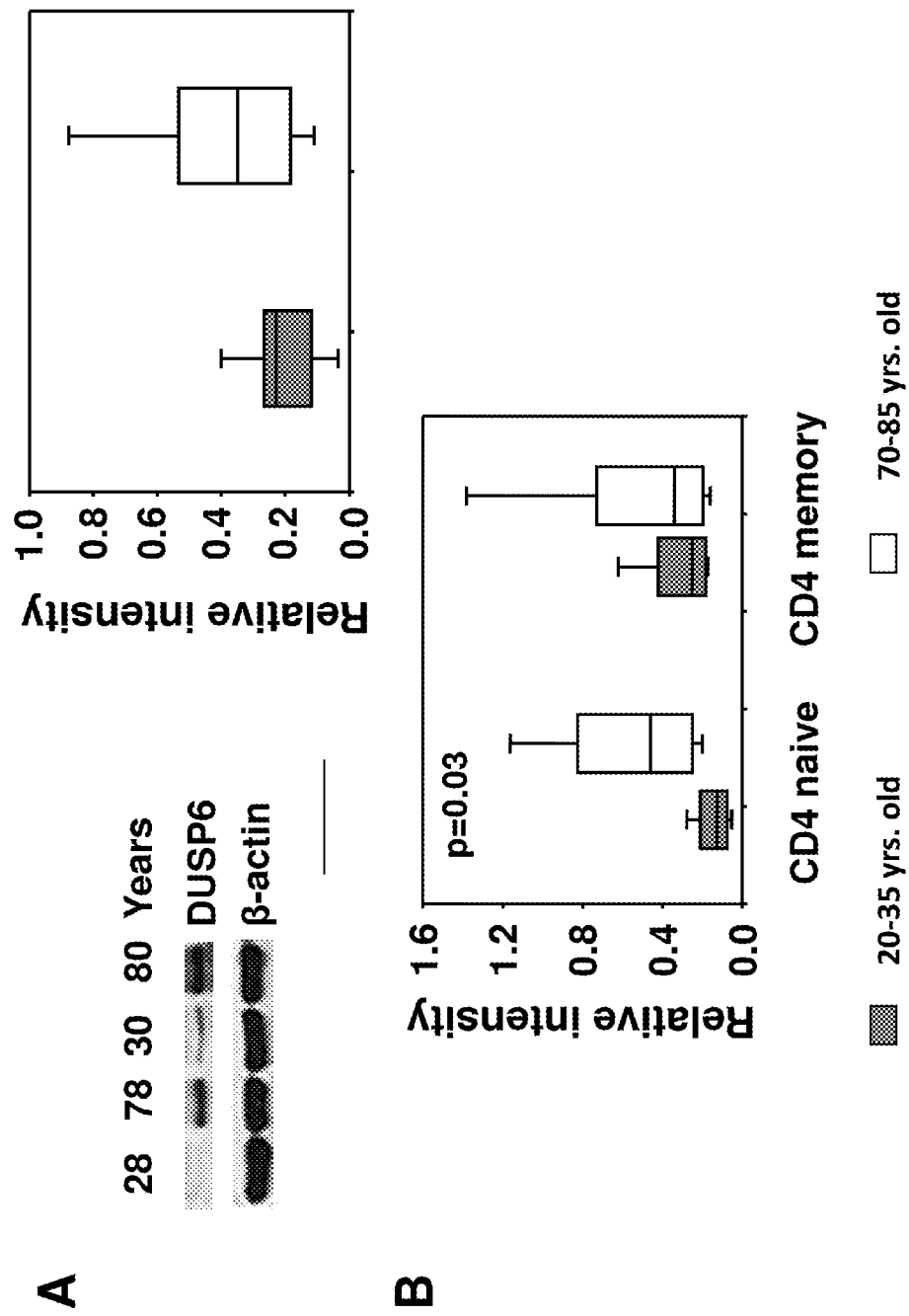

FIG. 3A illustrates DUSP6 protein levels in CD4 T cells in two age groups, in accordance with embodiments of the present invention and as further detailed in Example 3. Panel A: Protein levels in total CD4 T cells. Left panel shows 4 representative donor samples and right panel shows relative intensity of DUSP6 protein levels form 12 young and 12 elderly (p=0.02). Panel B: Protein levels in CD4 naïve and memory T cells (5 young and 5 elderly).

Figure 3B:
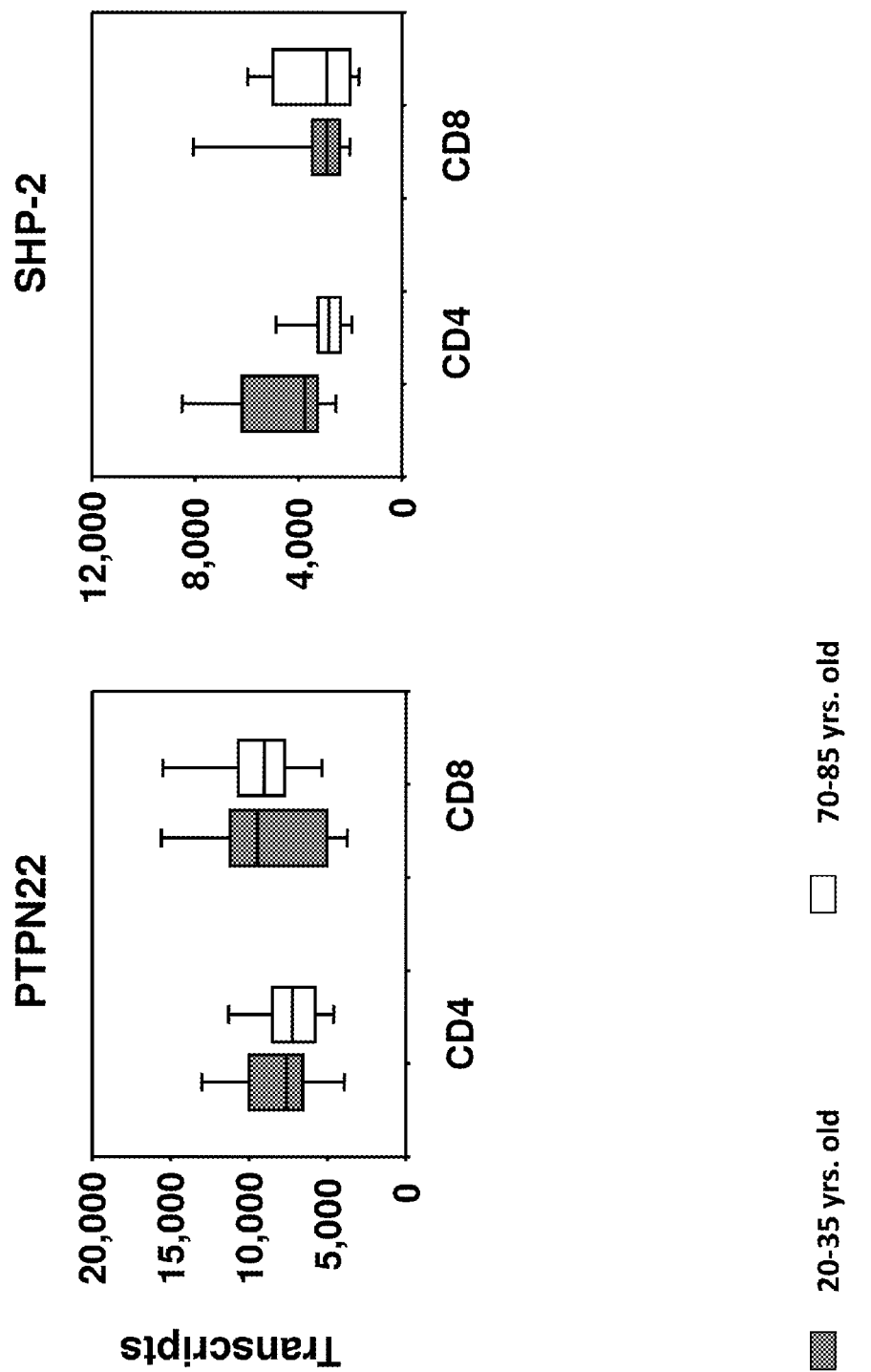

FIG. 3B illustrates PTPN22 and SHP-2 mRNA levels in CD4 and CD8 T cells in two age groups (n=20 per group), in accordance with embodiments of the present invention and as further detailed in Example 3.

Figure 3C:
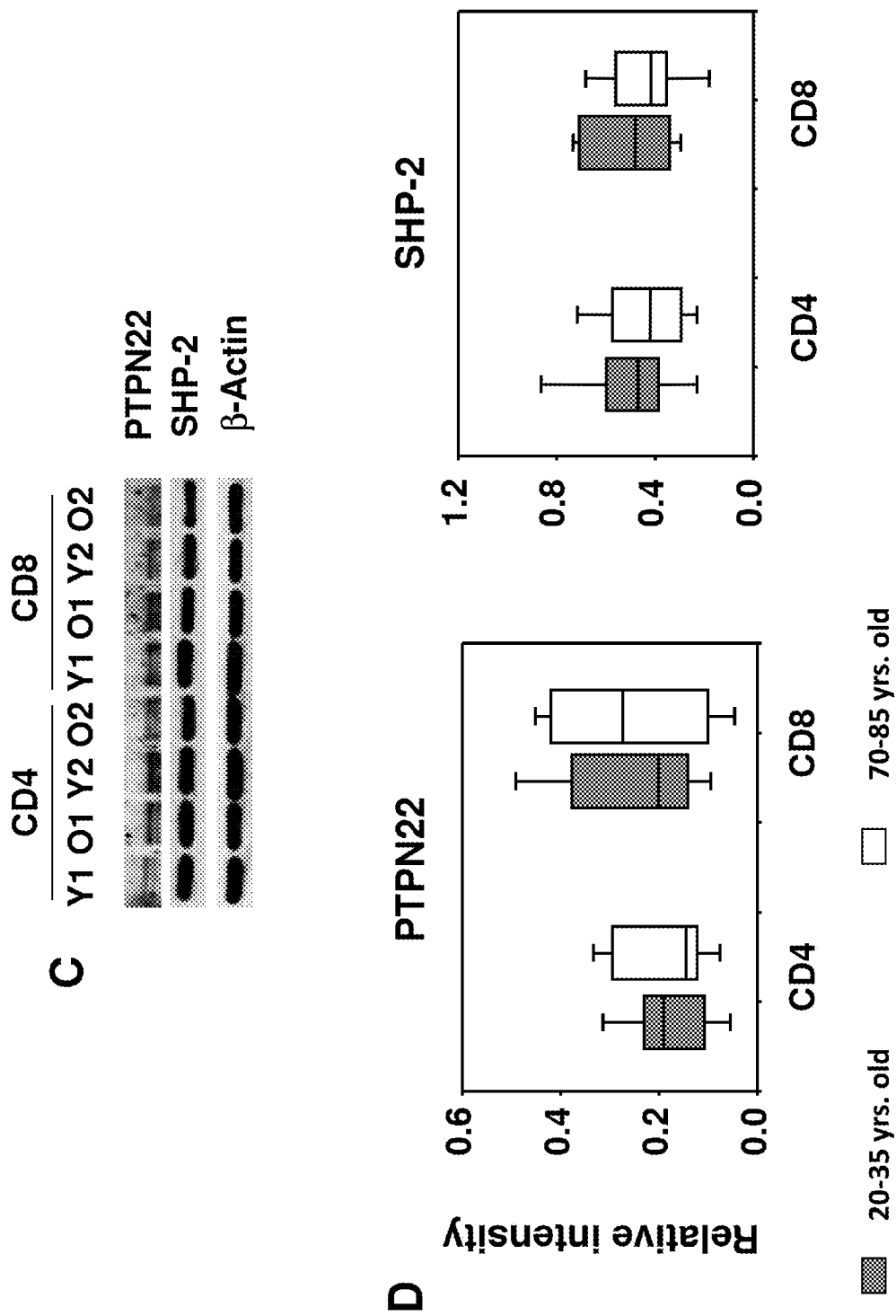

FIG. 3C illustrates PTPN22 and SHP-2 protein levels in CD4 and CD8 T cells in two age groups (n=10 per group), in accordance with embodiments of the present invention and as further detailed in Example 3.

Figure 4A:
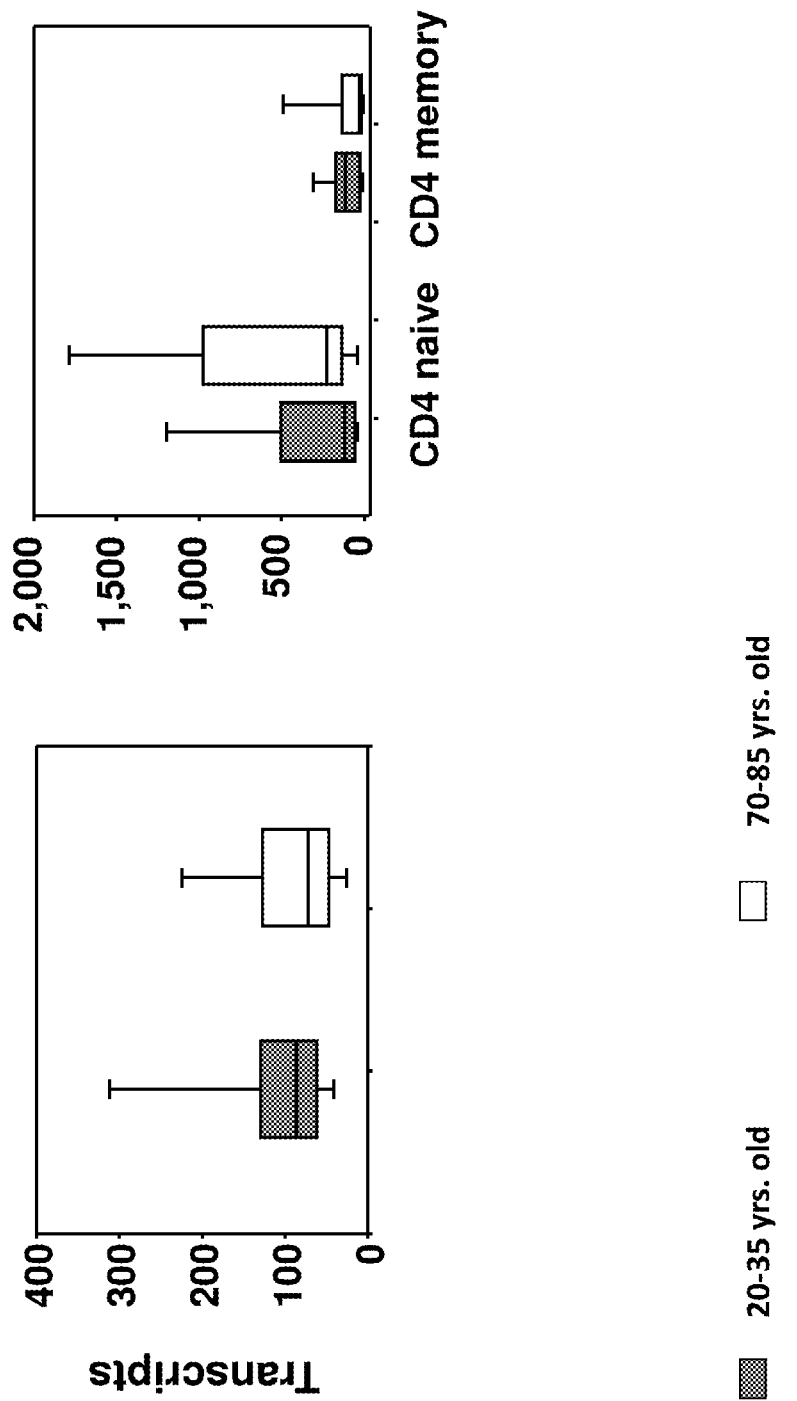

FIG. 4A illustrates a real-time PCR to check DUSP6 mRNA levels in total CD4 T cells (left panel, 20 young and 20 elderly) and naïve and memory CD4 T cells (right panel, 21 young and 15 elderly) in two age groups, in accordance with embodiments of the present invention and as further detailed in Example 4.

Figure 4B:
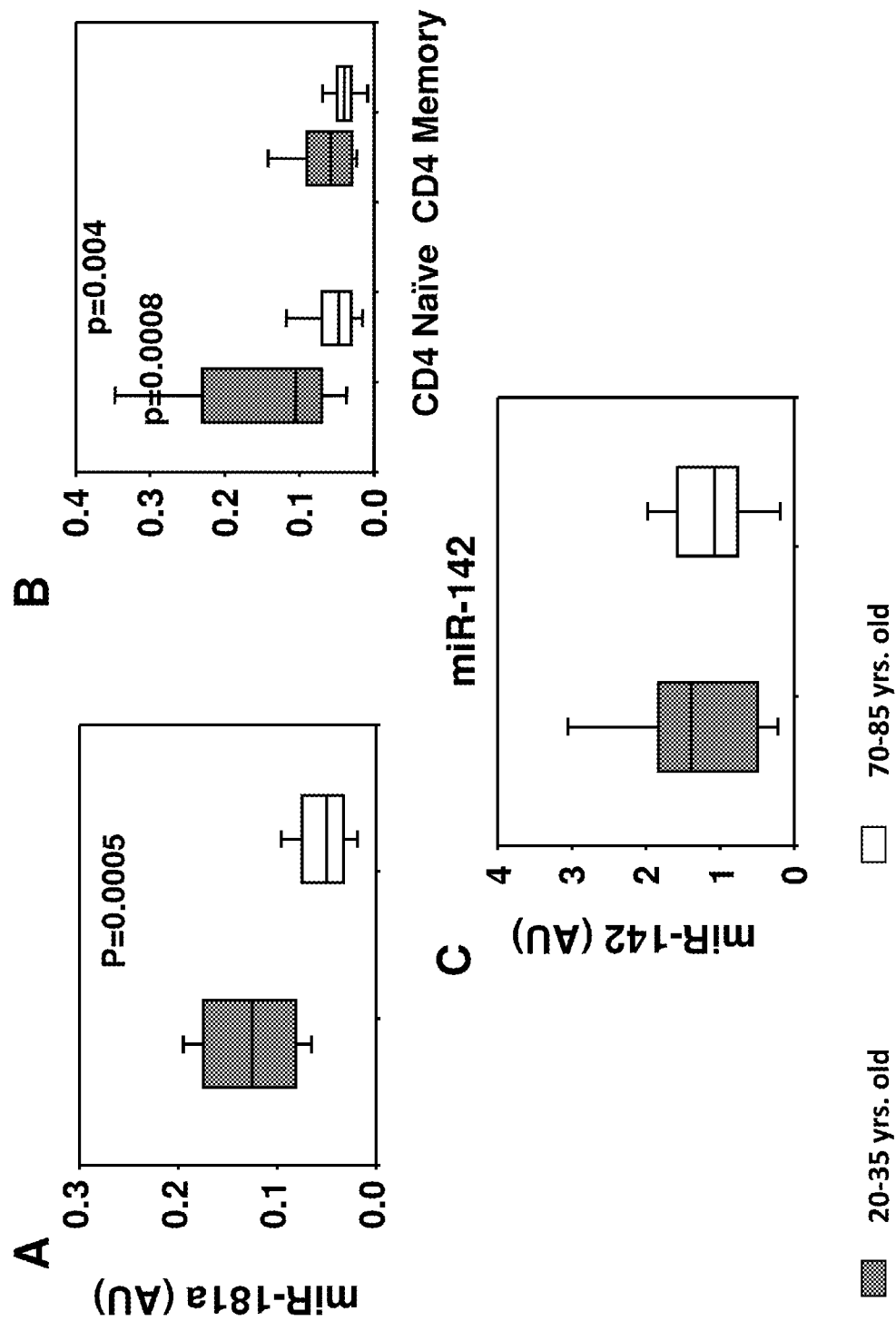

FIG. 4B illustrates miR-181a expression in T cells in two age groups, in accordance with embodiments of the present invention and as further detailed in Example 4. Panel A: miR-181a levels in CD4 cells, 21 young and 21 elderly. Panel B: miR-181a levels in CD4 naïve and memory T cells. 22 young and 16 elderly. Panel C: miR-142 levels in CD4 T cells. 21 young and 21 elderly.

Figure 4C:
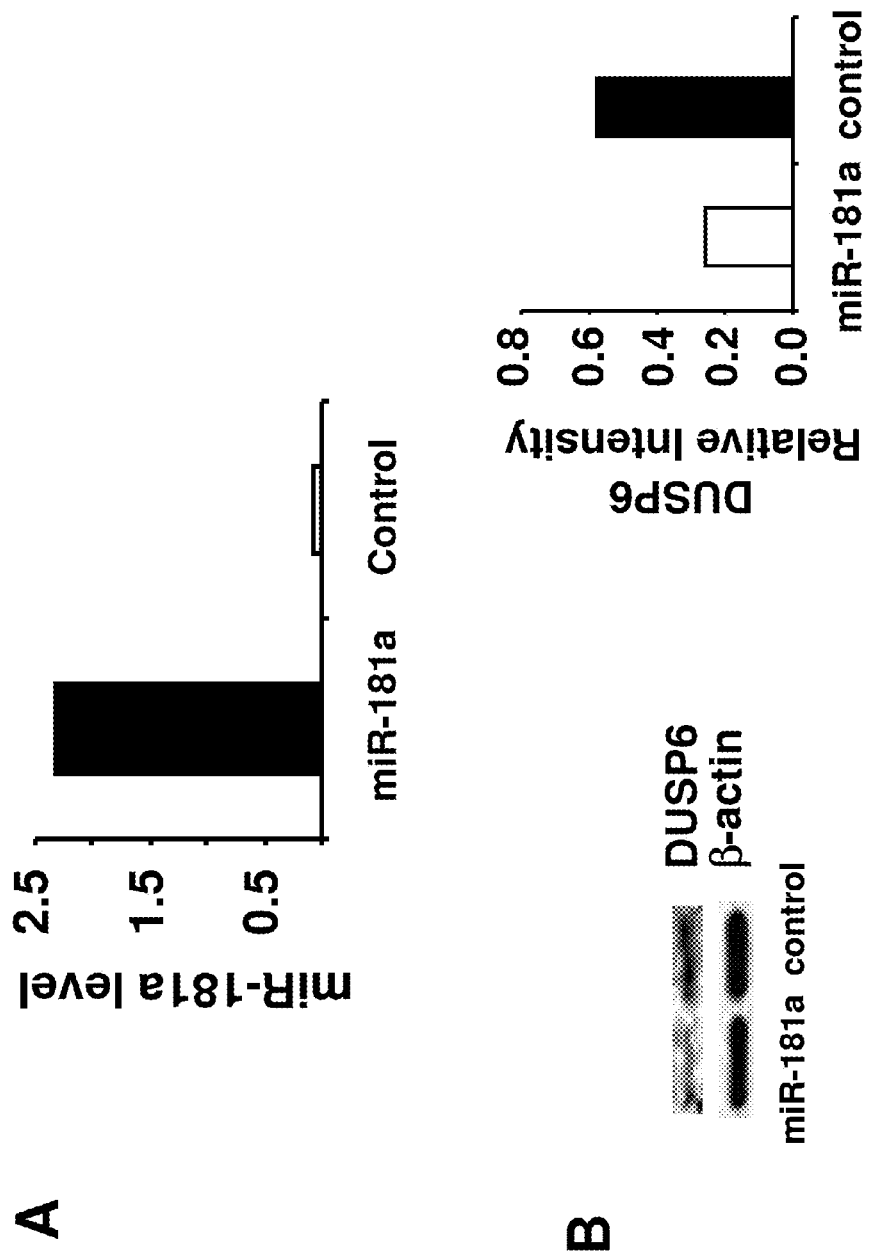

FIG. 4C illustrates overexpression of miR181a in T cells, in accordance with embodiments of the present invention and as further detailed in Example 4. Panel A: miR-181a levels after transfection. Panel B: DUSP6 levels after over expression of miR-181a.

Figure 5A:
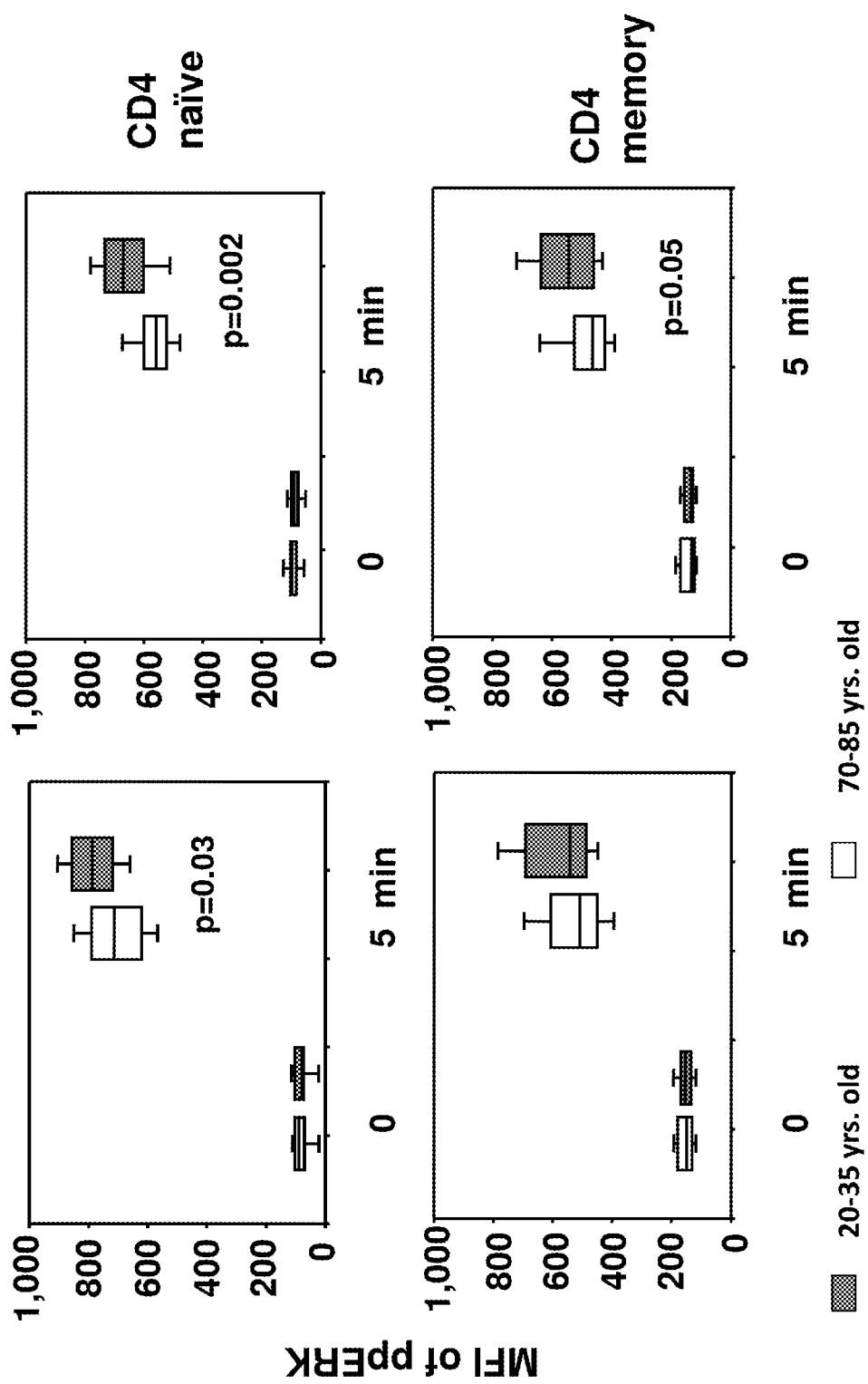

FIG. 5A illustrates ppErk levels in naïve and memory CD4 cells in two age groups (n=11 per group) after miR-181a overexpression, in accordance with embodiments of the present invention and as further detailed in Example 5.

Figure 5B:
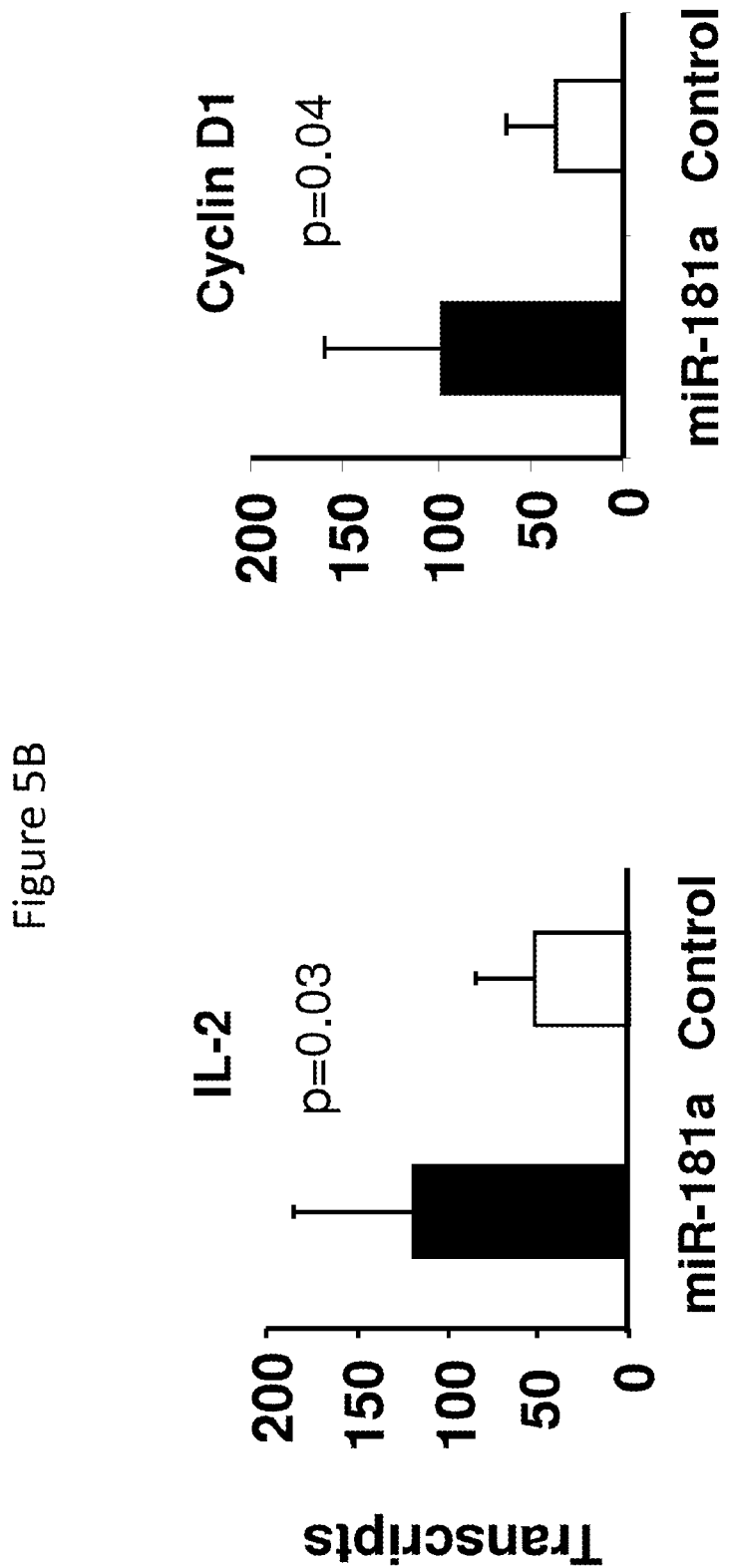

FIG. 5B illustrates FACS assay results of CD25 expression in CD4 naïve after miR-181a overexpression in the elderly (n=6), in accordance with embodiments of the present invention and as further detailed in Example 5.

Figure 5C:
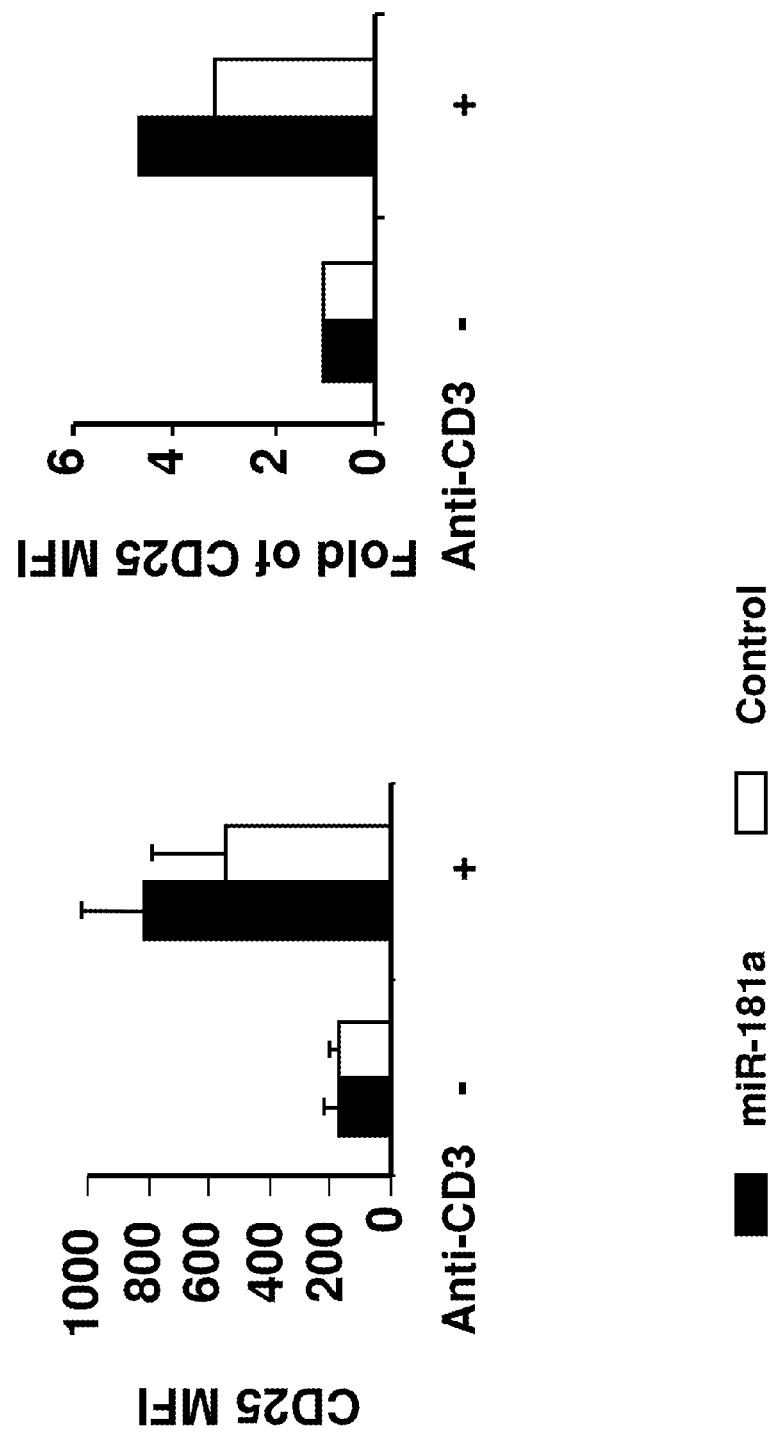

FIG. 5C illustrates real-time PCR assays of IL-2 and Cyclin D1 transcription in total T cells after miR-181a overexpression in the elderly (n=7), in accordance with embodiments of the present invention and as further detailed in Example 5.

FIG. 6 illustrates that activation-induced expression of the dual-specific phosphatase 4 in CD4 memory T cells increases with age, in accordance with embodiments of the present invention and as further detailed in Example 6. (Panel A) CD4 memory T cells from four 20-35 (open circles) and four 65-85 year-old healthy individuals (closed circles) were stimulated with toxic shock syndrome toxin 1 (TSST-1) and dendritic cells. Gene expression in stimulated Vb2+ T cells was arrayed at 16, 40 and 72 hours. Results are shown for one DUSP4 probe as mean±SEM. (Panel B) CD4 CD45RO⁻ naïve (upper panel) and CD4 CD45RA⁻ memory T cells (lower panel) were stimulated on anti-CD3/CD28 coated plates. Cells were harvested at indicated time points and DUSP4 transcripts were quantified by qPCR. Results are shown as mean±SEM of three 20-35 (open circles) and three 65-85 year-old healthy individuals (closed circles). (Panel C) CD4 memory T cells from eleven 20-35 (open bars) and thirteen 65-85 year-old healthy individuals (closed bars) were stimulated by CD3/CD28 cross-linking and analyzed, as described in Panel B. (Panel D) CD4 memory T cells from ten 20-35 (open bars) and ten 65-85 year-old healthy individuals (closed bars) were stimulated with TSST-1 and dendritic cells. DUSP4 transcripts were determined in isolated Vb2+ T cells. Results are shown as mean±SEM. (Panel E) Kinetics of DUSP4 expression in CD4 T cells was determined by Western blotting. (Panel F) DUSP4 expression in memory CD4 T cells at 48 hours after CD3/CD28 stimulation was compared. A representative Western blot for a young (Y) and elderly (0) individual is shown in the left panel. Relative densities of DUSP4 expression in memory CD4 T cells at 48 hours after stimulation are shown as mean±SEM of eight 20-35 (open bars) and eight 65-85 year-old healthy individuals (closed bars). (Panel G) CD4 memory T cells were stimulated on anti-CD3/anti-CD28 coated plates. Cells were harvested after 36 hours, transfected with reporter gene constructs using the DUSP4 promoter. Luciferase activity was assessed 12 hours after transfection in the absence (left) or presence of additional 4 hour stimulation with ionomycin and PMA (right). Results from five 20-35 (open bars) and five 65-85 year-old healthy individuals (closed bars) are shown as mean±SEM.

Figure 7A:
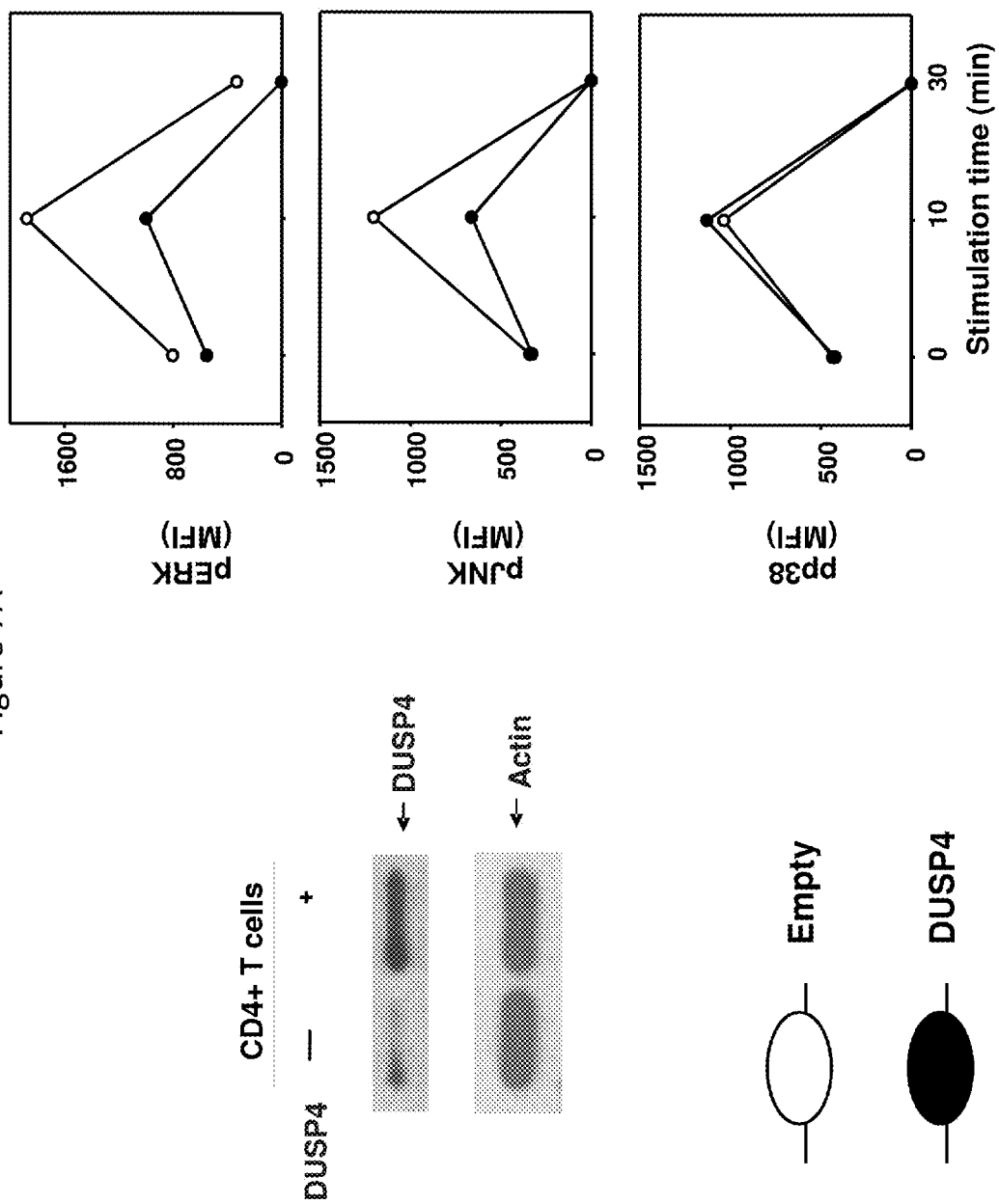
Figure 7B:
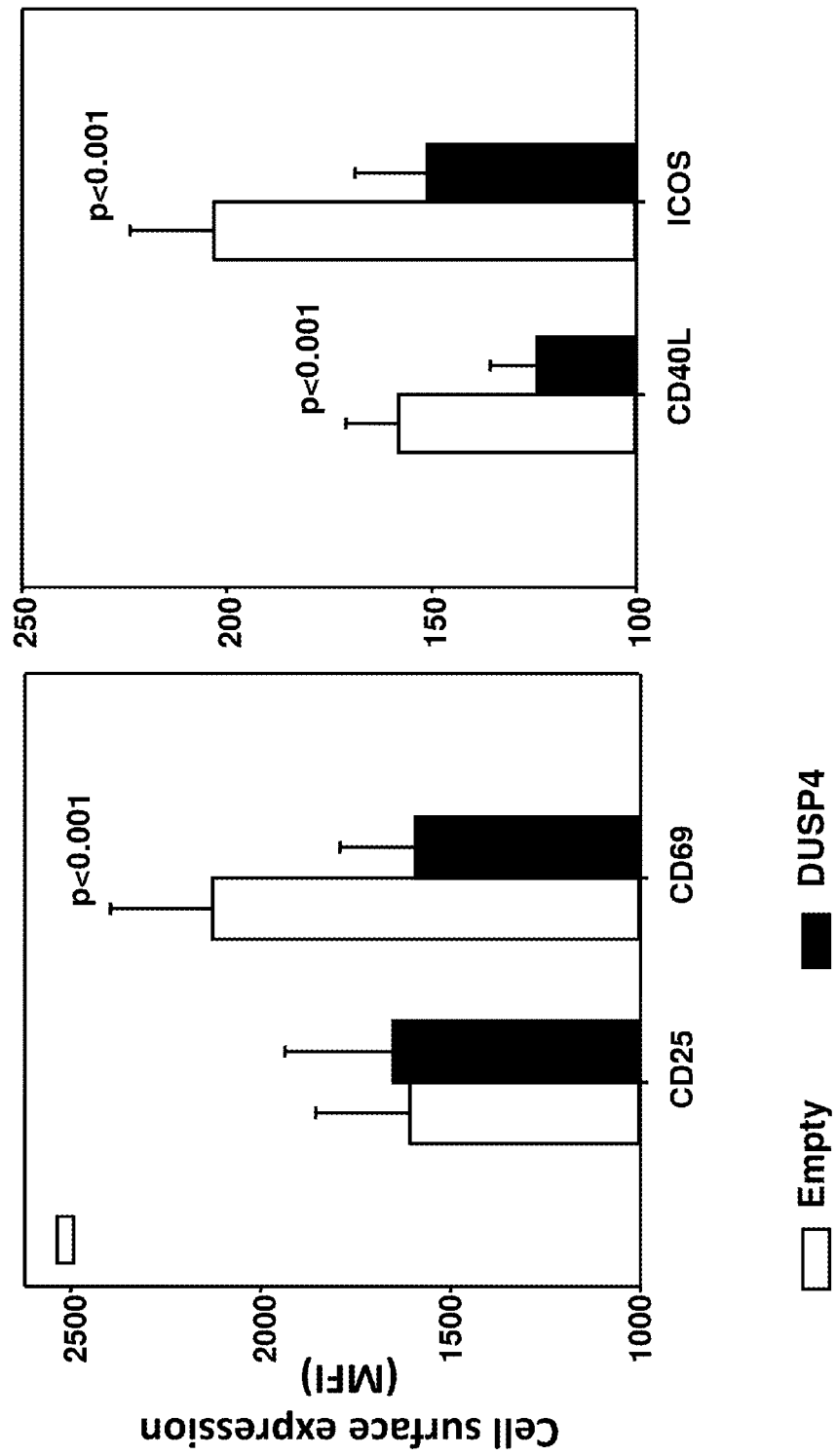
Figure 7C:
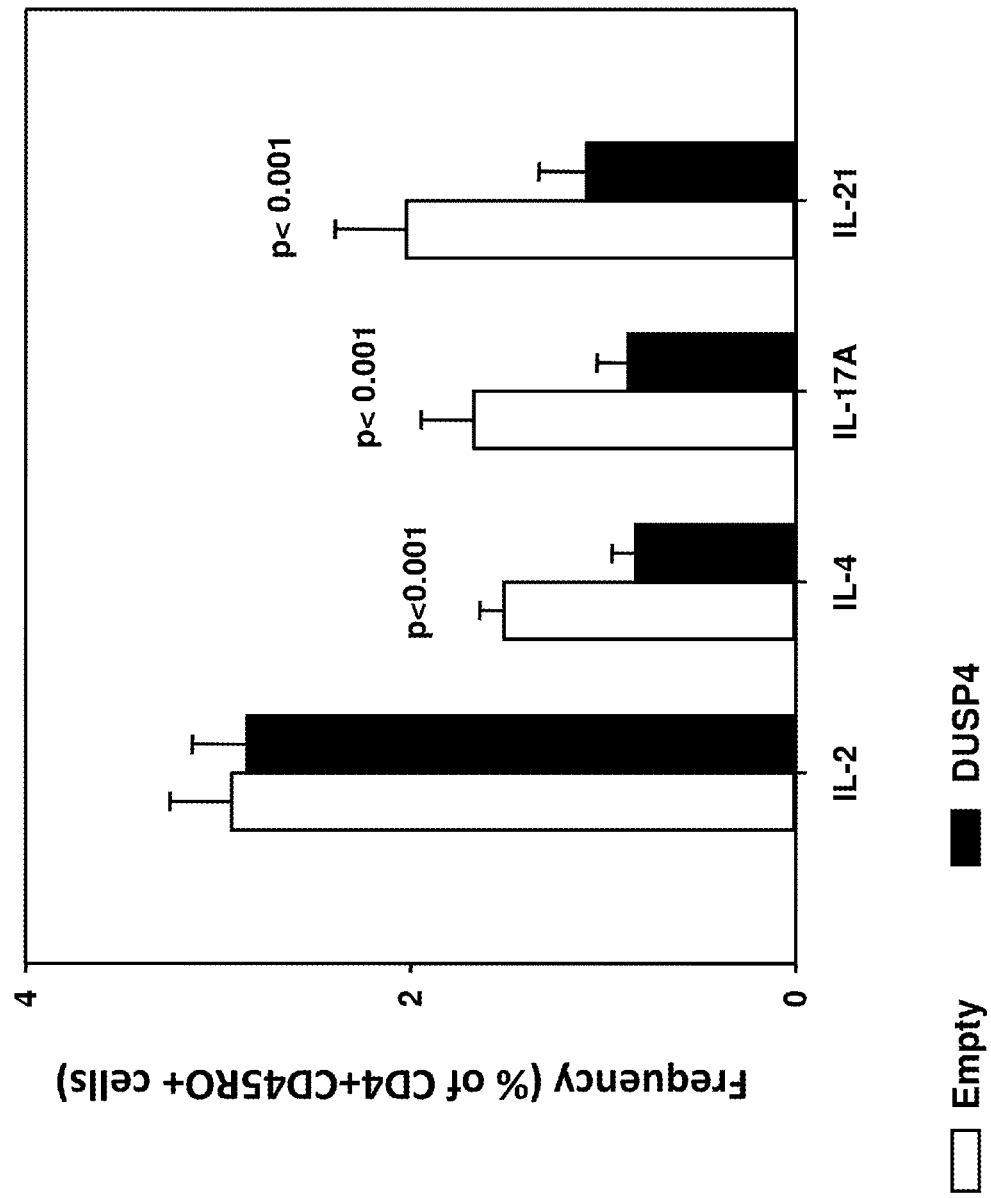

FIG. 7 illustrates that DUSP4 dampens CD4 memory T cell activation, in accordance with embodiments of the present invention and as further detailed in Example 7. (Panel A) CD4 T cells from healthy adults were transfected with a control or DUSP4-expressing vector. Cells were stimulated by anti-CD3 cross-linking and ERK, JNK and p38 phosphorylation was determined by Phosflow. One experiment representative of three is shown. (Panel B) CD4 T cells from young adult's PBMC were stimulated on plates coated with anti-CD3/CD28 antibodies for 36 hours and then transfected. 12 hours after transfection, DUSP4-transfected cells and control-transfected cells were assayed for the expression of activation markers. Results are expressed as mean±SEM MFI of nine to eleven experiments. (Panel C) Transfected cells were stimulated with PMA and ionomycin for four hours and cytoplasmic cytokine production was assessed. Results are expressed as mean±SEM of a minimum of ten experiments depending on the marker analyzed.

FIG. 8 illustrates that DUSP4 silencing improves T cell activity in the elderly, in accordance with embodiments of the present invention and as further detailed in Example 8. (Panel A) CD4 T cells were activated with plate-immobilized anti-CD3/CD28. Expression of activation markers was monitored by flow cytometry 48 (left) and 72 (right) hours after stimulation. Results from 20-35 (open bars) and 65-85 year-old healthy individuals (closed bars) are shown as mean±SEM of eleven to fourteen experiments depending on the marker analyzed. (Panel B) CD4 T cells were transfected with DUSP4 specific siRNA (open symbols) or control siRNA (closed symbols), stimulated by CD3/CD28 cross-linking for 48 hours and then restimulated by CD3 cross-linking. ERK, JNK and p38 phosphorylation was assessed by Phosflow before and 10 minutes after restimulation. Results with cells from an eighty year-old individual shown are representative of three experiments. (Panel C) CD4 T cells were transfected with siRNA and activated with plate-immobilized anti-CD3/CD28. Expression of activation markers after 72 hours is shown as the percent increase after DUSP4 silencing in eleven 20-35 (open bars) and eleven 65-85 year-old healthy individuals (closed bars). (Panel D) Cell cultures described in (Panel C) were restimulated on day 2 with ionomycin/PMA for 4 hours, and cytokine production was determined by flow cytometry. Results are shown as the percent increased in DUSP4-silenced CD4 memory T cells. (Panel E) IL-4 in supernatants from cultures as described in (Panel D) was measured by ELISA.

Figure 9A:
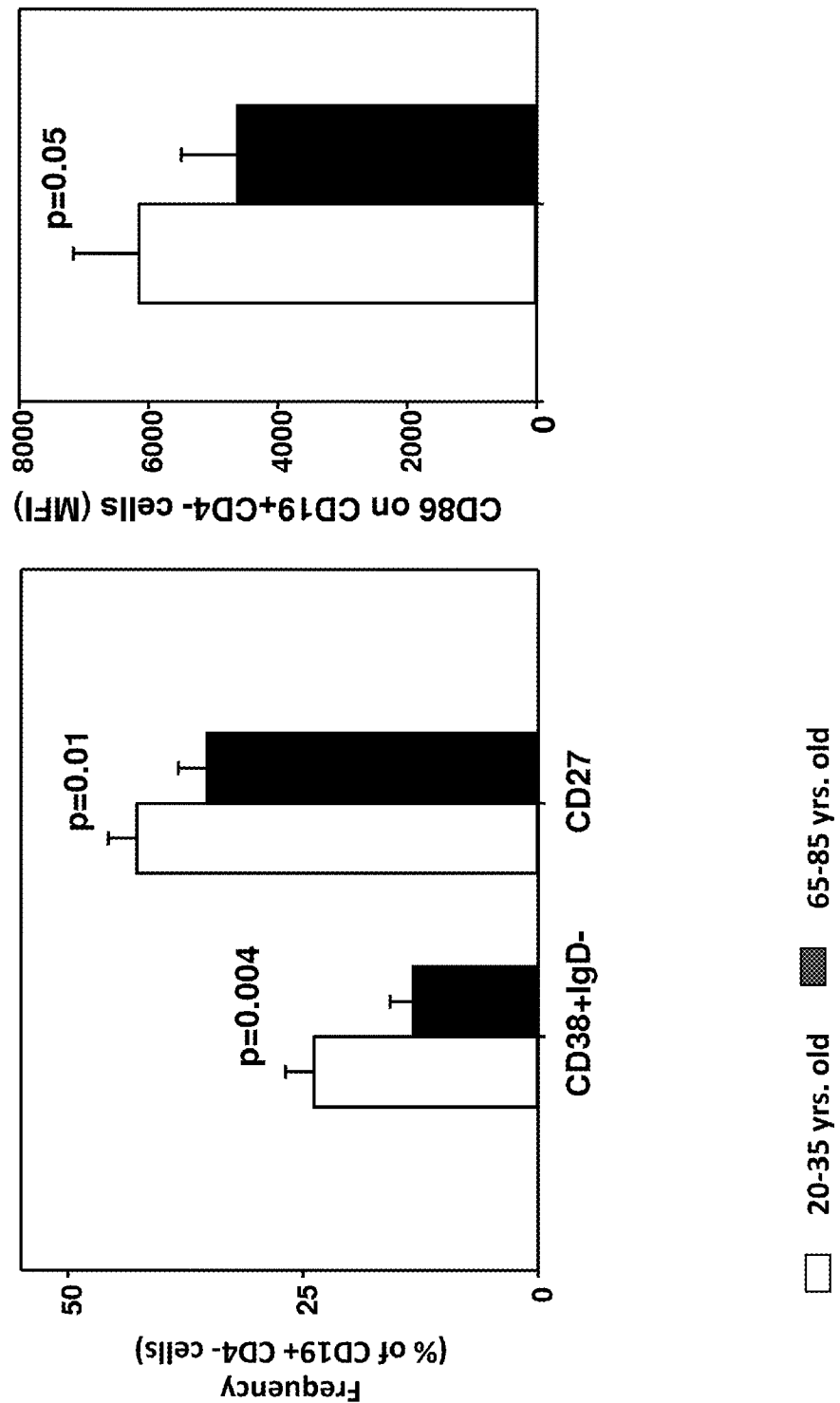
Figure 9C:
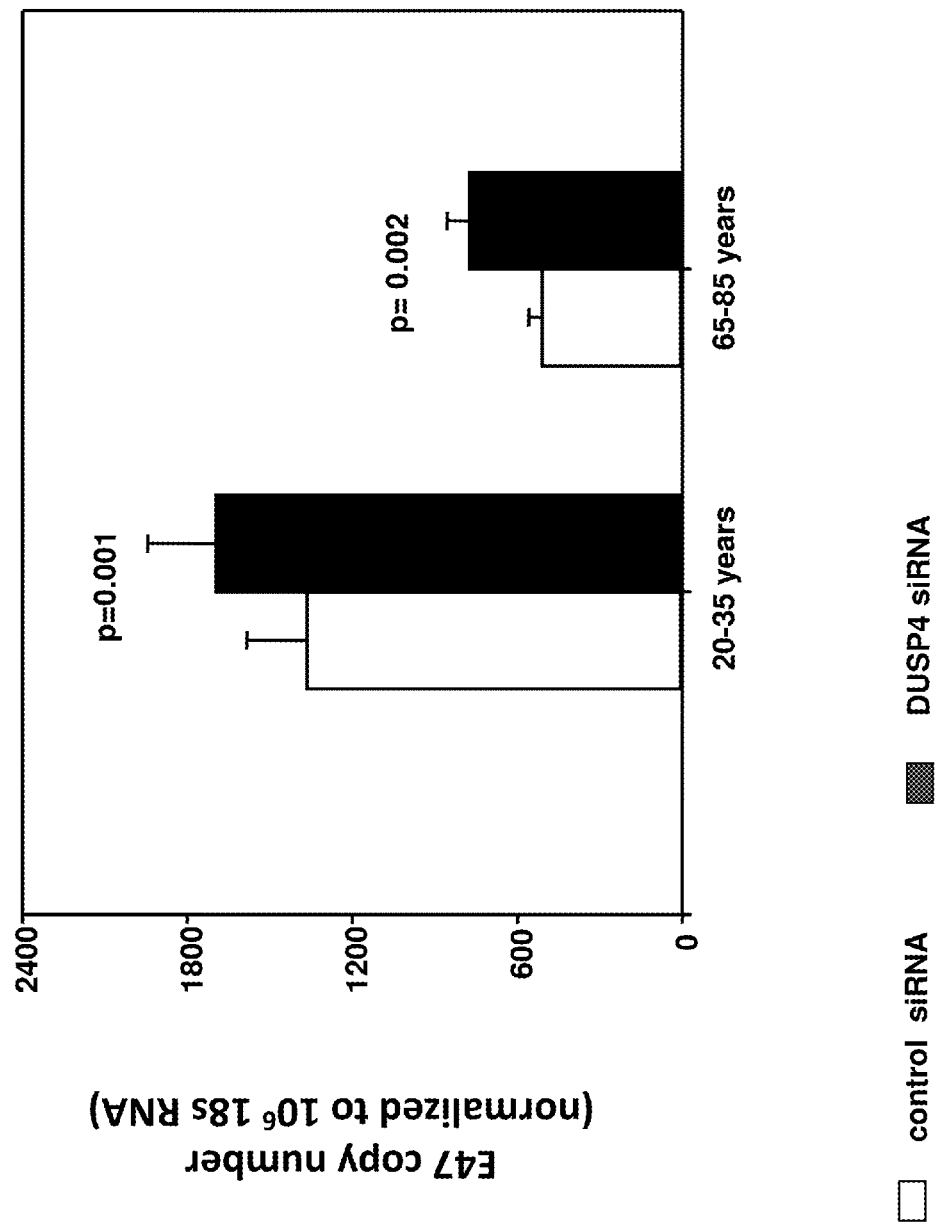

FIG. 9 illustrates that DUSP4 silencing in CD4 memory T cells improves T cell-dependent B cell responses, in accordance with embodiments of the present invention and as further detailed in Example 9. (Panel A) CD4 memory T cells from ten 20-35 (open bars) and ten 65-85 year-old healthy individuals (closed bars) were co-cultured with B cells from young healthy adults on anti-CD3/CD28 coated plates. Cultures were examined for the frequencies of CD19+CD38+ IgD- and CD19+CD27+ cells (left) and the expression of CD86 on CD19+B cells (right). (Panel B) CD4 memory T cells were transfected with DUSP4 or control siRNA and cultured as described in (Panel A). Results are expressed as percent increased in the frequencies of CD19+CD38+IgD- and CD19+CD27+ cells and the cell surface expression of CD86 in the cultures with DUSP4-silenced compared to control-transfected T cells. (Panel C) Cells cultured as described in (Panel B) were assessed for the transcription of the transcription factor E47 by qPCR.

Figure 10A:
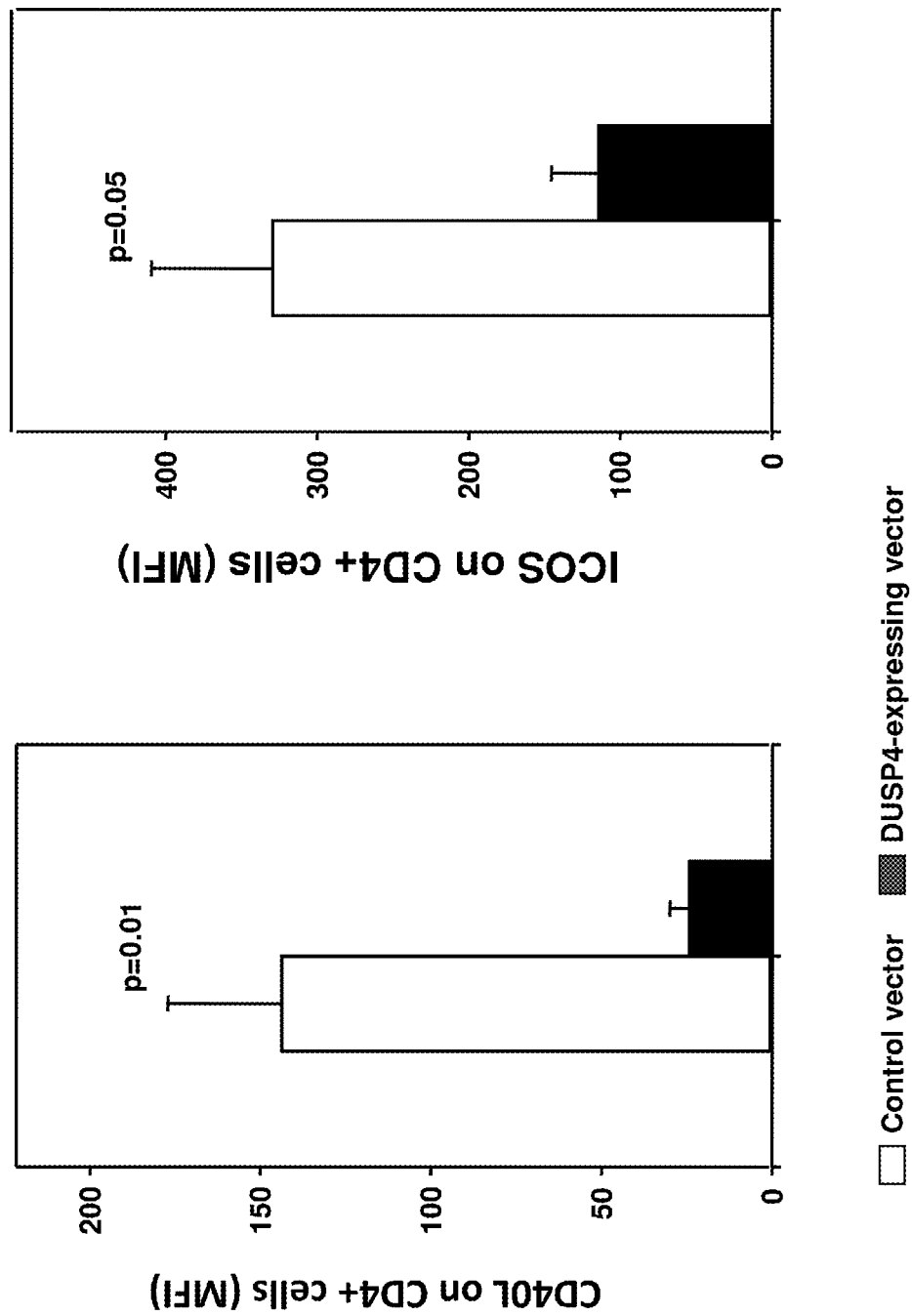
Figure 10B:
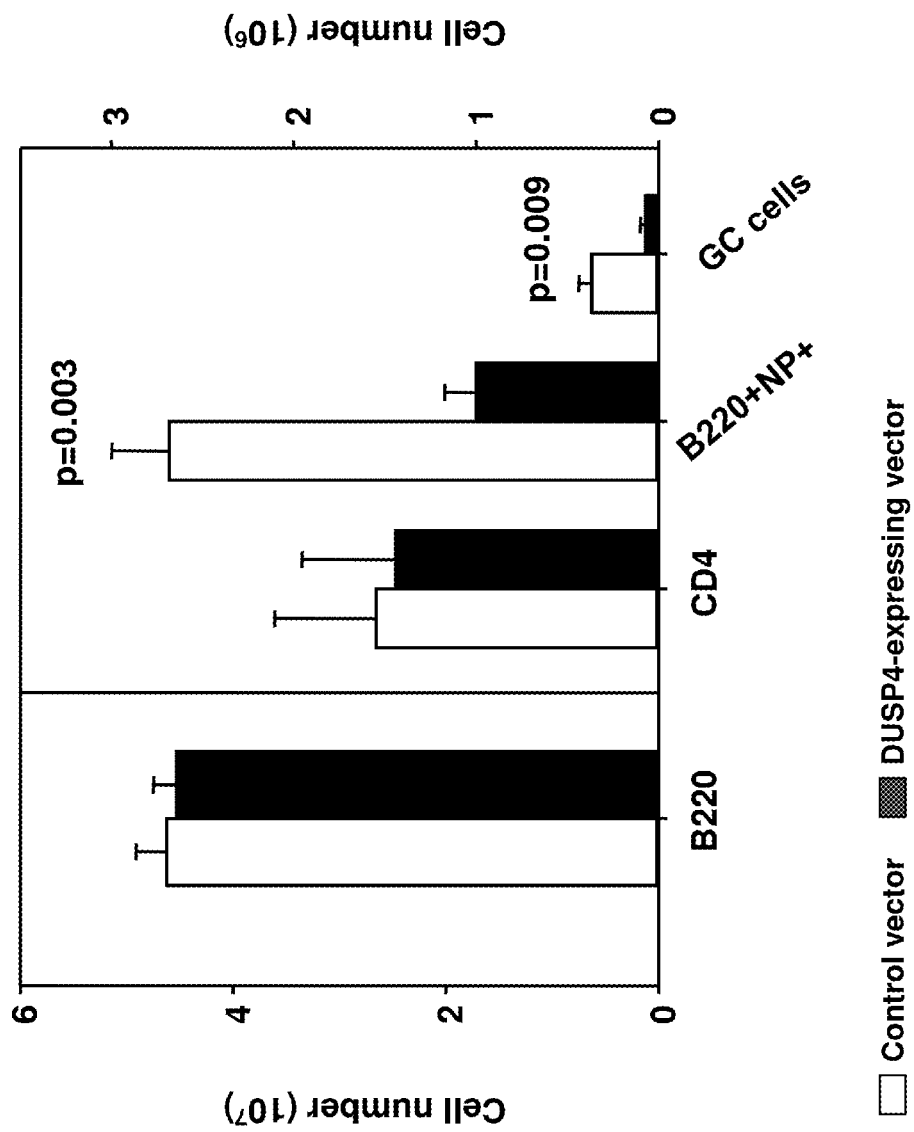

FIG. 10 illustrates that DUSP4 expression in T cells suppresses humoral responses after immunization in vivo, in accordance with embodiments of the present invention and as further detailed in Example 10. T cells from TCR transgenic (OT-II) were transduced with a DUSP4-expressing vector (solid bar) or a control retroviral vector (open bar) and adoptively transferred into CD4 knockout (B6.129S2-Cd4$^{tm1Mak}$/J) mice. Mice were immunized i.p with NP-ova, spleens and serums were harvested on day 14. (A) Expression of CD154 (CD40L) and CD278 (ICOS) was determined on splenic CD4 T cells by flow cytometry. Results are representative of two experimental series with 4 mice each and are shown as mean±SEM. (B) The total numbers of splenic CD4 T cells, B220 B cells, NP-specific B cells and NP-specific GC B cells in reconstituted and immunized mice were enumerated. (C) Ova-specific IgG were determined by ELISA.

DEFINITIONS

The practice of the present invention may employ conventional techniques of chemistry, molecular biology, recombinant DNA, microbiology, cell biology, immunology and biochemistry, which are within the capabilities of a person of ordinary skill in the art. Such techniques are fully explained in the literature. For definitions, terms of art and standard methods known in the art, see, for example, Sambrook and Russell 'Molecular Cloning: A Laboratory Manual', Cold Spring Harbor Laboratory Press (2001); 'Current Protocols in Molecular Biology', John Wiley & Sons (2007); William Paul 'Fundamental Immunology', Lippincott Williams & Wilkins (1999); M. J. Gait 'Oligonucleotide Synthesis: A Practical Approach', Oxford University Press (1984); R. Ian Freshney "Culture of Animal Cells: A Manual of Basic Technique', Wiley-Liss (2000); 'Current Protocols in Microbiology', John Wiley & Sons (2007); 'Current Protocols in Cell Biology', John Wiley & Sons (2007); Wilson & Walker 'Principles and Techniques of Practical Biochemistry', Cambridge University Press (2000); Roe, Crabtree, & Kahn 'DNA Isolation and Sequencing: Essential Techniques', John Wiley & Sons (1996); D. Lilley & Dahlberg 'Methods of Enzymology: DNA Structure Part A: Synthesis and Physical Analysis of DNA Methods in Enzymology', Academic Press (1992); Harlow & Lane 'Using Antibodies: A Laboratory Manual: Portable Protocol No. I', Cold Spring Harbor Laboratory Press (1999); Harlow & Lane 'Antibodies: A Laboratory Manual', Cold Spring Harbor Laboratory Press (1988); Roskams & Rodgers 'Lab Ref: A Handbook of Recipes, Reagents, and Other Reference Tools for Use at the Bench', Cold Spring Harbor Laboratory Press (2002). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable.

The term "activation", as used herein, refers to a physiological condition upon exposure to a substance, allergen, drug, protein, chemical, or other stimulus, or upon removal of a substance, allergen, drug, protein, chemical or other stimulus.

The terms "active immunization", "immunization, "active vaccination" and "vaccination", as used herein, are used interchangeably and refer to the acquisition of immunologic memory and long-term protection against recurring diseases through memory T cell development and antibody production in response to administration of an immunogenic antigen.

The term "vaccine", as used herein, refers to a biological preparation that contains antigenic or immunogenic material that resembles a disease-causing microorganism or cell and that might be made from an attenuated or inactivated form of said microorganism or cell or its toxins and that is administered to an individual in order to stimulate that individual's immune response to said microorganism or cell.

The term "antigen", as used herein, refers to any molecule that is recognized by the immune system and that can stimulate the production of antibodies and can combine specifically with them. The term "antigenic determinant" or "epitope", as used herein, refers to an antigenic site on a molecule.

The term "immunogen", as used herein, refers to any molecule that is recognized by the immune system and that is able to provoke a humoral and/or cell-mediated immune response.

The term "cytometry", as used herein, refers to a process in which physical and/or chemical characteristics of single cells, or by extension, of other biological or nonbiological particles in roughly the same size or stage, are measured. In flow cytometry, the measurements are made as the cells or particles pass through the measuring apparatus (flow cytometer) in a fluid stream. A cell sorter, or flow sorter, is a flow cytometer that uses electrical and/or mechanical means to divert and collect cells (or other small particles) with measured characteristics that fall within a user-selected range of values.

The term "expression", as used herein, refers to the action of a gene in the production of a protein or phenotype. "Levels of expression" or "expression levels" refer to the degree to which a particular gene produces its effect(s) in an organism.

The term "middle-aged individual", "individual of middle age" or "individual in middle age", as used herein, defines a human being who is between 35 and 65 years of age.

The term 'the elderly", "elderly individuals", "advanced-aged individuals", "individual of advanced age" or "individual in advanced age", as used herein, defines human beings older than 65 years of age.

The term"young adult", as used herein, defines a human between 18 and 35 years of age.

The term "immunocompromised", as used herein, refers to a state of decreased immune response in an individual, where the individual's ability to resist or fight off infections and tumors is impaired.

The terms "modulating activity or expression of at least one dual specificity phosphatase" and "modulator of activity or expression of a (or at least one) dual specificity phosphatase", as used herein, relate to biologically active, recombinant, isolated peptides and proteins, including their biologically active fragments, peptidomimetics and small molecules that are capable of inhibiting the enzymatic activity or gene expression of one or more dual specificity phosphatases.

The term "phosphoepitope", as used herein, refers to a phosphorylated protein on a cell surface or inside a cell. A comparison of phosphoepitopes can be used to determine the activation status of a cell or cell population as the measurement of phosphorylation of signaling intermediates may allow for association of network topologies with diseases states. For example, transduction signaling cascades involve transmembrane receptors that bind to a specific extracellular ligand, such as a hormone or a cytokine. This binding initiates the transduction of a signal by a cascade of intracellular enzymal events that ultimately results in degranulation, apoptosis, proliferation, migration, organization of the assembling of ribosomes, and/or gene transcription. These transduction cascades often proceed by sequentially adding or removing phosphate residues via phosphorylation or dephosphorylation to a series of enzymes in the cascade. Within the transduction signaling cascades, four components are important: (1) the transmembrane receptor and its specific ligand; (2) the kinases, i.e. phosphorylating enzymes that up- or down-regulate the activity of cascade enzymes; (3) phosphatases, i.e. dephosphorylating enzymes; and (4) the final acceptor of the cascade which performs the function(s) that the cascade triggers.

The term "therapeutic effect", as used herein, refers to a consequence of treatment that might intend either to bring remedy to an injury that already occurred or to prevent an injury before it occurs. A therapeutic effect may include, directly or indirectly, the reduction of infection or disease inflicted by pathogens.

The term "therapeutically effective amount" of a modulator of the activity or expression of a dual specificity phosphatase is an amount that is sufficient to provide a therapeutic effect in a mammal, including a human, for example, to achieve enhancement of a middle aged or advanced aged individual's immune response as a consequence of modulating the activity or expression of at least one dual specificity phosphatase. Such amount may be administered as a single dosage or according to a multi-day regimen to achieve the desired enhancement of immune response. Naturally, dosage levels of the particular modulator of the activity or expression of a dual specificity phosphatase employed to provide a therapeutically effective amount vary in dependence of the type of injury that is intended to treat or to prevent, the age, the weight, the gender, the medical condition of the mammal/human, the severity of the condition, the route of administration, and the particular modulator of the activity or expression of a dual specificity phosphatase employed. Therapeutically effective amounts of a modulator of the activity or expression of a dual specificity phosphatase might be estimated initially from cell culture and animal models. For example, $IC_{50}$ values determined in cell culture methods can serve as a starting point in animal models, while $IC_{50}$ values determined in animal models can be used to find a therapeutically effective dose in humans.

The term "recombinant", as used herein, relates to a protein or polypeptide that is obtained by expression of a recombinant polynucleotide.

The terms "isolated" and "purified" relate to molecules that have been manipulated to exist in a higher concentration or purer form than naturally occurring.

Routes of administration of modulators of the activity or expression of a dual specificity phosphatase or pharmaceutical compositions containing modulators of the activity or expression of a dual specificity phosphatase include, but are not limited to, oral as well as systemic administration; systemic administration includes intramuscular, subcutaneous, intravenous, intranasal or intraperitoneal administration. The modulator of the activity or expression of a dual specificity phosphatase or pharmaceutical compositions containing a modulator of the activity or expression of a dual specificity phosphatase may also be administered locally or topically or in a targeted delivery system including sustained release.

The term "pharmaceutical composition", as used herein, refers to a mixture of at least one modulator of the activity or expression of a dual specificity phosphatase with chemical components such as diluents or carriers that do not cause unacceptable adverse side effects and that do not prevent the modulator of the activity or expression of a dual specificity phosphatase from exerting a therapeutic effect. A pharmaceutical composition serves to facilitate the administration of a modulator of the activity or expression of a dual specificity phosphatase.

DETAILED DESCRIPTION

Embodiments of the present invention provide methods for restoring or enhancing T cell-mediated immune response in individuals of middle or advanced age by modulating an inhibiting force that negatively impacts T cell activation and/or differentiation into effective T helper cells.

Cells of the Immune System

White blood cells or leukocytes are cells of the immune system that defend the human body against infectious disease and foreign materials and are often characterized as granulocytes or agranulocytes, depending on the presence or absence of granules. There are various types of leukocytes, which are all produced in the bone marrow and derived from (multipotent) hematopoietic stem cells. Leukocytes are found throughout the body, including the blood and lymphatic system. Granulocytes encompass neutrophils, basophils, and eosinophils, while agranulocytes include lymphocytes, monocytes and macrophages.

B lymphocytes ("B cells") and T (thymus) lymphocytes ("T cells") constitute the two major classes of lymphocytes and play crucial roles in the immune response; hereby provide B cells a 'humoral' immune response through secreted antibodies, while T cells provide a cell-mediated immune response through the activation of various cells of the immune systems such as macrophages, natural killer cells and cytotoxic T cells.

B cells are precursors of antibody-secreting cells and, upon activation, differentiate either into antibody-secreting cells for a primary response via secreted antibodies upon a first exposure to an antigen or into memory B cells which provide a strong antibody response upon a second exposure to that same antigen.

T (thymus) lymphocytes or T cells constitute the second major class of lymphocytes and play a crucial role in the immune response, because they can function as (i) effector cells in cell-mediated responses, as (ii) helper cells in both humoral and cell-mediated immune responses or as (iii) regulatory cells. Typical functions of effector T cells are, for example, the lysis of pathogen-infected cells or the lysis of neoplastic cells, while typical functions of helper T cells are aiding in the production of specific antibodies by B cells; (immune)regulatory T cells, in contrast, are able to suppress immune responses.

T cells derive from precursors in the hematopoietic tissue, undergo differentiation in the thymus and, upon a special selection process in the thymus, become part of secondary lymphoid tissues. T cells that have not yet encountered an antigen or that have not yet been activated by an antigen, are called 'naïve' T cells. Following activation by an antigen, T cells are called 'antigen experienced'.

T cells can be distinguished from other lymphocytes, such as B cells and natural killer cells, by the presence of antigen-binding receptors on their cell surface, called T cell receptors (TCRs). CD4 T cells express the coreceptor molecule CD4 on their cell surface, while CD8 T cells express CD8. T cells require activation of tyrosine kinases following TCR ligation for maximal stimulation; however, the TCRs lack intrinsic tyrosine kinase activity and are dependent on cytoplasmic tyrosine kinases that localize to the TCR complex and initiate TRC-mediated signaling events (Clements et al., 1999).

CD4 T cells are the major helper cells of the immune system and assist other white blood cells in immunological processes, such as helping B cells mature into antibody-producing cells, recruiting granulocytes and activating cytotoxic T cells and macrophages. Helper CD4 T cells become activated when they are presented with peptide antigens (epitopes) by major histocompatibility complex (MHC) molecules that are expressed on the surface of antigen-presenting cells. Once activated, helper T cells divide rapidly and secrete cytokines (small proteins) that regulate and aid in the active immune response (Wan Y Y & Flavell R A, 2009). The activated helper T cells can then differentiate into one of several subtypes such as $T_{H1}$, $T_{H2}$, $T_{H3}$ and $T_{H17}$ (thou et al., 2009). T-cell responses to antigen depend, however, not only on the presentation of peptide/MHC complexes, but also on the availability of specific T-cell precursors. The human body has more than 100 billion T cells which form a very diverse repertoire of TCR, only a small fraction of which recognizes a given antigen. The frequency of antigen-specific TCR in the repertoire determines the likelihood that an antigen meets the appropriate T cell and is recognized (Naylor et al., 2005, Goronzy et al., 2007).

CD8 T cells can develop into cytotoxic T cells capable of efficiently lysing targets cells that express antigens that they have recognized, including virally infected cells and tumor cells (Parish & Kaech, 2009).

Memory T cells are a subset of antigen-specific T cells that persist long-term after an infection has resolved or following active immunization with an exogenous immunogen. They quickly expand to large numbers of effector T cells upon re-exposure to their cognate antigen and facilitate a secondary response, thus providing the immune system with "memory" against past infections. Memory T cells comprise two subtypes: central memory T cells ($T_{CM}$ cells) and effector memory T cells ($T_{EM}$ cells). Memory T cells may be either CD4 or CD8 T cells and typically express the cell surface protein CD45RO, while naïve T cells express CD45RA (Surh et al., 2006). The extent and quality of the secondary response through memory T cells depends on the extent to which naïve T cells are activated and differentiate.

Immunoregulatory T cells or suppressor T cells are crucial for the maintenance of immune tolerance. Their major role is to shut down T cell-mediated immunity toward the end of an immune reaction and to suppress auto-reactive T cells that escaped the selection process in the thymus. Two major classes of CD4 (immuno)regulatory T cells have been described, including the naturally occurring $T_{reg}$ cells and the adaptive $T_{reg}$ cells.

The Innate Immune System and Immune Response

Pathogens such as viruses cause an inflammatory reaction in the body through chemokine-mediated recruitment of leukocytes to the site of infection. Neutrophils are attracted first, followed by monocytes, macrophages, natural killer cells as well as other innate immune cells. Those innate immune cells then provide critical signals for dendritic cells that help to initiate a T cell-mediated, antigen-dependent or adaptive immune response (Janeway & Medzhitov, 2002).

T Cell-Mediated, Antigen-Dependent or Adaptive Immune Response

Secondary lymphoid tissues are the focal point of an adaptive immune response, because there naïve T cells are presented with and activated through physical contact with mature dendritic cells that present specific foreign antigen peptide/MHC complexes.

The transition from innate to adaptive phases of the immune response involves antigen uptake by antigen-presenting cells, particularly by dendritic cells. Dendritic cells support clonal expansion and differentiation of activated, antigen-specific T cells by providing proliferative information through foreign antigen peptide/MHC complexes and possibly through costimulatory ligands such as CD80 and CD86, which are ligands for CD28, an important cell-surface receptor on T cells that helps to initiate mitogenic signaling in naïve T cells.

After naïve helper T cells (CD4 T cells) have become activated and begin to divide and differentiate according to signals from dendritic cells and other co-stimulatory ligands, at least three subsets of effector CD4 T cells ($T_{H1}$, $T_{H2}$ and $T_{H17}$) emerge with specialized homing properties and functions in the adaptive immune response (Zhou et al., 2009).

One of the primary functions of antigen-experienced effector CD4 T cells is the establishment of an immune memory through a stable build-up of antigen-experienced B and T cells that have acquired specialized functional properties allowing them, upon repeated exposure to a particular antigen, to generate secondary responses that are more rapid and effective than those made by the initially activated T cells during the primary response. A stable build-up of antigen-experienced T cells is particularly important following active immunization or vaccination, when the production of antibodies for long-lasting protection against recurring diseases is desired.

Deteriorating Adaptive Immune Response in Middle-Aged to Advanced-Aged Individuals A declining regenerative capacity with age and inability to maintain a diverse repertoire and a balance between functional T-cell subsets with recurring or chronic infections over a lifetime has been held responsible for the deterioration of the adaptive immune response with increasing age.

Indeed, homeostasis of CD8 T cells is often not well maintained in older individuals, naïve and central memory CD8 T cells are being lost, while terminally differentiated effector T cells accumulate and clonal CD8 T-cell expansion dominate the repertoire. CD8 T-cell oligoclonality and senescence correlate with poor vaccine responses and general mortality and may account for the prolonged viremia that is seen in elderly patients infected with influenza (Messaoudi et al., 2004; Clambey et al., 2005).

In contrast, CD4 T cell homeostasis is much better maintained over life. In spite of thymic demise in mid adulthood, compartment sizes of naïve and central memory CD4 T cells are substantial, expansion of CD28-negative CD4 T-cell population is infrequent and usually related to disease. Nevertheless, adaptive immune responses that rely on CD4 T-cell function such production of antibodies after vaccination are being impaired with increasing age.

With increasing age, the ability of the immune system to protect against new antigenic challenges or to control chronic infections erodes (Weng, 2006, Targonski et al., 2007). More than 90% of all influenza-related deaths in the US occur in the elderly patients (Thompson et al., 2003; Hakim et al., 2007). Mortality and morbidity with newly arising infections is increased, and the response to active vaccinations declines (Nichol et al., 2007, Donahue et al., 1995). With increasing age, the ability of the immune system to respond to vaccination with an appropriate CD4 T cell response and the production of antibodies declines. Age is a confounding factor in vaccine responses even in the middle-aged adult. In a meta-analysis, any age older than 30 years represented a risk factor of having a decline in the antibody response to hepatitis B vaccine (Fisman et al., 2002).

The mechanisms underlying age-related defects in adaptive immune responses are multifactorial. Dendritic cell function important in antigen presentation and initiating T-cell responses to antigens does not appear to be majorly compromised by age. Declining thymic function has frequently been implicated; the thymus is most active early in life, but undergoes a steady decline in function over time and only has minute regenerative capacity after the age of 40 to 50 years (Nikolich-Zugich et al., 2004; Haynes et al., 2000; Douek et al., 1998). In spite of this thymic demise, declines in naïve CD4 T-cell compartment sizes are subtle, while CD8 T-cell homeostasis is less well maintained and effector cell population expand at the expense of naïve and central memory CD8 T cells (Naylor et al., 2005). The number of naïve CD4 T cells, although decreasing with age is still substantial up to the $8^{th}$ decade of life. Moreover, T cell receptor (TCR) diversity within the naïve CD4 T cell compartment in 60 to 65 year-old individuals is not different from that in 20 to 30 year-old individuals and only contracts later in life (Goronzy et al., 2007).

T cell-intrinsic functional defects may have a major role in the declining immune competence, in particular for CD4 T cells for which homeostatic control mechanisms appear to be very robust to dwindling thymic T cell generation and the cumulating antigenic challenges by repeated new or continuous chronic infections. In murine studies, an increasing lifespan of naïve CD4 T cells with age was important to maintain homeostasis but facilitated functional defects in individual cells. Age-related defects in murine CD4 T cells appear to predominantly involve the cytoskleteton signaling pathways. Functional and, in particular, signaling studies with human T cells have been difficult to interpret because of the confounding factors caused by different T-cell subset representation in a mixed peripheral blood lymphocyte population. A characteristic example is the accumulation of CD8 effector T cells with age that have reduced proliferative capacity and phenotypic changes such as CD28 loss and gain of immunoreceptor tyrosine-based inhibition motif (ITIM)-containing receptors that impact cell signaling (Weng et al., 2009).

Mitogen-Activated Protein Kinase (MAPK) Signaling Pathways

Mitogen-activated protein kinases (MAPKs) are important signal transducing serine/threonine protein kinases, unique to eukaryotes, that are involved in the regulation and control of gene expression, cell proliferation, cell motility and apoptosis. MAPKs are evolutionary conserved enzymes connecting cell-surface receptors to critical regulatory targets within mammalian cells. MAPKs also respond to chemical and physical stress, thereby controlling cell survival and adaptation (Liu et al., 2007, Kuida & Boucher, 2004).

Mammals express distinctly regulated groups of MAPKs (MAPK superfamily) such as extracellular signal-regulated kinases (ERKs), JUN N-terminal kinases (JNKs) and p38 proteins, all of which are activated by specific MAPK kinases (MAPKKs) through a cascade of phosphorylation events (Chang & Karin, 2001) and which play a role in T cell development, proliferation and differentiation (Jeffrey et al., 2007). These signaling cascades have been implicated not only in normal cellular processes, but also in the development of diseases including cancer, atherosclerosis, diabetes, arthritis and septic shock (Liu et al., 2007).

In T cells, extracellular signal-related kinases (ERKs) play an important role in initiating TCR-mediated signaling events, differentiating T cells and clonally expanding T cells (Teixeiro & Daniels, 2010).

Negative Regulation of MAPK Through MAPK Phosphatases or Dual Specificity Phosphatases (DUSPs)

Dual specificity phosphatases (DUSPs) are intracellular enzymes that catalyze the removal of phosphate groups from phosphotyrosine and phosphoserine/phosphothreonine residues within the same protein substrate (Patterson et al., 2007). While all DUSPs negatively regulate the MAP kinase superfamily, at least 13 different DUSPs display unique, but often overlapping substrate specificities for MAPKs (Salojin & Oravecz, 2007; Ducruet et al., 2005). For example, DUSP4, DUSP5 and DUSP6 are reportedly specific for ERK1 and ERK2 with a lesser effect on JNK and P38 pathways (Cao et al., 2010). Most DUSPs are inducible and demonstrate only low basal levels in nonstressed or unstimulated cells, only few DUSPs such as DUSP1 and DUSP6 are constitutively expressed.

Besides the MAP kinase superfamily, dual specificity phosphatases also regulate the cyclin-dependent kinases which play an important role in the regulation and control of cell cycle and which are dephosphorylated by members of the Cdc25 family.

Dual specificity phosphatases are suspected to play a role in cancer and selective dual specificity phosphatase inhibitors are being developed for target-based antineoplastic therapies (Vogt et al., 2003).

Dual Specificity Phosphatase 1 (DUSP1)

Dual specificity phosphatase 1 (DUSP1), which is located exclusively in the nucleus, constitutively expressed and rapidly inducible in various cells of the immune system including T cells and B cells, plays a role in both innate and adaptive immune responses via inactivation of p38 and JNK (Patterson et al., 2009; Salojin & Oravecz, 2007).

Synonyms for DUSP1 are MKP-1, CL100, hVH1, 3CH134 and PTPN10(erp); its GenBank accession number is NM_004417 (Ducruet et al., 2005).

Dual Specificity Phosphatase 4 (DUSP4)

Dual specificity phosphatase 4 (DUSP4), which is located exclusively in the nucleus, demonstrates low expression in resting or unstressed cells, but is rapidly induced in B cells, T cells and white blood cells following activation (Patterson et al., 2007; Liu et al., 2007; Salojin & Oravecz, 2007). Its substrate specificity is highest for ERK 1 and ERK 2, but has also an effect on JNK and P38 (Cao et al., 2010; Jeffrey et al., 2007).

Synonyms for DUSP4 are MKP-2, TYP, HVH2 and its GenBank accession number is NM_001394 (Ducruet et al., 2005).

Dual Specificity Phosphatase 5 (DUSP5)

Dual specificity phosphatase 5 (DUSP5) is, like DUSP4, exclusively located in the nucleus. Its substrate specificity is highest for ERK 1 and ERK 2 and, like DUSP4, it shows TCR-dependent inducibility in T cells upon stimulation.

A synonym for DUSP5 is HVH3 and its GenBank accession number is NM_004419 (Ducruet et al., 2005).

Dual Specificity Phosphatase 6 (DUSP6)

Dual specificity phosphatase 6 (DUSP6) is exclusively expressed in the cytosol and is one of the few DUSPs that is expressed constitutively, but still inducible following stimulation (Ducruet et al., 2005; Jeffrey et al., 2005). DUSP6, in particular, functions by dampening the initial activation-induced ERK phosphorylation after T cell receptor (TCR)-stimulation and, thus, raises the threshold for productive T-cell activation (Li et al., 2007).

Synonyms for DUSP6 are MKP-3 and PYST1; its GenBank accession number is NM_001946 (Ducruet et al., 2005).

Modulation of the Activity of DUSP1, DUSP4, DUSP5 and DUSP6

The enzymatic activity of the dual specificity phosphatases can be modulated in various ways such as by reversible or irreversible inhibition through a pharmacological agent, e.g., a small molecule, or by downregulation of gene expression.

Gene Downregulation Through Micro RNAs

One of the key posttranscriptional regulation mechanisms is microRNA (miRNA)-mediated gene downregulation. Through binding to partially complementary sites of target mRNAs, miRNAs negatively regulate target gene expression by inhibiting translation or degrading target mRNAs (Bartel, 2004; Davidson-Moncada et al., 2010). DUSP6 was found to be a target of miR-181a and downregulated by this miRNA in the murine T cells (Li et al., 2007).

miR-181a

Li et al., 2007, have shown that miR-181a plays a modulating role in TCR sensitivity and signaling strength. In murine studies, miR-181a has been found to function as a rheostat modulating TCR sensitivity and signal strength by inhibiting the protein expression of several phosphatases including dual specificity phosphatases 5 (DUSP5) and 6 (DUSP6), protein tyrosine phosphatase, non-receptor type 22 (PTPN22) and protein tyrosine phosphatase SHP-2.

In studies of the present invention, in human CD4 T cells, primarily an upregulation of DUSP6 in individuals of advanced age in comparison to individuals of young age was found. Consistent with this finding, overexpression of miR-181a in human T cells reduced DUSP6 protein levels without affecting PTPN22 or SHP-2 suggesting that species-specific sequence differences exist that influence miR-181a binding. Although the decrease in miR-181a in naïve CD4 T cells with increasing age might not only be restricted to DUSP6, the relative selectivity in humans for this one phosphatase involved in TCR threshold calibration raises the possibility that DUSP6 inhibition at the time of vaccination may significantly improve the immune response in individuals of middle and advanced age.

Utility of the Present Invention

Active immunization or vaccination is a cornerstone of preventive medicine to prevent an epidemic outbreak of infectious diseases and also to facilitate the eradication of neoplastic cells before they can take hold. Annual vaccinations against the highly variable influenza virus ('flu shots'), vaccinations against the H1N1 virus (swine influenza) or H1N5 virus (avian influenza) are typical examples of preventive medicine to protect against a flu pandemic. Although the elderly (usually defined as individuals aged 65 and above) are considered at risk of complications of influenza and annual influenza vaccinations are strongly recommended by the World Health Organization for this population group, currently only 20% of elderly respond to such vaccinations with a sufficiently strong, protective immune response, while the remaining 80% remain vulnerable to infections with influenza virus. This example underscores the observation that, with increasing age, the ability of the immune system to control chronic infections or to respond to vaccination with a protective CD4 T cell response and the production of antibodies declines.

Preventive cancer vaccines seek to prevent an individuals's infection with cancer-causing viruses, while therapeutic cancer vaccines seek to treat existing cancer. Examples of preventive cancer vaccines are human papillomavirus vaccines or hepatitis B vaccines against hepatitis B virus. Therapeutic cancer vaccines are being developed to treat various solid cancers of the lung, breast, prostate, colon, kidney, skin as well as blood cancers.

The extent and quality of the secondary, adaptive immune response through memory T cells depends on the extent to which naïve T cells are activated and differentiate. In middle to advanced aged individuals the T cell receptor (TCR) activation threshold is increased in naïve CD4 T cells compared to young individuals and, accordingly, early T cell activation events in naïve CD4 T cells are defective and followed by an incompetent and weak antigenic response. As a consequence, following active vaccination, middle to advanced aged individuals often don't develop a fully functioning adaptive immune response, as would be evidenced by a strong antibody production against an introduced immunogenic antigen, and, thus, do not obtain the benefits of long-lasting protection against recurring diseases (Haynes & Swain, 2006).

A defective T cell activation mechanism leads to a decreased production of memory T cells and, so, compromises the extent and quality of a secondary immune response upon reexposure to the introduced immunogen. A decreased production of memory effector T cells will lead to an impaired adaptive immune response upon reexposure, while a decreased production of memory helper T cells will cause an impaired humoral immune response.

The identification of T cell-intrinsic functional defects and the development of methods to overcome those may help in restoring and enhancing the adaptive immune competence as well as the humoral immune response in individuals, particularly in individuals of middle to advanced age. In studies that compared intrinsic functionality of naïve T cells in young adults and individuals of advanced-aged and that led to the present invention, naïve CD4 T cells in individuals of advanced age were found to have intrinsic functional defects particularly with respect to TCR sensitivity and signaling strength, when compared with naïve CD4 T cells in young adults.

Embodiments of the present invention describe methods to overcome those age-related intrinsic functional defects and, thus, to restore and/or enhance the immune response in the elderly by modulating, preferably pharmacologically inhibiting, DUSP1, DUSP4, DUSP5 or DUSP6 alone or by modulating, preferably pharmacologically inhibiting, combinations of DUSP1 and DUSP4; DUSP1 and DUSP5; DUSP1 and DUSP6; DUSP1, DUSP4 and DUSP5; DUSP1, DUSP4 and DUSP6; DUSP1, DUSP4, DUSP5 and DUSP6; DUSP4 and DUSP5; DUSP4 and DUSP6 before, directly at the time of active immunization and/or thereafter.

Methods to Restore or to Enhance T Cell-Mediated Immune Response in an Middle Aged or Advanced-Aged Individual by Modulating Dual Specific Phosphatases Separately or in Combination DUSP6 ALOND OR IN COMBINATION WITH DUSP5. Specific embodiments of the present invention address an age-related decline in miR-181a expression and associated increased protein levels of the dual-specific phosphatase DUSP6. In T cells, DUSP6 functions by dampening the initial activation-induced ERK phosphorylation after T cell receptor (TCR)-stimulation, raising the threshold for productive T-cell activation. Selective DUSP6 inhibition before, at the time of active vaccination and/or thereafter may improve T-cell mediated immune responses in middle to advanced aged individuals. This inverse expression pattern of DUSP6 and miR-181a suggests that the increased DUSP6 expression in CD4 naïve T cells of individuals of middle and advanced age may be caused by low miR-181a expression. Possible approaches to lower the threshold for productive T cell activation would be to modulate DUSP6—and possibly DUSP5—activity by either downregulating DUSP 6 expression, e.g. by using gene silencing methods, and/or by pharmacologically inhibiting DUSP6's activity, e.g. by using a small molecule inhibitor.

A further approach to lower the threshold for productive T cell activation would be to modulate miR-181a expression by upregulating miR-181a expression or to prevent the loss of miR-181a expression. Using one of these methods to lower the threshold for productive T cell activation at some time before, directly at the time of active immunization or vaccination or for several days thereafter promises to restore T cell activity and to restore as well as to enhance T cell mediated immune response.

DUSP6 plays, in the elderly, a critical role in the early activation step by regulating how many naïve T cells are activated. DUSP4, which is being expressed in memory CD4 T cells 24+ hours following activation, regulates then, in the elderly, how many of these memory CD4 T cells can indeed differentiate into helper CD4 T cells. Thus, from a temporal point of view, the action of DUSP6 directly precedes the action of DUSP4 and has a direct effect on the extent of the action of DUSP4. Therefore, a modulation of both DUSP4 and DUSP6 is contemplated in order to enhance the immune response in the elderly following immunization.

DUSP4 Alond or in Combination with DUSP6.

As shown in FIG. 6, DUSP4, which is only at low levels, if at all, expressed in resting or unstimulated cells, has been found, in comparison to young individuals, to be overinduced in memory CD4 T cells from elderly individuals following activation, which, in turn, prevents differentiation of such memory CD4 T cells into effective helper CD4 T cells upon reexposure to an immunogen (as seen in FIG. 7). Since one of the important functions of helper CD4 T cells is to help B cells differentiate into productive antibody-secreting cells, the reduced availability of helper CD4 T cells directly translates into a reduced antibody secretion and, as a consequence, an impaired immune response. This is of particular relevance when an immune response is sought through active immunization where reexposure to an immunogen is meant to achieve a protective CD4 T cell response.

As illustrated in Panel E of FIG. 6, expression of DUSP4 is noticeable after 24 hours or, more pronounced, after 48 hours following activation. Taking into account the time needed for induction, selective DUSP4 inhibition before, at the time of active vaccination and/or for several days thereafter is expected to improve the immune responses in middle to advanced aged individuals. In a preferred embodiment, a pharmacological inhibitor of DUSP4, for example a small molecule, might be administered to an elderly individual, before, at the time of active vaccination and/or for several days thereafter. Contemplating the use of an orally available small inhibitor of DUSP4, an effective amount of such oral inhibitor might be self-administered by the elderly individual at the time of vaccination as a single dosage or according to a multi-day regimen to achieve the desired enhancement of immune response.

In a preferred embodiment, a pharmaceutical composition of an inhibitor of DUSP6, for example a small molecule, might be administered in a therapeutically effective amount once or several times for a predetermined time period to an elderly individual, before, at the time of active vaccination and/or for several days thereafter. Within a similar time frame, a pharmaceutical composition of an inhibitor of DUSP4, for example a small molecule, might be additionally administered to an elderly individual, before, at the time of active vaccination and/or for several days thereafter. A pharmacological inhibitor which inhibits both DUSP4 and DUSP6 is considered in such a context as well. Contemplating the use of an orally available small inhibitor of DUSP6 and of an orally available small inhibitor of DUSP4, therapeutically effective amounts of such oral inhibitors might be self-administered by the elderly individual before and/or at the time of vaccination and for several days thereafter. Contemplating the use of an orally available small inhibitor of both DUSP6 and DUSP4, a therapeutically effective amount of such an oral inhibitor might be self-administered by the elderly individual before and/or at the time of vaccination as a single dosage or according to a multi-day regimen to achieve the desired enhancement or restoring of immune response.

A similar scenario is contemplated for the modulation of DUSP4 in addition to DUSP1 and/or DUSP5 with or without the modulation of DUSP6.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

Experimental Procedures

The following methods and materials were used in the examples that are described further below.

Cells

Peripheral blood for studies involving the modulation of expression of the dual specificity phosphatase 6 was obtained from 117 young (aged 20-35 years) and 80 elderly (aged 70-85 years) healthy individuals. Subjects with acute diseases, current or previous history of immune-mediated diseases or cancer except limited basal cell carcinoma, or chronic diseases that were not controlled on oral medications were excluded. The study was in accordance with the Declaration of Helsinki, approved by the Emory and Stanford Institutional Review Boards, and all participants gave informed consent. Peripheral blood mononuclear cells were isolated using lymphocyte separation medium. T-cell subpopulations were isolated by AutoMACS using microbeads coupled to specific antibodies (Miltenyi Biotec Inc). Total CD4 cells were positively isolated. To isolate naïve CD4 T cells from PBMC, memory T cells and CD14+ monocytes were depleted by anti-CD45RO and anti-CD14 magnetic microbeads. CD4 cells were then positively isolated. Memory CD4 T cells were isolated by depleting naïve T cells and CD14+ monocytes from PBMC with anti-CD45 RA and anti-CD14 magnetic microbeads, followed by positive isolation of CD4

T cells. In some experiments, naïve cells were isolated from CD4 T cells enriched by CD4+ T cell enrichment cocktail kit (StemCell Technologies, Vancouver, Canada) by positive selection with anti-CD45RA magnetic microbeads. Mature dendritic cells (mDCs) were generated from CD14-positive monocytes by culture with 800 U/ml GM-CSF and 1000 U/ml IL-4 (R&D System, Minneapolis, Minn.) for 6 days followed by stimulation with 1100 U/ml TNF-α (R&D System) and 1 μg/ml PGE2 (Sigma, St. Louis, Mo.) for 24-48 hours.

Peripheral blood for studies involving the modulation of expression of the dual specificity phosphatase 4 was obtained from 64 young (aged 20-35 years) and 52 elderly (aged 65-85 years) healthy individuals. Subjects with acute diseases, current or previous history of immune-mediated diseases or cancer except limited basal cell carcinoma or chronic diseases that were not controlled on oral medications were excluded. The study was in accordance with the Declaration of Helsinki, approved by the Emory and Stanford Institutional Review Boards, and all participants gave informed consent. Peripheral blood mononuclear cells (PBMC) were isolated using lymphocyte separation medium. T cell subpopulations and B cells were isolated by AutoMACS using magnetic beads coupled to specific antibodies (Miltenyi Biotec Inc). Total CD4 T or B cells were positively selected from PBMC with anti-CD4 or anti-CD19 beads. To isolate memory CD4 T cells from PBMC, naïve T cells and CD 14+ monocytes were depleted by anti-CD45RA and anti-CD14 beads. CD4 cells were then positively isolated.

T Cell—Dendritic Cells (DC) Co-Culture

Naive CD4 T cells were labeled with 5 μM Carboxy-fluorescein diacetate succinimidyl ester (CFSE; Molecular Probes, Eugene, Oreg.). $25 \times 10^3$ cells were co-cultured with $0.5 \times 10^3$ mDCs loaded with 0.04 ng/ml toxic shock syndrome toxin 1 (TSST-1, Toxin Technology, Sarasota, Fla.). Cell and TSST concentrations were optimized to minimize alloreactive and activate approximate 90% of Vβ2+ cells in young individuals to enter the cell cycle. Cells were harvested at 6, 12, 24, and 36 hours post activation and stained with anti-TCR Vβ2-FITC (Beckman Coulter, Brea, Calif.), anti-CD69 PE-Cy7, and anti-CD25-APC (all are from BD Biosciences). The frequency of CD69+ and CD25+ cells among Vβ2+ and Vβ2− CD4 naïve T cells was assessed on an LSR II flow cytometer (BD Biosciences). On day 4 after stimulation, CFSE dilution in Vβ2+ and Vβ2-CD4 naive T cells was determined. Data were analyzed using FlowJo (Tree Star, Inc. Ashland, Oreg.) and the fraction of Vβ2+ or Vβ2− CD4 naïve T cells that had entered the cell cycle and started dividing was determined.

Signaling Studies

ERK and ZAP70 phosphorylation levels were assayed by PhosFlow. Total T cells were negatively isolated by Human T Cell Enrichment Cocktail (StemCell Technologies, Vancouver, Canada). $0.5 \times 10^6$ T cells were stimulated with anti-CD3 (1 μg/mL) cross-linking or phorbol-12-myristate-13-acetate (PMA) (0.5 ng/mL) at 37° C., fixed in BD Cytofix buffer for 10 min at 37° C.; permeabilized by BD Perm Buffer III (for ERK) or II (for ZAP70), and stained with the following antibodies: anti-CD3-APC Cy7, anti-CD4-PerCP, anti-CD8-PE, anti-CD45RA-PE-Cy7, and Alexa Fluor 647-conjugated anti-phospho-ERK1/2 (pT202/pY204) or anti-phospho-ZAP70 (Y319/SykY352) (all were from BD Biosciences). Phosphorylation levels were analyzed on an LSR II flow cytometer (BD Biosciences) with FACSDiva software.

RNA Extraction, Reverse Transcription and Quantitative Reverse Transcription Polymerase Chain Reaction Total RNA from cells was isolated with Trizol reagent (Invitrogen) and cDNA templates were synthesized using AMV-Reverse Transcriptase (Roche) and random hexamer primers. To quantify transcription levels by SYBR quantitative reverse transcription polymerase chain reaction (qPCR) the following primers (all human sequences) were used: DUSP6: CAGTGGTGCTCTACGACGAG and GCAATG-CAGGGAGAACTCGGC; SHP-2: GAAGTGGAGAGAG-GAAAGAG and GTCCGAAAGTGGTATTGCCAGA; PTPN22: TTCTCTGTATCCTGTGAAGCTG and CTGT-CATCCTCTTGGTAACAACGT; β-actin: ATGGCCACG-GCTGCTTCCAGC and CATGGTGGTGCCGCCAGA-CAG (annealing temperatures all 58° C.); human DUSP4, TGGCAATAAGGACTCCGAATA and GGATCT-GTGGGTTTCATCACT with an annealing temperature of 55° C.; human E47, TGTGCCAACTGCACCTCAA and GGGATTCAGGTTCCGCTCTC with an annealing temperature of 55° C.; 18s ribosomal RNA, AGGGAATTC-CCGAGTAAGTGCG and GCCTCACTAAACCATCCAA with an annealing temperature of 63° C. The copy numbers were calculated using a standard curve. Transcripts numbers were normalized to β-actin transcripts, and results are given as relative transcript numbers.

Western Blotting

Purified total CD4, naïve CD4 and memory CD4 T cells were lysed in cell lysis buffer (20 mM Tris-HCl (pH 7.5), 150 mM NaCl, 1 mM Na$_2$EDTA, 1 mM EGTA, 1% Triton X-100, 2.5 mM sodium pyrophosphate, 1 mM beta-glycerophosphate, 1 mM Na$_3$VO$_4$ and protease inhibitors). Protease inhibitors were diluted according to the manufacturer's instructions (protease inhibitor mixture for mammalian cell extracts; Sigma-Aldrich). Lysates were cleared by centrifugation (12,000 g, 4° C., and 10 min) and the supernatants were boiled in SDS loading buffer. Same amounts of proteins were separated by electrophoresis on a 10% sodium dodecyl sulfate (SDS)-polyacrylamide gel and electroblotted to nitrocellulose membrane (Schleicher & Schuell Bioscience). After blocking with Tris-buffered saline/Tween 20/3% milk, the blots were probed with anti-DUSP6 (Santa Cruz Biotechnology), anti-PTPN22 (a kind gift from Dr. Andrew C. Chan, Genentech, Inc., South San Francisco, Calif.), anti-SHP-2 (Cell Signaling Technology, Inc.), anti-DUSP4 or anti-β-actin antibodies (Santa Cruz Biotechnology) and ECL reagent (Amersham Biosciences). Membranes were washed and developed with horseradish peroxidase-labeled secondary Ab (Santa Cruz Biotechnology) and Immobilon Western chemiluminescence detection system (Millipore). Band intensities were quantified with Quantity-one software (Bio-Rad Laboratories). Densities were expressed relative to β-actin.

Quantitation and Overexpression of miRNA

Total RNA was isolated using Trizol (Invitrogen) and miR-181a and miR-142 expression levels were assayed using a mirVana™ qRT-PCR miRNA Detection Kit (Applied Biosystems, Austin, Tex.) following manufacturer's instructions. Briefly, 25 ng of RNA from isolated T cells and Jurkat cells was reverse-transcribed in 10 μL at 37° C. for 30 min using a miRNA- or U6-specific oligonucleotide. miRNAs were then quantified by SYBR quantitative PCR in 25 ul with a condition of 95° C. for 3 min followed by 40 cycles of 95° C. for 30 sec, 60° C. for 30 s. Cycle threshold (CO values were recorded and the quantity of miRNA was calculated USING $2^{-\Delta\Delta Ct}$, where $\Delta\Delta Ct = (C_{t\ sample\ miRNA} - C_{t\ sample\ U6}) - (C_{t\ Jurkat\ miRNA} - C_{t\ Jurkat\ U6})$. To over express miR181a, total T cells were transfected with miR-181a precursor or negative control (Applied Biosystems) using Nucleofector Kit (Amaxa, Germany). 40 to 48 hours after transfection, the cells were harvested and assayed.

Cell Culture, Transient Transfection and Luciferase Assay

Purified memory CD4 T cells from young or elderly healthy individuals were cultured in plates coated with anti-CD3/CD28 antibodies for 36 hours. Cells were harvested and transfected with 0.5 µg TK-pRL control vector plus 4.5 µg pGL3 basic vector or 0.5 µg TK-pRL control vector plus 4.5 µg DUSP4-luc reporter vector (provided by Dr. Roberson, Cornell University). Transfected cells were either left unstimulated or were restimulated after 12 hours with ionomycin/PMA for 4 hours. Luciferase activity was determined 16 hours after transfection using Dual-Luciferase reporter assay kits (Promega).

DUSP4 Transient Transfection

Purified CD4 T cells were transfected with 4 µg pCDNA3.1-DUSP4 (provided by Dr. Yin Columbia University) with the Amaxa Nucleofector system and the Human T cell Nucleofector kit (Amaxa). 24 hours later, phosphorylation levels of MAP kinases were analyzed by phospho-specific flow cytometry. Alternatively, purified CD4 T cells from young healthy adults were stimulated in plates coated with anti-CD3/CD28 antibodies for 36 hours. Activated cells were transfected with 2 µg DUSP4-pIRES2-AcGFP1 or with 2 µg pIRES2-AcGFP1 empty vector (Clontech). Expression of activation-induced cell surface markers or cytoplasmic cytokines were determined by flow cytometry after 12 hour culture in medium after transfection.

Flow Cytometry

Antibodies used for human CD marker staining included FITC-anti-IgD, PerCP-anti-CD4, APC-anti-CD19, FITC or PE-anti-CD25, PE-anti-CD27, PE or APC-anti-CD45RO, PE/Cy7 or PE-anti-CD69 and PE-anti-CD86 (BD Biosciences); PE/Cy7-anti-CD38, PE-anti-CD154 (CD40L) and FITC or PE-anti-CD278 (ICOS) (eBioscience). For intracellular cytokine staining, FITC-anti-IFN-gamma, FITC-anti-IL-2, PE-anti-IL-4 and PE-anti-IL-21 (BD), and Alexa Fluor 647-anti-IL-17A (eBioscience) were used. The cells were permeabilized with BD Cytofix/Cytoperm Kit (BD Biosciences). Phospho-specific flow cytometry: $1 \times 10^6$ transfected CD4 T cells were stimulated with anti-CD3/CD28 mAb (1 µg/ml each) cross-linking, and then fixed with 2% formaldehyde for 10 min at room temperature. After permeabilized in 100% methanol at −20° C. overnight, intracellular stains consisted of one of the following phospho-specific antibodies: phospho-ERK1/2, phospho-JNK and phospho-p38 (Cell Signaling Technology). All staining cells were harvested by an LSR II system (BD Biosciences), and data were analyzed using FlowJo software (Tree Star, Inc. Ashland, Oreg.)

RNA Interference

Total CD4 or memory CD4 T cells were transfected with 1.5 µg of siRNA specific for human DUSP4 (siGENOME SMARTpool, Dharmacon) using the Amaxa Nucleofector system and the Human T cell Nucleofector kit (Amaxa). As control AllStars Negative Control siRNA (Qiagen) was used. 12 hours after transfection, cell numbers were adjusted, and cells were stimulated with anti-CD3/CD28 coated plates. Knockdown efficiencies were monitored by qPCR and Western blotting.

ELISA

Supernatants from 48 hour cultures of $1 \times 10^6$/ml CD4 T cells stimulated on anti-CD3/CD28 coated plates were examined for the production of IL-4 using human IL-4 ELISA Ready-SET-Go kit (eBioscience).

In Vitro T Cell Help for B Cell Differentiation

Memory CD4 T cells were transfected with specific or control siRNA to silence DUSP4 induction. 12 hours after siRNA transfection, T cells were treated with 30 µg/ml mitomycin C (Sigma-Aldrich) for 30 min at 37° C. Cells were washed with medium three times. $1 \times 10^5$ T cells were co-cultured with $0.5 \times 10^5$ B cells purified from PBMC of unrelated healthy adults in culture plates coated with anti-CD3 antibody for 7 days. Culture in non-coated plates served as controls.

Animal Model

Animals

TCR transgenic (OT-II) and CD4 knockout (B6.12952-Cd4tm1Mak/J) mice were obtained from the Jackson Laboratory and housed in the animal facility of Emory University or VA Palo Alto. The experimental protocol was approved by the Emory and the VA Palo Alto Institutional Animal Care and Use Committee.

Retroviral Vectors, CD4 T Cell Isolation, Adoptive Transfer

Mouse DUSP4 cDNA was purchased from Open Biosystems (Clone ID is 40092218). The entire open reading frame was subcloned into the retroviral expression vector MSCV PIG (Puro IRES GFP, Addgene). Total CD4 T cells were isolated from the OT-II mouse spleen by negative selection (Miltenyi Biotec Inc), stimulated with 2 µg/ml concanavalin A (ConA) and 100 U/ml IL-2 for 48 hours and then cultured with retroviral supernatant produced by the Phoenix-ECO cell line (ATCC). 48 hours after infection, the cells were transferred into fresh complete RPMI 1640 media with 20 U/ml IL-2 for an additional 48 hour puromycin selection. Transfection efficiency was monitored using flow cytometry.

DUSP4 overexpressing CD4 T cells ($2 \times 10^6$/mouse) were intravenously injected into CD4 knockout (B6.129S2-Cd4tm1Mak/J) hosts. Control hosts received empty vector-transduced CD4 T cells. One day later, mice were immunized i.p. with 150 µg NP-OVA (Biosearch Technologies) in PBS with alum. Mice were reimmunized on day 12. Splenocytes and serum were collected 2 days after re-immunization. Two experimental series were performed, each of them with four hosts in each treatment group Flow Cytometric Analysis of Murine Experiments Membranes were washed and developed with horseradish peroxidase-labeled secondary Ab (Santa Cruz Biotechnology) and Immobilon Western chemiluminescence detection system (Millipore). Single cell suspensions of spleen from immunized host mice were harvested at the indicated time points. Antibodies for the following cell surface antigens were used: PE-CD4, APC-CD62L, APC-CD154 (CD40L), PE-B220 and APC-streptavidin (eBioscience); Alexa Fluor 647-CD278 (ICOS), PerCP/Cy5.5-CD150 (SLAM) and PE/Cy7-CD38 (BioLegend); PerCP-B220, PerCP/Cy5.5-CD44 and PE/Cy7-CXCR5 (BD Pharmingen), as well as Biotin-peanut agglutinin (PNA) and NP-PE (Vector Laboratories and Biosearch Technologies, respectively). Flow cytometry was performed using a LSRII flow cytometer (BD); data were analyzed using Flowjo software.

Detection of NP-Specific Antibody

NP-specific IgG was quantified by mouse IgG ELISA quantitation kit (Bethyl Laboratories) using NP-OVA (10 µg/ml) as the capture antigen.

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1

Age-Related Decreased Sensitivity to Antigen-Induced T Cell Activation

Decline in cell number as well as cell intrinsic defects such as defects in cell activation and cytokine production, contribute to impaired naïve CD4 T cell responses in the elderly. The frequency of naïve CD4 T cells significantly changes with age, however, this decline cannot fully explain the defective T cell response suggesting that either the environment in the aging host is not supportive or that T cell intrinsic defects accumulate with aging.

To define an influence of age on antigenic response of human naïve CD4 T cells, cell cycle entry was examined using a T cell-dendritic cells co-culture system in which CD4 naïve T-cells were stimulated with superantigen TSST-1 loaded dendritic cells (DCs). DCs were generated from monocytes of healthy young individuals to minimize putative aging effects. The system allows to examine separately high and low functional avidity human T cell responses in the same culture (Lee et al., 2007; Langenkamp et al., 2002), and minimize allogeneic primary T cell response (data not shown).

Figure 1A:
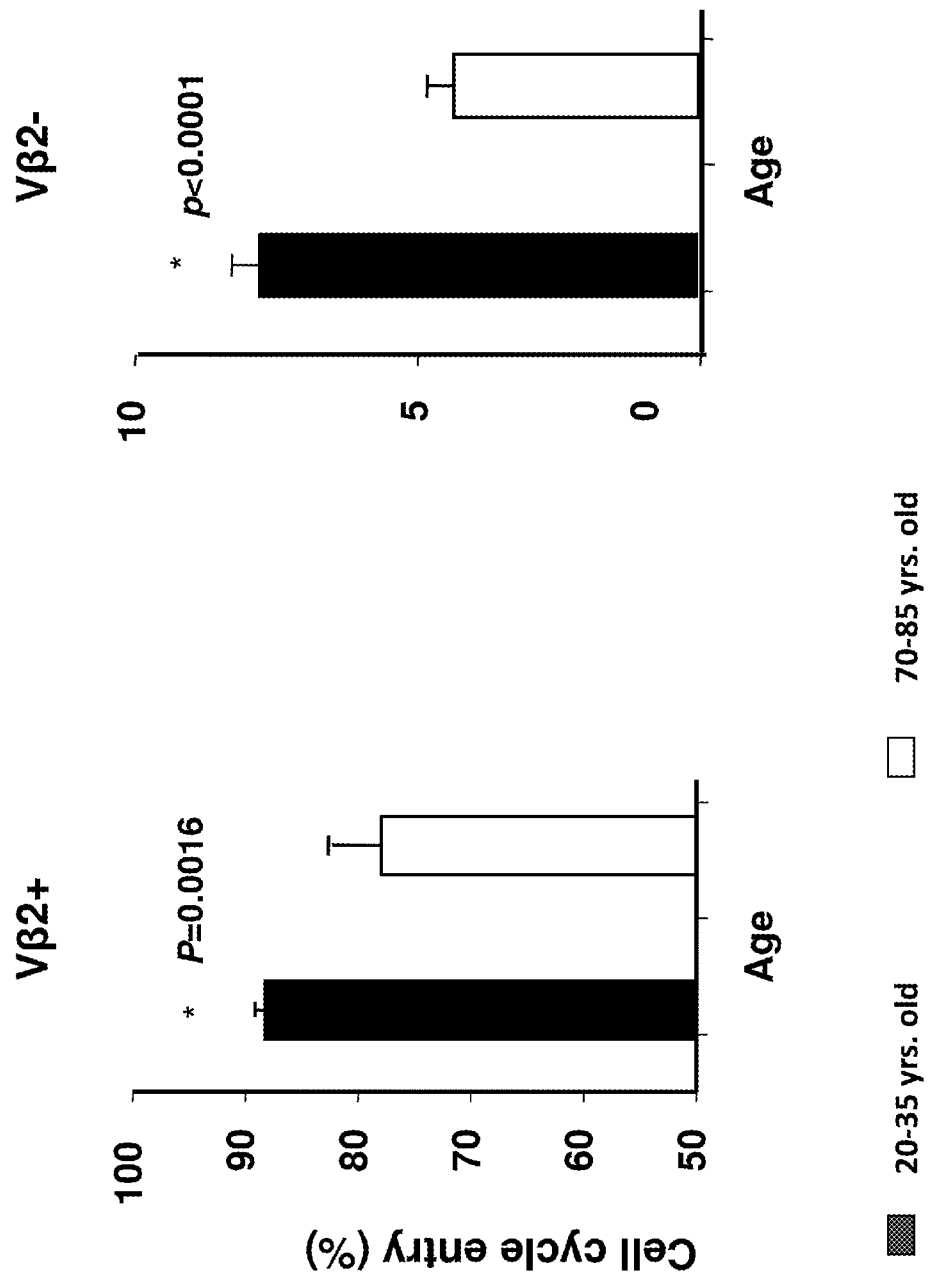

We probed T cell function by stimulating purified naïve CD4 T cells from thirty-five 20-35 year old and seventeen 70-85 year old individuals with the superantigen TSST presented by myeloid dendritic cells from young adults. To focus on early T cell activation events, we examined the frequency of T cells that entered the cell cycle and divided at least once after stimulation. A significantly lower number of naïve CD4 T cells responded to stimulation in the elderly individuals (FIG. 1A). The difference was more pronounced for Vβ2-negative naïve CD4 T cells ($p<0.0001$) that recognize TSST with low affinity than for high affinity Vβ2-positive cells ($p=0.0016$) consistent with the notion that the T cell receptor (TCR) activation threshold is increased in naïve CD4 T cells from elderly individuals compared to young individuals.

Figure 1B:
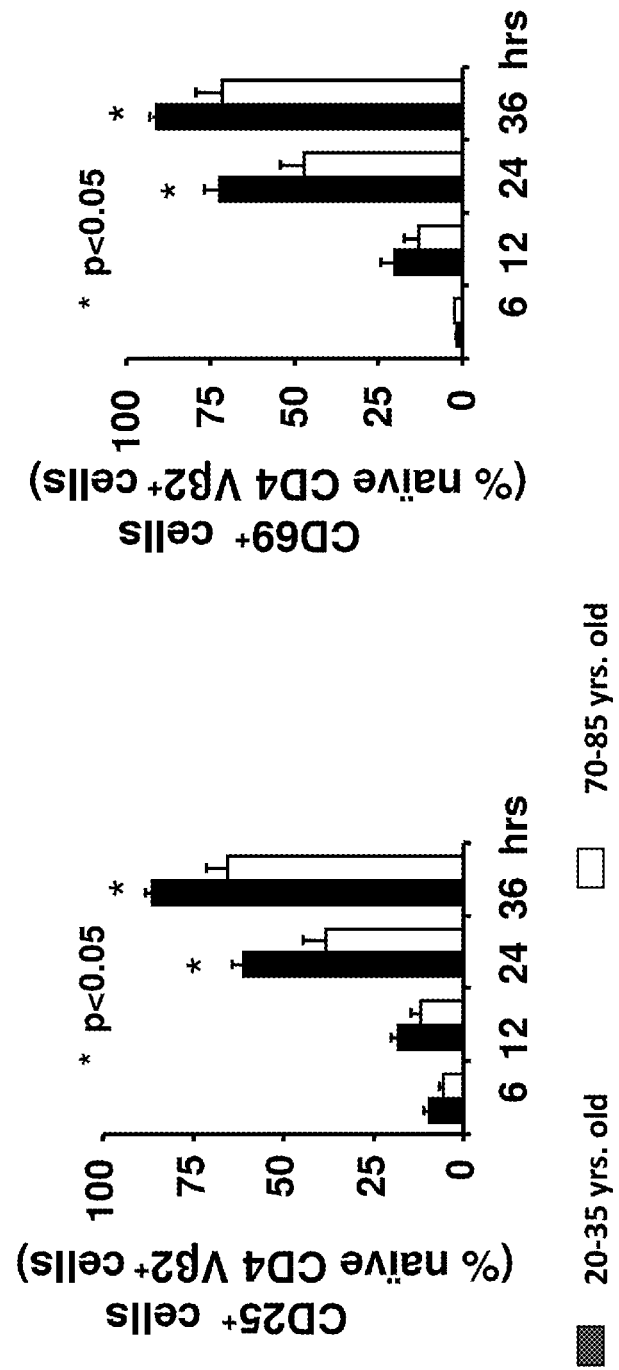

Similar results were obtained when the early activation markers, CD69 and CD25, were analyzed. CD25 and CD69 are T-cell activation markers that are sensitive to the activation of the extracellular signal-related kinase (ERK) signaling pathway. Expression of these activation markers in elderly naïve CD4-positive T cells was reduced starting as early as 6 hours after the initiation of the culture (FIG. 1B). These data suggest that early T cell activation events are defective in naïve CD4 T cells derived from elderly individuals and that the antigenic response in naïve CD4 T cells derived from elderly individuals is incompetent.

Example 2

Age-Related T Cell Receptor Signaling Defects

Figure 2A:
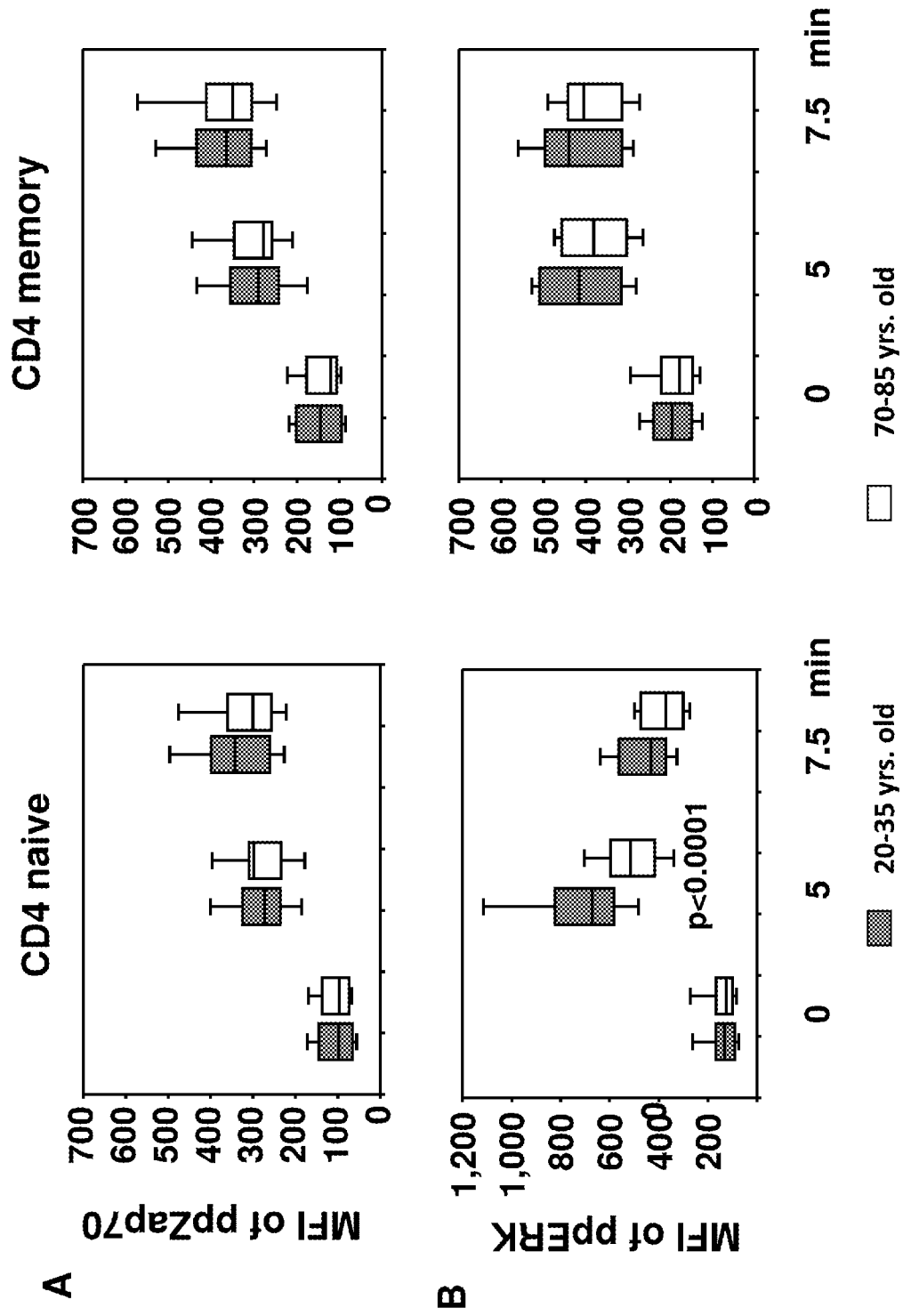
FIG. 2A illustrates ppZap70 (Panel A: 15 young and 15 elderly) and ppERK (Panel B: 20 young and 20 elderly) levels in CD4 naïve and memory T cells in two age groups after anti-CD3 stimulation, in accordance with embodiments of the present invention and as further detailed in Example 2.
Figure 2B:
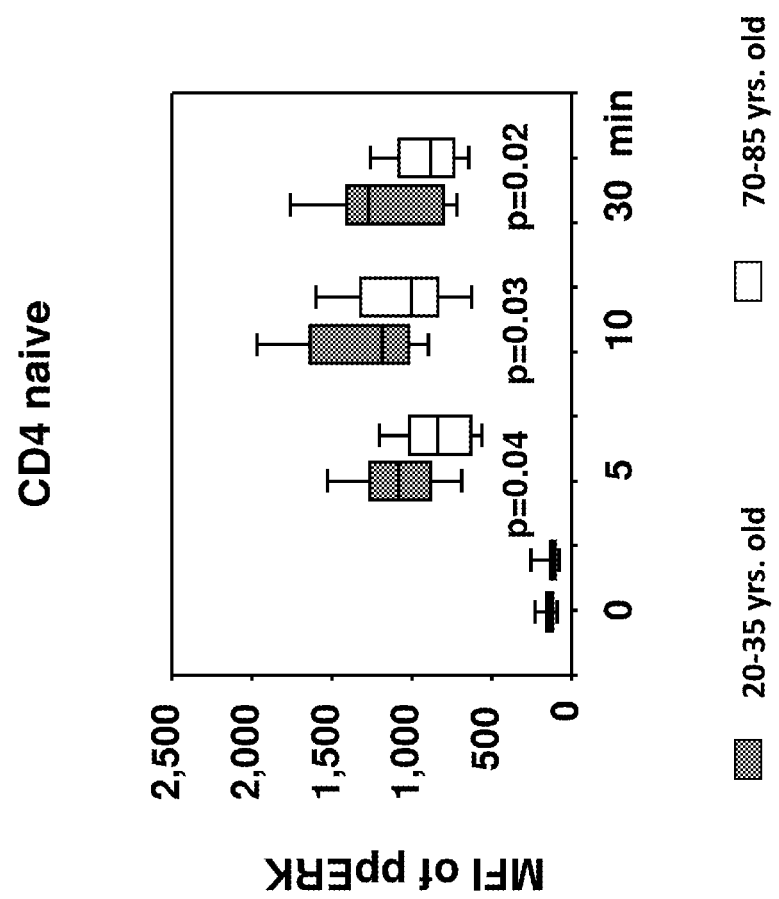
FIG. 2B shows ppErk levels in CD4 naïve T cells in two age groups after PMA stimulation (n=11), in accordance with embodiments of the present invention and as further detailed in Example 2.

Phosphoepitope analysis by flow cytometry was used to probe early signaling events after T-cell receptor stimulation. CD3 cross-linking induces phosphorylation of Zeta-chain-associated protein kinase 70 (ZAP70), a signal molecule and member of the protein-tyrosine kinase family immediately downstream of the TCR with a critical role in the initiation of T-cell signaling, in naïve and memory CD4 T cells from 20-35 year old and 70-85 year old adults without any obvious differences, suggesting that the initial signaling events are intact and not affected by age (FIG. 2A, panel A). However, naïve CD4 T cells from young adults were significantly more effective in phosphorylating ERK, in particular within the first 5 minutes after stimulation ($p<0.0001$). A similar defect in ERK phosphorylation was not seen for memory CD4 T cells (FIG. 2A, panel B). Subsequent studies using phorbol-12-myristate-13-acetate (PMA) confirmed that the defect in the elderly affects the ERK pathway distal of Ras/Raf activation. ERK phosphorylation downstream of PMA-induced PI3-kinase activation was also significantly different between the two age groups (FIG. 2B). These results suggest that ppERK incompetence in elderly naïve CD4 T cells is at least partially mediated by defects downstream of the TCR signal cascade.

Example 3

Age-Related Overexpression of the Dual Specificity Phosphatase 6 (DUSP6)

One of the major feedback loops that control the activation of the ERK pathway in T cells and that attenuates T-cell receptor signaling is the expression of the dual specificity phosphatases 5 and 6 (DUSP5 and DUSP6). In murine studies, increased DUSP6 protein expression during T-cell development has been implicated in the reduced sensitivity to respond to self-antigens in mature T cells compared to thymocytes. Given the selective decrease in TCR-induced ERK activation, we explored whether expression levels of DUSP6 increase with aging. As shown in FIG. 3A, panel A, DUSP6 was significantly more abundant in CD4 T cells from 70-85 year-old adults compared to CD4 T cells from young adults, as determined by Western blots ($p=0.02$). This increase was entirely attributed to the naïve CD4 population ($p=0.03$), no difference was seen for memory CD4 T cells (FIG. 3A, panel B).

We also examined protein tyrosine phosphatase, non-receptor type 22 (PTPN22), a potent negative regulator of leukocyte-specific protein tyrosine kinase (LcK) immediately downstream of TCR, and protein tyrosine phosphatase SHP-2, which can function as a cellular activation inhibitor by being recruited to inhibitory receptors such as CTLA4, KIRs. The expression of PTPN22 and SHP-2 was similar in the two age groups at both transcription (FIG. 3B) and translation levels (FIG. 3C). These data indicate that DUSP6-mediated pERK inactivation may play a central role in age-related defects of T-cell activation activity.

Example 4

Age-Related Loss in miR181a Accounts for Increased DUSP6 Expression

Increased DUSP6 protein expression with age was not reflected at the transcriptional level suggesting that a post-transcriptional defect is involved in DUSP6 regulation. One of the key posttranscriptional regulation mechanisms is the gene downregulation through microRNAs (miRNAs). As shown in FIG. 4A, DUSP6 transcript numbers in total CD4 T cells from twenty 20 to 35 and twenty 70 to 85 year old individuals were similar, as determined by qPCR. Memory CD4 T cells tended to have lower transcript levels than naïve CD4 T cells, both in the young and the old.

Li et al., 2007, recently reported that DUSP6 is one of several phosphatases in the mouse that is controlled by miR-181a. We therefore determined whether expression levels of miR-181a in CD4 T cells change with age. Results from twenty-one 20-35 and twenty-one 70-85 year-old individuals show a 3-fold decline in the elderly (FIG. 4B, panel A, p=0.0005) which was most attributed to the naïve population (FIG. 4B, panel B, p=0.0008). Memory CD4 T cells have lower miR-181a than naïve CD4 T cells in the young (p=0.004) and only show a small further decrease with age. In contrast, miR-142, examined as a system control, did not change with age (FIG. 4B, panel C).

To determine whether the decrease in miR-181a is responsible for the increased DUSP6 expression with age, we transfected CD4 T cells from elderly individuals with miR-181a and determined DUSP6 protein expression by Western blot. A representative experiment in FIG. 4C, panel B. shows the reduced DUSP6 band intensity in CD4 T cells that were transfected with miR-181a. In contrast to DUSP6, PTPN22 and SHP-2 which are also targeted by miR-181a in the mouse were not influenced by age (FIG. 3B).

Example 5

Normalization of miR-181a Expression Restores Naïve CD4-T Cell Responses in the Elderly The inverse expression pattern of DUSP6 and miR-181a might indicate that increased DUSP6 protein in the elderly CD4 naïve T cells may be caused by high miR-181a expression To determine whether inhibition of DUSP6 expression improves T-cell activation in the elderly, T cells from eleven 20 to 35 and eleven 70 to 85 year-old individuals were transfected with miR-181a precursor or Pre-miR negative control, and ERK phosphorylation after CD3 cross-linking was determined in gated naïve and memory CD4 T cells by Phospho-Flow (FIG. 5A). Consistent with the data shown in FIG. 2A, activation-induced ERK phosphorylation was reduced in elderly naïve, but not memory CD4 T cells. Overexpression of miR-181a improved the ERK response significantly in elderly naïve CD4 T cells (p=0.002) to approximately the same response level that is seen in the young adult. A lesser increase was seen in naïve CD4 T cells from young adults which still reached significance (p=0.03).

In contrast, the ERK response pattern in CD4 memory T cells was not influenced by miR-181a overexpression in the young adult and only slightly improved in the elderly (p=0.05). The increased ERK responses were functionally important. After TCR stimulation, CD4 T cells from elderly individuals expressed increased transcript numbers of IL-2 (p=0.03) and cyclin D1 (p=0.04), when transfected with miR-181a (FIG. 5B). In parallel, activation-induced expression of CD25 was improved in CD4 T cells from elderly, when transfected with miR-181a (FIG. 5C).

Example 6

Activation-Induced Expression of the Dual Specificity Phosphatase 4 (DUSP4) in Memory CD4 T Cells Increases with Age Vβ2+ CD4 memory T cells from four 20-35 and four 65-85 year-old individuals were stimulated with toxic shock syndrome toxin 1 TSST-1 presented by myeloid dendritic cells derived from young adults. Gene expression was examined at 16, 40 and 72 hours after stimulation using Affymetrix arrays. Probes were identified that were not different before stimulation but were different at 40 and 72 hours after stimulation. Eight-one probes were different with a probability of >0.9 at 40 hours and 83 probes at 72 hours, 67 probes of which were differentially expressed at both time-points with >0.9. The remaining 14 and 16 probes that reached a probability of >0.9 only at one time point were different with a probability of >0.8 at the other time-point suggesting that 97 probes were differentially expressed. Of these 97 probes, only 14 probes were already found to be different at 16 hours, suggesting that the majority of these genes are not early activation genes.

Figure 6A:
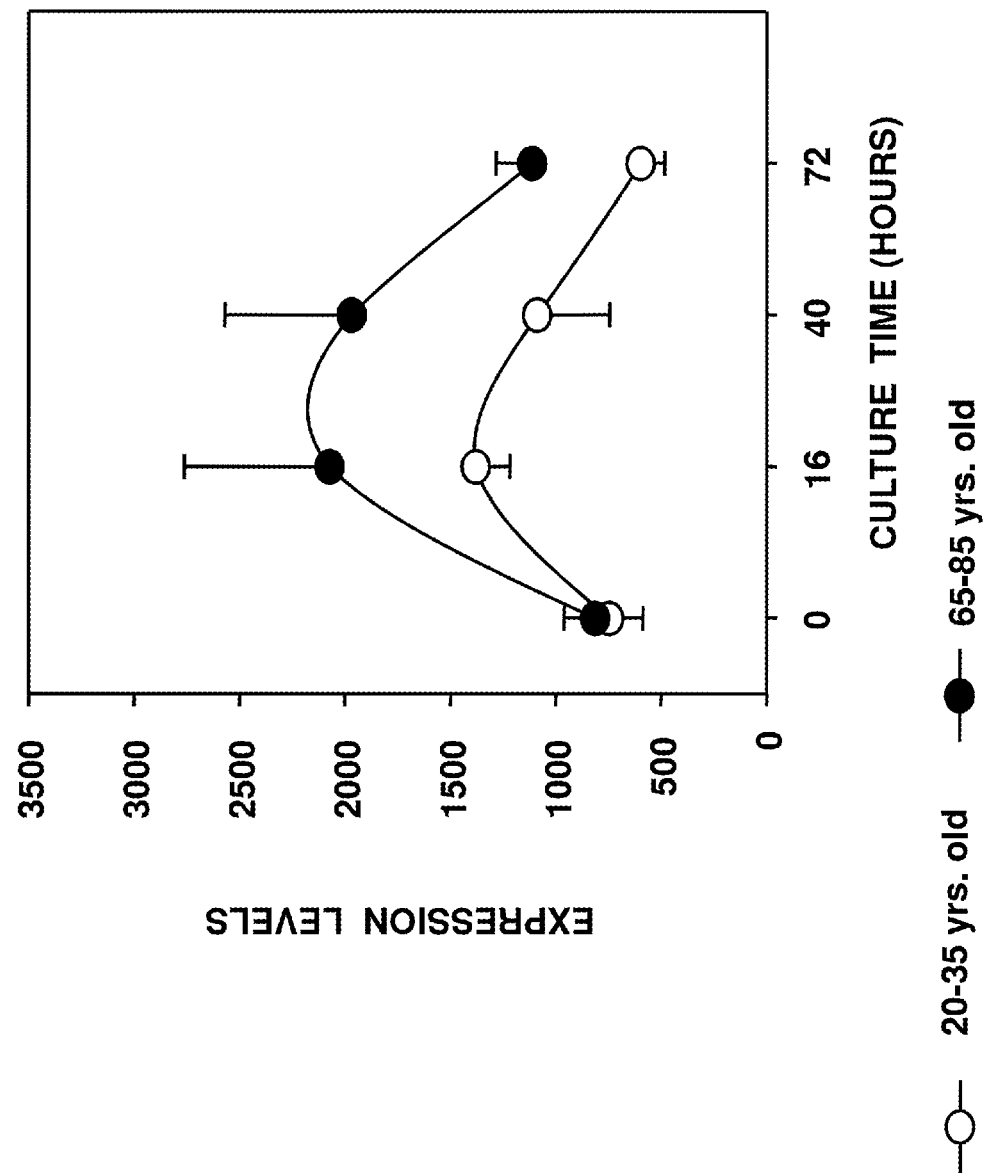
Figure 6E:
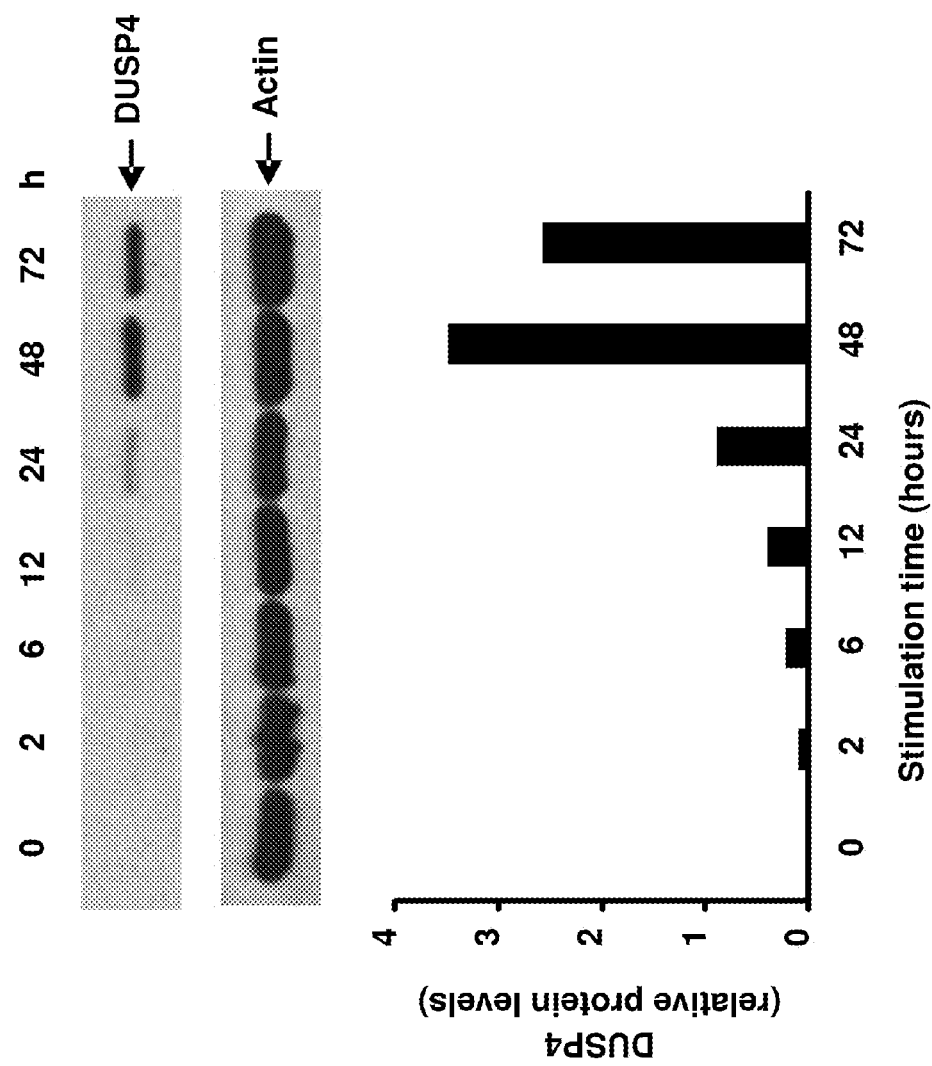

To identify pathways that may be targeted to improve vaccine responses in the elderly, we examined the panel of differentially expressed genes for the presence of signaling molecules. DUSP4 was represented with two different probes with an overexpression of the phosphatase at 72 hours for both probes and, in addition, at 48 hours for one of the probes (FIG. 6A). DUSP4 was not expressed in resting naïve or memory CD4 T cells, but transcription was induced within the first 48 hours in both cell populations. Naïve CD4 T cells displayed a higher and more sustained induction than memory CD4 cells (FIG. 6B). The kinetics in naïve CD4 T cells was not dependent of age; in contrast, transcription of DUSP4 in CD4 memory T cell responses was reduced and shortened in young adults compared to the elderly (FIG. 6B). DUSP4 transcript numbers 48 hours after anti-CD3/anti-CD28 stimulation (FIG. 6C) or 72 hours after stimulation with dendritic cells and TSST (FIG. 6D) was significantly increased in CD4 memory T cell responses of 65-85 compared to 20-35 year-old healthy individuals (p<0.001 and p=0.03, respectively). Western blot data paralleled the transcriptional results. DUSP4 protein expression peaked after 48 hours after CD3/CD28 stimulation and then started to decline in young individuals (FIG. 6E). DUSP4 protein expression at 48 hours was less in 20-35 than 65-85 year-old healthy individuals (p=0.03, FIG. 6F). Reporter gene assays using DUSP4 promoter constructs confirmed that the overexpression was transcriptionally caused.

In these experiments, CD4 memory T cells were stimulated on anti-CD3/anti-CD28 coated plates. Cells were transfected with reporter gene constructs and reporter gene activity was assessed 48 hours after initial stimulation and 12 hours after transfection. Reporter gene activity in memory CD4 T cells from elderly individuals was significantly higher (p<0.001). This difference was also maintained when cells were maximally stimulated by adding ionomycin and PMA during the last 4 hours of stimulation (p=0.003). These data demonstrate that activation-induced transcription of DUSP4 increases with age and results in increased and most sustained DUSP4 protein expression in elderly CD4 memory T cell responses.

Example 7

DUSP4 Dampens CD4 Memory T Cell Activation

To examine the functional consequences of DUSP4 expression in memory CD4 T cell responses, DUSP4 was overexpressed by transfection. Experiments in FIG. 7A show that transfected DUSP4 had the predicted substrate specificity. In T cells transfected with a DUSP4-containing vector and then activated by anti-CD3 cross-linking, ERK and JNK phosphorylation 10 minutes after cross-linking was blunted, while phosphorylation of p38 was not affected (FIG. 7A). This DUSP4 construct was then used to examine the consequences of increased DUSP4 expression during T cell differentiation. To mimic the findings in CD4 memory T cells from elderly individuals, CD4 memory T cells from young adults were activated on plates coated with anti-CD3/anti-CD28 antibodies for 36 hours and then transfected with a DUSP4-containing vector or a control vector. Cells were then assayed for the sustained expression of activation markers 48 hours after the initial activation. Expression of CD25 was not affected by increased DUSP4. In contrast, DUSP4 overexpressing cells showed a faster decline in the activation-induced cell surface density of CD69 (p<0.001), CD40-ligand (p<0.001) and ICOS (p<0.001). When cells were restimulated after 48 hours with ionomycin and PMA and assayed for the production of cytokines by flow cytometry, IL-2 expression was infrequent, consistent with activated CD4 T cells being effector cells. DUSP4 overexpression neither increased the frequency (by impairing effector cell differentiation) nor decreased IL-2 production (by interfering with T cell activation). In contrast, IL-4 (p<0.001), IL-17a (p<0.001), and IL-21 production (p<0.001) were all suppressed by the overexpression of DUSP4. These data suggest that DUSP4 in CD4 memory T cell responses impairs CD4 effector cell differentiation with preferential inhibition of some, but not all, effector functions.

Example 8

DUSP4 Silencing Improves T Cell Activity in the Elderly

If increased induced expression of DUSP4 accounts for immune defects in the elderly, similar patterns in elderly CD4 T cell responses should be evident as found in memory T cells from young adults that were manipulated for their DUSP4 expression. Indeed, the initial induction of T cell activation markers was found to be intact in the elderly, while their sustained expression was reduced. In FIG. 8A, CD4 memory T cells from eleven 20-35 year-old and eleven 65-85 year-old individuals were activated by culture on plates with immobilized anti-CD3/anti-CD28 antibodies and the expression of activation markers was determined after 48 and 72 hours. Expression of CD25 was not influenced by age, about 75% of all cells were positive after 48 hours and almost all cells expressed CD25 after 72 hours in this culture system. The expression of CD69 was already declining at these time points; the decline was faster in CD4 memory cells from the elderly and reached significance after 72 hours. Similarly, the expression of CD40-ligand was more sustained in young memory CD4 T cells; at 48 hours, only a minor age-related difference was seen (p=0.03) which clearly widened by 72 hours (p<0.001). These results mirrored CD4 memory T cell responses of young adults with transfected DUSP4. Only ICOS behaved differently in the two experimental systems. After 72 hours, only a minor trend was noticed towards reduced ICOS expression in the elderly CD4 memory T cells.

Figure 8B:
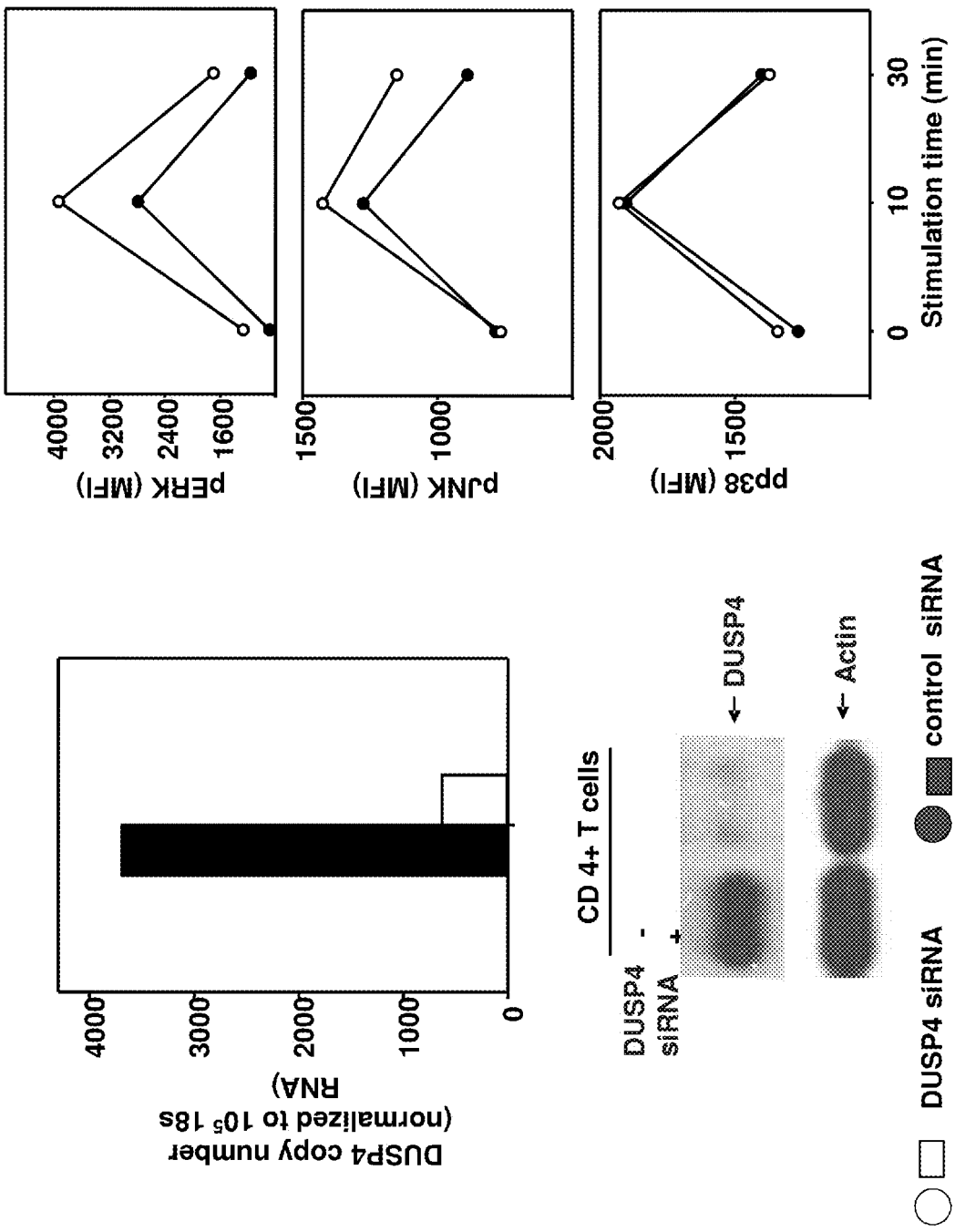
Figure 8D:
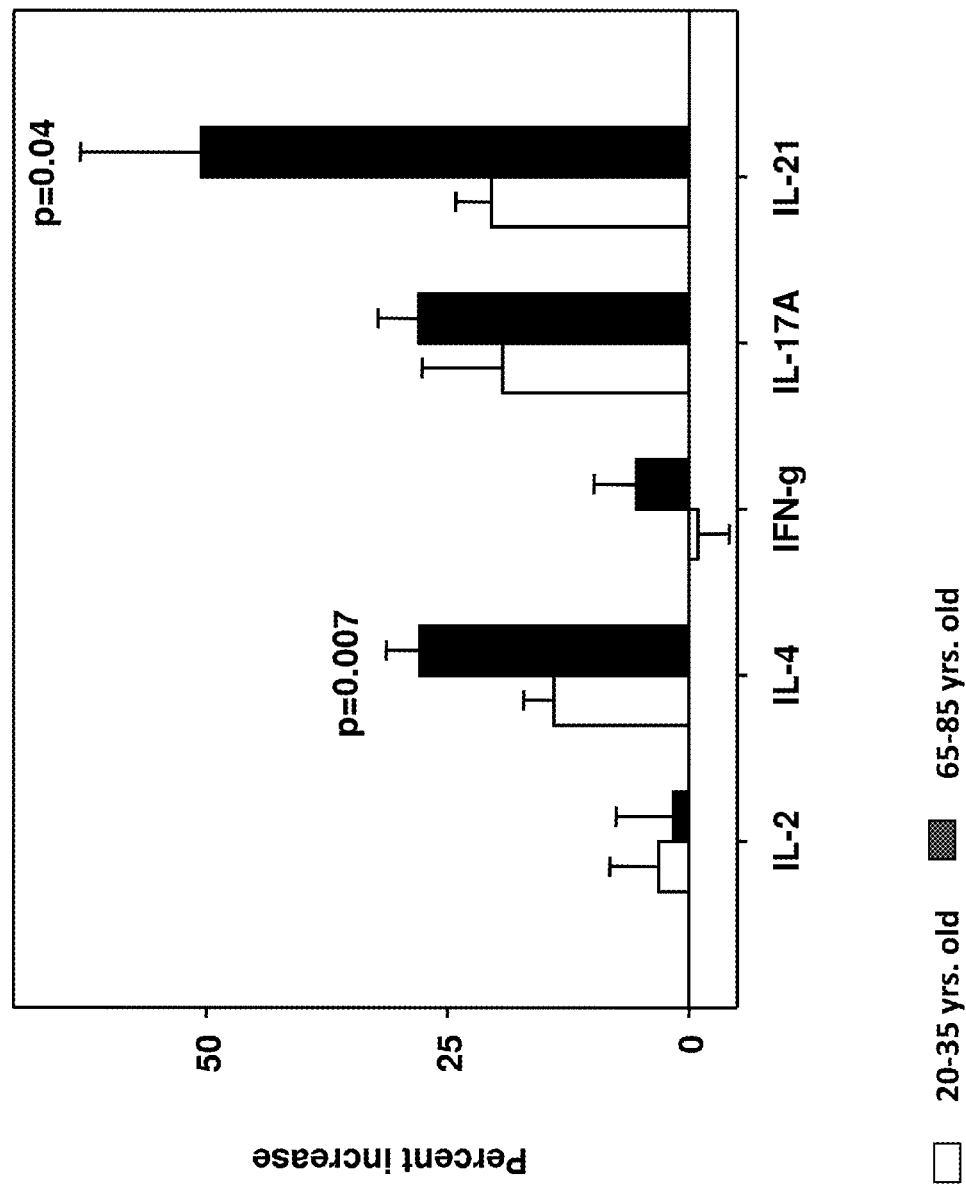
Figure 8E:
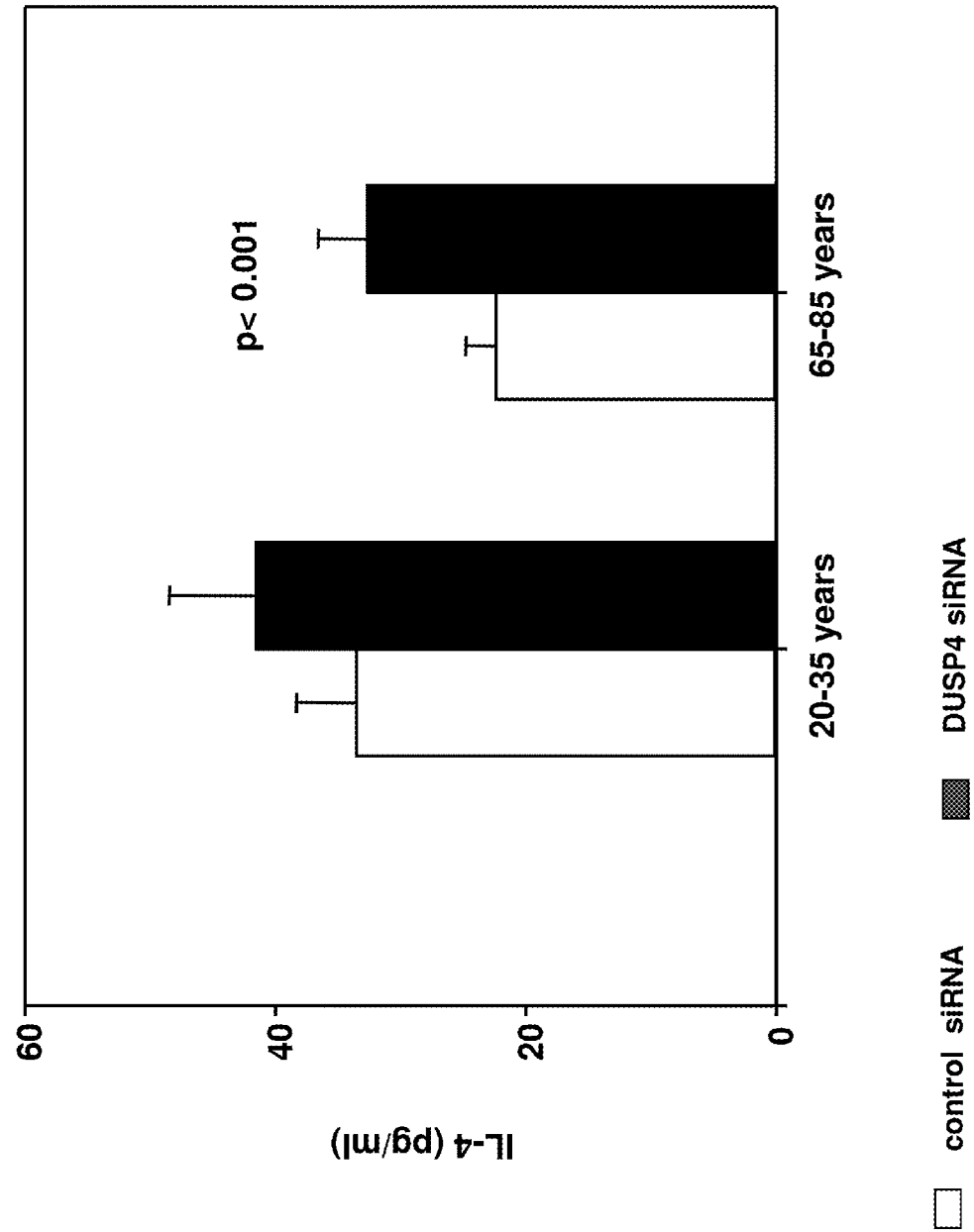

To address the question whether inhibition of DUSP4 transcription improved the functional activity of elderly CD4 memory T cells, the activation-induced transcription of DUSP4 was silenced (FIG. 8B). Transfection of CD4 memory T cells from elderly individuals with DUSP4-specific siRNA clearly suppressed the induction of protein expression. The repression of DUSP4 had the expected functional consequences on the MAP kinase signaling pathways; memory CD4 T cells from elderly individuals that were transfected with the DUSP4-specific siRNA and activated for 48 hours had increased ERK and JNK phosphorylation upon restimulation compared to control transfected T cells (FIG. 8B). The silencing of DUSP4 did not impact p38 phosphorylation; functional consequences of DUSP4 silencing are shown in FIG. 8C-E. In these experiments, the influence of DUSP4 silencing on the expression of activation markers and the production of cytokines were determined by comparing the responses of CD4 memory T cells silenced for DUSP4 to control transfected cells in eleven 20-35 year-old and eleven 65-85 year-old healthy individuals. DUSP4 silencing did not significantly affect the expression of CD25, neither in the CD4 memory T cells of young adults nor of the elderly individuals. In contrast, the expression of CD69, CD40-ligand, and ICOS were increased by silencing DUSP4. This improvement was relatively minor for young individuals and averaged 10-20% for all three activation markers tested. In contrast, elderly CD4 memory T cell responses benefitted more from silencing; in particular, the expression of CD40-ligand increased by close to 50% (p<0.001 compared to the improvement seen with young CD4 memory T cells).

A similar pattern was observed for cytokine expression. In these experiments, CD4 memory T cells were restimulated 48 hours after the initial stimulation and assayed for the presence of cytoplasmic cytokines by flow cytometry. DUSP4 silencing did not significantly influence the production of IL-2 or IFN-γ, neither in CD4 memory T cells from young nor from elderly individuals. In contrast, the production of IL-4, IL-17a and IL-21 was increased as a consequence of DUSP4 silencing. For all three cytokines, this increase was most pronounced in CD4 memory T cell responses from the elderly, in particular, DUSP4 silencing caused a higher increase in the frequencies of IL-4 (p=0.007) and IL-21 (p=0.04) producing T cells compared to the improvement that was seen in CD4 memory T cells of young adults. The flow cytometric analyses were confirmed by ELISA (FIG. 8E). Concentrations of IL-4 in culture supernatants harvested 48 hours after activation were lower with T cells from 65-85 year-old individuals compared to young adults. This impaired production was, in part, restored by the silencing of DUSP4 (p=0.001).

Example 9

DUSP4 Silencing in CD4 Memory T Cells Improves T Cell-Dependent B Cell Responses Based on the finding that overexpression of DUSP4 preferentially impairs CD40-ligand expression and the production of IL-4 and IL-21, DUSP4 expression was expected to play an important role in controlling T helper function for B cell differentiation. To examine the influence of age on the ability of memory CD4 T cells to provide help for B cell differentiation, a coculture system was developed that consisted of both T cells obtained from 20-35 year-old as well as 65-85 year-old individuals and B cells from young healthy adults ("T-B cell coculture system"). T cells were treated with mitomyocin C to prevent proliferation, activated with anti-CD3 and anti-CD28 and cocultured with B cells. Successful B cell differentiation was defined as the generation of $CD19^+$ $CD38^+$ or $CD19^+CD27^+$ cells.

In the absence of activated T cells, B cells stayed quiescent without starting to express CD38 and loosing IgD expression. In the presence of T cells activated with anti-CD3, a population of $IgD^- CD38^+$ B cells emerged which was more frequent when B cells were cocultured with CD4 memory T cells from young adults compared to elderly adults (p=0.004, FIG. 9A). Also, reduced expression of CD86 and CD27 was consistent with defective B cell activation and differentiation depending on the age of the T cell donor. Silencing of DUSP4 in the CD4 memory T cell population only marginally improved B cell differentiation supported by T cells from young individuals, but restored the B cell response in the coculture system with elderly CD4 T cells to a similar level as seen for the young individuals. Results from coculture systems with T cells from ten 20 to 35 and ten 65-85 year-old healthy individuals are summarized in FIG. 9B. All B cells were derived from unrelated young adults. Results are expressed as percent increase in the culture with DUSP4 silenced compared to control transfected T cells. In cultures with T cells from young adults, only 10-20% improvement was seen with DUSP4 silencing. In contrast, in the cultures with memory CD4 T cells from the elderly a much more striking improvement was seen; cell surface expression of CD86 increased by nearly 50%, the frequency of CD27$^+$ B cells increased by 30-40% and, in particular, the frequency of CD38$^+$ IgD$^-$ cells nearly doubled. This improvement was significantly more pronounced compared to the effect of DUSP4 silencing on the B cell help provided by young CD4 memory T cells.

The transcription factor E47 (FIG. 9C) was quantified as an additional marker of B cell differentiation. Expression of E47 is dependent on p38 activity and, in a T-B cell coculture system, may reflect CD40-ligand induced CD40 stimulation and activation of the p38 pathway. E47 expression was significantly lower in B cells that were cocultured with memory CD4 T cells from 65-85 year-old individuals (p=0.002). DUSP4 silencing in the T cell population only marginally improved the ability of young T cells to upregulate E47 expression. In contrast, when B cells were differentiated by CD4 memory T cells from 65-85 year-old individuals, E47 expression significantly increased in B cells cocultured with DUSP4 silenced versus control transfected T cells (p=0.002), although the improvement remained partial.

Example 10

DUSP4 Expression in T Cells Suppresses Humoral Responses after Immunization In Vivo (in Mice)

Data so far clearly showed that increased DUSP4 in activated CD4 memory T cells impaired their ability to express molecular mediators important in providing help for B cell differentiation and that DUSP4 overexpression, at least in part, was responsible for the impaired T cell-dependent B cell responses in the elderly. To examine the validity of this hypothesis for an immunization response in vivo, T cells from TCR transgenic OT-II mice were transduced with a DUSP4 expressing vector or a control retroviral vector and adoptively transferred into CD4 knockout mice. Mice were immunized intraperitoneally with NP-Ova in alum, and cellular and humoral immune responses to the immunization were assessed on day 14. Frequency of adoptively transferred CD4 T cells in the spleens of the host was not different irrespective of whether the T cells were transfected with the control or the DUSP4 expressing vector. However, CD40-ligand and ICOS expression was significantly reduced by DUSP4 expression (FIG. 10A). Enumeration of splenic cell populations showed equal numbers of approximately 40-50 million B cells and 1.5 million T cells irrespective of whether the T cells overexpressed DUSP4 or not. The frequency of NP-specific B cells was significantly lower when DUSP4-transduced T cells were adoptively transferred (p=0.003). A striking difference was also found for antigen-specific B cells that expressed a germinal center phenotype; such antigen-specific B cells were nearly absent in hosts adoptively transferred with DUSP4-expressing T cells compared to approximately 400,000 in the mice adoptively transferred with the control transduced T cells (p=0.009). The detrimental effect of DUSP4 expression in T cells on the ability to support T cell-dependent B cell responses was further evident when antibody titers to the immunizing antigen ovalbumin were compared. The induction of ovalbumin-specific IgG after immunization was about fivefold reduced in mice adoptively transferred with the DUSP4 transduced T cells.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

Alexander C et al. (2009). T-cell immunosenescence: lessons learned from mouse models of aging. *Trends Immunol* 30:301-305.

Bartel D P (2004). MicroRNAs: genomics, biogenesis, mechanism, and function. *Cell* 116:281-97.

Chang L & Karin M (2001). Mammalian MAP kinase signaling cascades. *Nature* 410, 37-40.

Clambey E T et al. (2005). Non-malignant clonal expansions of CD8+ memory T cells in aged individuals. *Immunol Rev* 205-170-189.

Clements J L et al. (1999). Integration of T cell receptor-dependent signaling pathways by adapter proteins. *Annu. Rev. Immunol.* 17, 89-108.

Davidson-Moncada J et al. (2010). MicroRNAs of the immune system: roles in inflammation and cancer. *Ann NY Acad Sci* 1183:183-94.

Donahue J G et al. (1995). The incidence of herpes zoster. *Arch Intern Med* 155:1605-1609.

Douek D C at al. (1998). Changes in thymic function with age and during the treatment of HIV infection. *Nature* 396: 690-695.

Ducruet A P et al. (2005). Dual specificity protein phosphatases: therapeutic targets for cancer and Alzheimer's disease. *Annu. Rev. Med.* 45:725-750.

Fisman D N et al. (2002). The effect of age on immunologic response to recombinant hepatitis B vaccine: a meta-analysis. *Clin Infect Dis* 35:1368-1375.

Goronzy J J et al. (2007). Aging and T-cell diversity. *Exp Gerontol* 42:400-406.

Hakim F T & Gress R E (2007). Immunosenescence: deficits in adaptive immunity in the elderly. *Tissue Antigens* 70: 179:189.

Haynes B F et al. (2000). The role of the thymus in immune reconstitution in aging, bone marrow transplantation, and HIV-1 infection. *Annu Rev Immunol* 18: 529-560

Haynes L & Swain S L (2006). Why Aging T Cells Fail: Implications for Vaccination. *Immunity*, 24: 663-666

Janeway C A & Medzhitov R (2002). Innate immune recognition. *Ann Rev Immunol* 20: 197-216.

Jeffrey K L, et al. (2007). Targeting dual-specificity phosphatases: manipulating MAP kinase signaling and immune responses. *Nat. Rev.* 6:391-403.

Kuida K & Boucher D M (2004). Functions of MAP Kinases: Insights from Gene-Targeting Studies. *J Biochem* 135:653-656.

Langenkamp A et al. (2002). T cell priming by dendritic cells: thresholds for proliferation, differentiation and death and intraclonal functional diversification. *Eur J Immunol* 32:2046-54.

Lee WW et al. (2008). Age-dependent signature of metallothionein expression in primary CD4 T cell responses is due to sustained zinc signaling. *Rejuvenation Research* 11: 1001-1011

Liu Y et al. (2007). MAPK phosphatases-regulationg the immune response. *Nat Rev Immunol* 7: 202-12.

Li Q-J et al. (2007). miR-181a is an intrinsic modulator of T cell sensitivity and selection. *Cell* 129:147-161.

Messaoudi I et al. (2004). Age-related CD8 T cell clonal expansions constrict CD8 T cell repertoire and have the potential to impair immune defense. *J Exp Med* 200:1347-1358.

Naylor K et al. (2005). The influence of age on T cell generation and TCR diversity. *J Immunol* 174: 7446-7452.

Nichol K L et al. (2007). Effectiveness of influenza vaccine in the community-dwelling elderly. *N Engl J Med* 357: 1373-1381.

Nicolich-Zugich J et al. (2004). The many important facets of T-cell repertoire diversity. *Nat Rev Immunol* 4:123-132.

Parish I A & Kaech S M (2009). Diversity in CD8(+) T cell differentiation. *Curr Opin Immunol* 21:291-7.

Patterson K I, et al. (2009). Dual-specificity phosphatases: critical regulators with diverse cellular targets. *Biochem. J.* 418:475-489.

Salojin & Oravecz (2007). Regulation of innate immunity by MAPK dual-specificity phosphatases: knockout models reveal new tricks of old genes. *J. Leukocyt. Biol.* 81:860-869.

Surh C D et al. (2006). Homeostasis of memory T cells. *Immunol Rev* 211:154-63.

Targonski P V et al. (2007). Immunosenescence: role and measurement in influenza vaccine response among the elderly. *Vaccine* 25: 3066-3069.

Thompson W W et al. (2003). Mortality associated with influenza and respiratory syncytial virus in the United States. *JAMA* 289: 179-186.

Teixeiro E & Daniels M A (2010). ERK and cell death: ERK location and T cell selection. *FEBS Journal* 277:30-38.

Vogt A et al. (2003). Cell-Active Dual Specificity Phosphatase Inhibitors Identified by High-Content Screening. *Chem Biol* 10:733-742.

Wan Y Y & Flavell R A (2009). How diverse—CD4 effector T cells and their functions. *J Mol Cell Biol* 1:20-36.

Weng N P et al. (2009). CD28(−) T cells: their role in the age-associated decline of immune function. *Trends Immunol* 30:306-312.

Weng N P (2006). Aging of the immune system: how much can the adaptive immune system adapt? *Immunity* 24:495-499.

Zhou L et al. (2009). Plasticity of CD4+ T cell lineage differentiation. *Immunity* 30:646-55.

What is claimed is:

1. A method of restoring T cell-mediated immune response to an exogenous immunogen in an individual whose immune response is compromised, the method comprising: administering a pharmaceutical composition comprising a modulator of activity or expression of dual specificity phosphatase 4 to said individual in a therapeutically effective amount and within a predetermined time period before, during or after administration of said immunogen, whereby the modulator of activity or expression is an antisense polynucleotide capable of hybridizing to SEQ ID NO:9.

2. The method of claim 1, wherein said individual is of advanced age.

3. The method of claim 1, wherein said individual is of middle age.

4. The method of claim 1, wherein said modulator is a small molecule pharmacological inhibitor of said dual specificity phosphatase 4.

5. The method of claim 1, wherein said modulator down-regulates the expression of said dual specificity phosphatase 4.

6. The method of claim 1, wherein said administration is oral, systemic or local.

7. A method of enhancing T cell-mediated immune response to an exogenous immunogen in an individual whose immune response is compromised, the method comprising: administering a pharmaceutical composition comprising a modulator of activity or expression of at least one dual specificity phosphatase to said individual in a therapeutically effective amount and within a predetermined time period before, during or after administration of said immunogen, whereby the modulator of activity or expression is an antisense polynucleotide capable of hybridizing to SEQ ID NO:9.

8. The method of claim 7, wherein said individual is of advanced age.

9. The method of claim 7, wherein said individual is of middle age.

10. The method of claim 7, wherein said dual specificity phosphatase is dual specificity phosphatase 4.

11. The method of claim 7, wherein said modulator is a small molecule pharmacological inhibitor of said dual specificity phosphatase 4.

12. The method of claim 7, wherein said modulator down-regulates the expression of said dual specificity phosphatase 4.

13. The method of claim 7, wherein said administration is oral, systemic or local.

* * * * *

UNITED STATES PATENT AND TRADEMARK OFFICE
CERTIFICATE OF CORRECTION

Page 1 of 1

PATENT NO. : 8,685,938 B2
APPLICATION NO. : 13/082790
DATED : April 1, 2014
INVENTOR(S) : Jorg J. Goronzy, Cornelia Weyand and Mingcan Yu It is certified that error appears in the above-identified patent and that said Letters Patent is hereby corrected as shown below:

In the Specification

Column 1, Lines 16-19 (approx.), should read:
This invention was made with Government support under contracts AI057266 and AG015043 awarded by the National Institutes of Health. The Government has certain rights in the invention.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*

```
                         SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(20)

<400> SEQUENCE: 1
cagtggtgct ctacgacgag                                            20

<210> SEQ ID NO 2
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(21)

<400> SEQUENCE: 2
gcaatgcagg gagaactcgg c                                          21

<210> SEQ ID NO 3
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(20)

<400> SEQUENCE: 3
```

```
gaagtggaga gaggaaagag                                                    20

<210> SEQ ID NO 4
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(22)

<400> SEQUENCE: 4
gtccgaaagt ggtattgcca ga                                                 22

<210> SEQ ID NO 5
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(22)

<400> SEQUENCE: 5
ttctctgtat cctgtgaagc tg                                                 22

<210> SEQ ID NO 6
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(24)

<400> SEQUENCE: 6
ctgtcatcct cttggtaaca acgt                                               24

<210> SEQ ID NO 7
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(21)

<400> SEQUENCE: 7
atggccacgg ctgcttccag c                                                  21

<210> SEQ ID NO 8
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(21)

<400> SEQUENCE: 8
catggtggtg ccgccagaca g                                                  21

<210> SEQ ID NO 9
<211> LENGTH: 21
```

```
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(21)

<400> SEQUENCE: 9
tggcaataag gactccgaat a                                              21

<210> SEQ ID NO 10
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(21)

<400> SEQUENCE: 10
ggatctgtgg gtttcatcac t                                              21

<210> SEQ ID NO 11
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(19)

<400> SEQUENCE: 11
tgtgccaact gcacctcaa                                                 19

<210> SEQ ID NO 12
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(20)

<400> SEQUENCE: 12
gggattcagg ttccgctctc                                                20

<210> SEQ ID NO 13
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(22)

<400> SEQUENCE: 13
agggaattcc cgagtaagtg cg                                             22

<210> SEQ ID NO 14
<211> LENGTH: 19
<212> TYPE: DNA
<213> ORGANISM: Artificial Sequence
<220> FEATURE:
<223> OTHER INFORMATION: primer
<220> FEATURE:
```

```
<221> NAME/KEY: primer_bind
<222> LOCATION: (1)..(19)

<400> SEQUENCE: 14
gcctcactaa accatccaa                                                    19
```